US009468442B2

(12) United States Patent
Huynh et al.

(10) Patent No.: US 9,468,442 B2
(45) Date of Patent: Oct. 18, 2016

(54) VASCULAR REMODELING DEVICE

(75) Inventors: Andy Huynh, Westminster, CA (US); Masoud Molaei, Mountain View, CA (US); Victoria Schuman, Long Beach, CA (US); Sanjay Shrivastava, Irvine, CA (US); Earl Slee, Laguna Niguel, CA (US); Quang Tran, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 745 days.

(21) Appl. No.: 13/016,855

(22) Filed: Jan. 28, 2011

(65) Prior Publication Data

US 2011/0184452 A1   Jul. 28, 2011

Related U.S. Application Data

(60) Provisional application No. 61/299,254, filed on Jan. 28, 2010.

(51) Int. Cl.
*A61F 2/06* (2013.01)
*A61B 17/12* (2006.01)
(Continued)

(52) U.S. Cl.
CPC ..... *A61B 17/12118* (2013.01); *A61B 17/1214* (2013.01); *A61B 17/12172* (2013.01);
(Continued)

(58) Field of Classification Search
CPC .................. A61B 17/12118; A61B 17/12172; A61B 17/12113; A61B 17/12099; A61B 17/12104; A61B 17/12109; A61B 17/121118; A61B 17/1214; A61B 17/12145; A61B 17/12163; A61B 17/12168; A61B 17/12177; A61F 2002/823; A61F 2/823; A61F 2/86; A61F 2/88

USPC ................................. 623/1.11; 606/191, 200
See application file for complete search history.

(56) References Cited

U.S. PATENT DOCUMENTS

| 3,108,593 A | 10/1963 | Glassman |
| 4,425,908 A | 1/1984 | Simon |

(Continued)

FOREIGN PATENT DOCUMENTS

| CA | 2607529 | 4/2008 |
| CN | 101472537 A | 7/2009 |

(Continued)

OTHER PUBLICATIONS

International Preliminary Report on Patentability for International Application No. PCT/US2009/051316; dated Jan. 25, 2011.
(Continued)

*Primary Examiner* — Katherine M Shi
*Assistant Examiner* — Lindsey Bachman
(74) *Attorney, Agent, or Firm* — Mark J. Kertz, Esq.

(57) ABSTRACT

An intraluminal apparatus including a catheter and device is positionable at a junction of afferent and efferent vessels of a bifurcation having an aneurysm. After positioning the device to substantially conform the device to the shape of the junction, the device acts as a scaffolding to inhibit herniation of objects out of the aneurysm and the device permits perfusion to the efferent vessels. Positioning the device may include deployment and optional release from a catheter. Embolic material may be inserted in the aneurysm before or after positioning the device. The device may have a proximal end, a distal end, and a plurality of filaments extending between and coupled at the proximal end and the distal end. The device may include a central filament configured to reshape the device. The distal end of the device may include a covering. The device may be football shaped, pumpkin shaped, or acorn shaped.

19 Claims, 40 Drawing Sheets

(51) Int. Cl.
*A61F 2/856* (2013.01)
*A61F 2/86* (2013.01)
*A61F 2/82* (2013.01)
*A61F 2/95* (2013.01)

(52) U.S. Cl.
CPC ............... *A61F2/856* (2013.01); *A61F 2/86* (2013.01); *A61F 2002/823* (2013.01); *A61F 2002/9528* (2013.01); *A61F 2002/9534* (2013.01); *A61F 2230/0063* (2013.01); *A61F 2230/0071* (2013.01)

(56) References Cited

U.S. PATENT DOCUMENTS

| | | | |
|---|---|---|---|
| 4,619,246 | A | 10/1986 | Molgaard-Nielsen et al. |
| 4,655,771 | A | 4/1987 | Wallsten |
| 4,768,507 | A | 9/1988 | Fischell et al. |
| 4,921,484 | A | 5/1990 | Hillstead |
| 4,998,539 | A | 3/1991 | Delsanti |
| 5,026,377 | A | 6/1991 | Burton et al. |
| 5,061,275 | A | 10/1991 | Wallsten et al. |
| 5,064,435 | A | 11/1991 | Porter |
| 5,104,404 | A | 4/1992 | Wolff |
| 5,122,136 | A | 6/1992 | Guglielmi et al. |
| 5,158,548 | A | 10/1992 | Lau et al. |
| 5,222,971 | A | 6/1993 | Willard et al. |
| 5,250,071 | A | 10/1993 | Palermo |
| 5,334,210 | A | 8/1994 | Gianturco |
| 5,378,239 | A | 1/1995 | Termin et al. |
| 5,405,379 | A | 4/1995 | Lane |
| 5,425,984 | A | 6/1995 | Kennedy et al. |
| 5,484,444 | A | 1/1996 | Braunschweiler et al. |
| 5,499,981 | A | 3/1996 | Kordis |
| 5,527,338 | A | 6/1996 | Purdy |
| 5,545,208 | A | 8/1996 | Wolff et al. |
| 5,545,209 | A | 8/1996 | Roberts et al. |
| 5,549,635 | A | 8/1996 | Solar |
| 5,624,461 | A | 4/1997 | Mariant |
| 5,634,942 | A | 6/1997 | Chevillon et al. |
| 5,645,558 | A | 7/1997 | Horton |
| 5,662,703 | A | 9/1997 | Yurek et al. |
| 5,690,671 | A | 11/1997 | McGurk et al. |
| 5,702,419 | A | 12/1997 | Berry et al. |
| 5,713,907 | A | 2/1998 | Hogendijk et al. |
| 5,725,552 | A | 3/1998 | Kotula et al. |
| 5,728,906 | A | 3/1998 | Eguchi et al. |
| 5,733,294 | A | 3/1998 | Forber et al. |
| 5,741,333 | A | 4/1998 | Frid |
| 5,749,891 | A | 5/1998 | Ken et al. |
| 5,749,919 | A | 5/1998 | Blanc |
| 5,749,920 | A | 5/1998 | Quiachon et al. |
| 5,766,151 | A | 6/1998 | Valley et al. |
| 5,814,062 | A | 9/1998 | Sepetka et al. |
| 5,830,230 | A | 11/1998 | Berryman et al. |
| 5,846,261 | A | 12/1998 | Kotula et al. |
| 5,853,422 | A | 12/1998 | Huebsch et al. |
| 5,855,578 | A | 1/1999 | Guglielmi et al. |
| 5,879,366 | A | 3/1999 | Shaw et al. |
| 5,908,435 | A | 6/1999 | Samuels |
| 5,911,731 | A | 6/1999 | Pham et al. |
| 5,916,235 | A * | 6/1999 | Guglielmi ........ A61B 17/12022 606/194 |
| 5,925,060 | A | 7/1999 | Forber |
| 5,928,228 | A | 7/1999 | Kordis et al. |
| 5,928,260 | A | 7/1999 | Chin et al. |
| 5,935,148 | A | 8/1999 | Villar et al. |
| 5,935,362 | A | 8/1999 | Petrick |
| 5,941,249 | A | 8/1999 | Maynard |
| 5,944,738 | A | 8/1999 | Amplatz et al. |
| 5,951,599 | A | 9/1999 | McCrory |
| 5,957,948 | A | 9/1999 | Mariant |
| 5,976,162 | A | 11/1999 | Doan et al. |
| 5,980,554 | A | 11/1999 | Lenker et al. |
| 6,001,092 | A | 12/1999 | Mirigian et al. |
| 6,010,517 | A | 1/2000 | Baccaro |
| 6,024,756 | A | 2/2000 | Huebsch et al. |
| 6,033,423 | A | 3/2000 | Ken et al. |
| 6,036,720 | A | 3/2000 | Abrams et al. |
| 6,059,813 | A | 5/2000 | Vrba et al. |
| 6,063,070 | A | 5/2000 | Eder |
| 6,063,104 | A | 5/2000 | Villar et al. |
| 6,086,577 | A | 7/2000 | Ken et al. |
| 6,093,199 | A * | 7/2000 | Brown et al. ................ 606/200 |
| 6,096,034 | A | 8/2000 | Kupiecki et al. |
| 6,096,073 | A | 8/2000 | Webster et al. |
| 6,099,526 | A | 8/2000 | Whayne et al. |
| 6,106,530 | A | 8/2000 | Harada |
| 6,110,191 | A | 8/2000 | Dehdashtian et al. |
| 6,123,715 | A | 9/2000 | Amplatz |
| 6,139,564 | A | 10/2000 | Teoh |
| 6,152,144 | A | 11/2000 | Lesh et al. |
| 6,168,592 | B1 | 1/2001 | Kupiecki et al. |
| 6,168,615 | B1 | 1/2001 | Ken et al. |
| 6,168,618 | B1 | 1/2001 | Frantzen |
| 6,168,622 | B1 | 1/2001 | Mazzocchi |
| 6,183,495 | B1 | 2/2001 | Lenker et al. |
| 6,190,402 | B1 | 2/2001 | Horton et al. |
| 6,193,708 | B1 | 2/2001 | Ken et al. |
| 6,221,086 | B1 | 4/2001 | Forber |
| 6,261,305 | B1 * | 7/2001 | Marotta et al. ................ 606/200 |
| 6,280,412 | B1 | 8/2001 | Pederson, Jr. et al. |
| 6,306,141 | B1 | 10/2001 | Jervis |
| 6,309,367 | B1 | 10/2001 | Boock |
| 6,322,576 | B1 | 11/2001 | Wallace et al. |
| 6,325,820 | B1 | 12/2001 | Khosravi et al. |
| 6,331,184 | B1 | 12/2001 | Abrams |
| 6,332,576 | B1 | 12/2001 | Colley et al. |
| 6,342,068 | B1 | 1/2002 | Thompson |
| 6,344,041 | B1 | 2/2002 | Kupiecki et al. |
| 6,344,048 | B1 * | 2/2002 | Chin et al. ................ 606/200 |
| 6,346,117 | B1 | 2/2002 | Greenhalgh |
| 6,350,270 | B1 | 2/2002 | Roue |
| 6,361,558 | B1 | 3/2002 | Hieshima et al. |
| 6,368,339 | B1 | 4/2002 | Amplatz |
| 6,375,668 | B1 * | 4/2002 | Gifford ............ A61B 17/12022 606/200 |
| 6,379,372 | B1 | 4/2002 | Dehdashtian et al. |
| 6,383,174 | B1 | 5/2002 | Eder |
| 6,391,037 | B1 | 5/2002 | Greenhalgh |
| 6,409,750 | B1 | 6/2002 | Hyodoh et al. |
| 6,428,558 | B1 | 8/2002 | Jones et al. |
| 6,443,972 | B1 | 9/2002 | Bosma et al. |
| 6,447,531 | B1 | 9/2002 | Amplatz |
| 6,454,780 | B1 | 9/2002 | Wallace |
| 6,506,204 | B2 | 1/2003 | Mazzocchi |
| 6,511,468 | B1 | 1/2003 | Cragg et al. |
| 6,530,934 | B1 | 3/2003 | Jacobsen et al. |
| 6,544,278 | B1 | 4/2003 | Vrba et al. |
| 6,547,804 | B2 | 4/2003 | Porter et al. |
| 6,551,303 | B1 | 4/2003 | Van Tassel et al. |
| 6,569,179 | B2 | 5/2003 | Teoh et al. |
| 6,579,302 | B2 | 6/2003 | Duerig et al. |
| 6,579,303 | B2 | 6/2003 | Amplatz |
| 6,585,748 | B1 | 7/2003 | Jeffree |
| 6,585,756 | B1 | 7/2003 | Strecker |
| 6,589,256 | B2 | 7/2003 | Forber |
| 6,589,265 | B1 * | 7/2003 | Palmer ............ A61B 17/12022 606/200 |
| 6,592,605 | B2 | 7/2003 | Lenker et al. |
| 6,599,308 | B2 | 7/2003 | Amplatz |
| 6,605,102 | B1 | 8/2003 | Mazzocchi et al. |
| 6,605,111 | B2 | 8/2003 | Bose et al. |
| 6,607,551 | B1 | 8/2003 | Sullivan et al. |
| 6,613,074 | B1 | 9/2003 | Mitelberg et al. |
| 6,626,939 | B1 | 9/2003 | Burnside et al. |
| 6,632,241 | B1 | 10/2003 | Hancock et al. |
| 6,635,068 | B1 | 10/2003 | Dubrul et al. |
| 6,635,069 | B1 | 10/2003 | Teoh et al. |
| 6,652,555 | B1 | 11/2003 | VanTassel et al. |
| 6,652,556 | B1 | 11/2003 | VanTassel et al. |
| 6,666,882 | B1 | 12/2003 | Bose et al. |
| 6,666,883 | B1 | 12/2003 | Seguin et al. |
| 6,669,717 | B2 | 12/2003 | Marotta et al. |
| 6,669,721 | B1 | 12/2003 | Bose et al. |

(56) References Cited

U.S. PATENT DOCUMENTS

| | | | |
|---|---|---|---|
| 6,676,696 B1 | 1/2004 | Marotta et al. | |
| 6,682,505 B2 | 1/2004 | Bates et al. | |
| 6,682,546 B2 | 1/2004 | Amplatz | |
| 6,689,150 B1 | 2/2004 | VanTassel et al. | |
| 6,689,486 B2 | 2/2004 | Ho et al. | |
| 6,695,876 B1 | 2/2004 | Marotta et al. | |
| 6,698,877 B2 | 3/2004 | Urlaub et al. | |
| 6,699,274 B2 | 3/2004 | Stinson | |
| 6,709,465 B2 | 3/2004 | Mitchell et al. | |
| 6,712,835 B2 | 3/2004 | Mazzocchi et al. | |
| 6,723,112 B2 | 4/2004 | Ho et al. | |
| 6,723,116 B2 | 4/2004 | Taheri | |
| 6,730,108 B2 | 5/2004 | Van Tassel et al. | |
| 6,746,468 B1* | 6/2004 | Sepetka et al. | 606/200 |
| 6,746,890 B2 | 6/2004 | Gupta et al. | |
| 6,780,196 B2 | 8/2004 | Chin et al. | |
| 6,792,979 B2 | 9/2004 | Konya et al. | |
| 6,797,083 B2 | 9/2004 | Peterson | |
| 6,802,851 B2 | 10/2004 | Jones et al. | |
| RE38,653 E | 11/2004 | Igaki et al. | |
| 6,811,560 B2 | 11/2004 | Jones et al. | |
| 6,855,153 B2 | 2/2005 | Saadat | |
| 6,855,154 B2 | 2/2005 | Abdel-Gawwad | |
| RE38,711 E | 3/2005 | Igaki et al. | |
| 6,860,893 B2 | 3/2005 | Wallace et al. | |
| 6,936,055 B1 | 8/2005 | Ken et al. | |
| 6,949,103 B2 | 9/2005 | Mazzocchi et al. | |
| 6,949,113 B2 | 9/2005 | Van Tassel et al. | |
| 6,953,472 B2 | 10/2005 | Palmer et al. | |
| 6,979,341 B2 | 12/2005 | Scribner et al. | |
| 6,989,019 B2 | 1/2006 | Mazzocchi et al. | |
| 6,994,092 B2 | 2/2006 | van der Burg et al. | |
| 6,994,717 B2 | 2/2006 | Konya et al. | |
| 7,011,671 B2 | 3/2006 | Welch | |
| 7,018,401 B1 | 3/2006 | Hyodoh et al. | |
| 7,029,487 B2 | 4/2006 | Greene, Jr. et al. | |
| 7,033,375 B2 | 4/2006 | Mazzocchi et al. | |
| 7,048,752 B2 | 5/2006 | Mazzocchi et al. | |
| 7,063,679 B2 | 6/2006 | Maguire et al. | |
| 7,070,607 B2 | 7/2006 | Murayama et al. | |
| 7,070,609 B2 | 7/2006 | West | |
| 7,083,632 B2 | 8/2006 | Avellanet et al. | |
| 7,128,073 B1 | 10/2006 | van der Burg et al. | |
| 7,128,736 B1 | 10/2006 | Abrams et al. | |
| 7,169,177 B2 | 1/2007 | Obara | |
| 7,195,636 B2 | 3/2007 | Avellanet et al. | |
| 7,211,109 B2 | 5/2007 | Thompson | |
| 7,229,461 B2 | 6/2007 | Chin et al. | |
| 7,232,461 B2* | 6/2007 | Ramer | 623/1.28 |
| 7,244,267 B2 | 7/2007 | Huter et al. | |
| 7,261,720 B2 | 8/2007 | Stevens et al. | |
| 7,303,571 B2 | 12/2007 | Makower et al. | |
| 7,306,622 B2 | 12/2007 | Jones et al. | |
| 7,331,980 B2 | 2/2008 | Dubrul et al. | |
| 7,367,985 B2 | 5/2008 | Mazzocchi et al. | |
| 7,367,986 B2 | 5/2008 | Mazzocchi et al. | |
| 7,371,250 B2 | 5/2008 | Mazzocchi et al. | |
| 7,393,358 B2 | 7/2008 | Malewicz | |
| 7,404,820 B2 | 7/2008 | Mazzocchi et al. | |
| 7,410,482 B2 | 8/2008 | Murphy et al. | |
| 7,410,492 B2 | 8/2008 | Mazzocchi et al. | |
| 7,413,622 B2 | 8/2008 | Peterson | |
| 7,419,503 B2 | 9/2008 | Pulnev et al. | |
| 7,442,200 B2 | 10/2008 | Mazzocchi et al. | |
| 7,485,088 B2 | 2/2009 | Murphy et al. | |
| 7,556,635 B2 | 7/2009 | Mazzocchi et al. | |
| 7,566,338 B2 | 7/2009 | Mazzocchi et al. | |
| 7,569,066 B2 | 8/2009 | Gerberding et al. | |
| 7,572,273 B2 | 8/2009 | Mazzocchi et al. | |
| 7,572,288 B2 | 8/2009 | Cox | |
| 7,575,590 B2 | 8/2009 | Watson | |
| 7,597,704 B2 | 10/2009 | Frazier et al. | |
| 7,608,088 B2 | 10/2009 | Jones et al. | |
| 7,621,928 B2 | 11/2009 | Thramann et al. | |
| 7,632,296 B2 | 12/2009 | Malewicz | |
| 7,670,355 B2 | 3/2010 | Mazzocchi et al. | |
| 7,670,356 B2 | 3/2010 | Mazzocchi et al. | |
| 7,678,130 B2 | 3/2010 | Mazzocchi et al. | |
| 7,682,390 B2 | 3/2010 | Seguin | |
| 7,691,124 B2 | 4/2010 | Balgobin | |
| 7,695,488 B2 | 4/2010 | Berenstein et al. | |
| 7,699,056 B2 | 4/2010 | Tran et al. | |
| 7,727,189 B2 | 6/2010 | VanTassel et al. | |
| 7,744,583 B2 | 6/2010 | Seifert et al. | |
| 7,744,652 B2 | 6/2010 | Morsi | |
| 7,763,011 B2 | 7/2010 | Ortiz et al. | |
| 7,828,815 B2 | 11/2010 | Mazzocchi et al. | |
| 7,828,816 B2 | 11/2010 | Mazzocchi et al. | |
| 7,906,066 B2 | 3/2011 | Wilson et al. | |
| 7,922,732 B2 | 4/2011 | Mazzocchi et al. | |
| 7,955,343 B2 | 6/2011 | Makower et al. | |
| 7,972,359 B2* | 7/2011 | Kreidler | 606/213 |
| 7,993,364 B2 | 8/2011 | Morsi | |
| RE42,758 E | 9/2011 | Ken et al. | |
| 8,016,869 B2 | 9/2011 | Nikolchev | |
| 8,016,872 B2 | 9/2011 | Parker | |
| 8,062,379 B2 | 11/2011 | Morsi | |
| 8,075,585 B2 | 12/2011 | Lee et al. | |
| 8,142,456 B2 | 3/2012 | Rosqueta et al. | |
| 8,202,280 B2 | 6/2012 | Richter | |
| 8,221,445 B2 | 7/2012 | van Tassel et al. | |
| 8,261,648 B1 | 9/2012 | Marchand et al. | |
| 8,298,257 B2 | 10/2012 | Sepetka et al. | |
| 8,430,012 B1 | 4/2013 | Marchand et al. | |
| 8,454,681 B2 | 6/2013 | Holman et al. | |
| 9,179,918 B2 | 11/2015 | Levy et al. | |
| 2001/0000797 A1 | 5/2001 | Mazzocchi | |
| 2001/0007082 A1 | 7/2001 | Dusbabek et al. | |
| 2001/0012949 A1 | 8/2001 | Forber | |
| 2001/0051822 A1 | 12/2001 | Stack et al. | |
| 2002/0013599 A1 | 1/2002 | Limon et al. | |
| 2002/0013618 A1 | 1/2002 | Marotta et al. | |
| 2002/0042628 A1 | 4/2002 | Chin et al. | |
| 2002/0062091 A1 | 5/2002 | Jacobsen et al. | |
| 2002/0111647 A1 | 8/2002 | Khairkhahan et al. | |
| 2002/0165572 A1 | 11/2002 | Saadat | |
| 2002/0169473 A1 | 11/2002 | Sepetka et al. | |
| 2003/0004538 A1 | 1/2003 | Secrest et al. | |
| 2003/0028209 A1 | 2/2003 | Teoh et al. | |
| 2003/0057156 A1 | 3/2003 | Peterson et al. | |
| 2003/0171739 A1 | 9/2003 | Murphy et al. | |
| 2003/0171770 A1 | 9/2003 | Kusleika et al. | |
| 2003/0176884 A1 | 9/2003 | Berrada et al. | |
| 2003/0195553 A1 | 10/2003 | Wallace et al. | |
| 2003/0199913 A1 | 10/2003 | Dubrul et al. | |
| 2003/0199919 A1 | 10/2003 | Palmer et al. | |
| 2004/0015224 A1 | 1/2004 | Armstrong et al. | |
| 2004/0034386 A1 | 2/2004 | Fulton et al. | |
| 2004/0044391 A1 | 3/2004 | Porter | |
| 2004/0098027 A1 | 5/2004 | Teoh et al. | |
| 2004/0098030 A1 | 5/2004 | Makower et al. | |
| 2004/0106945 A1 | 6/2004 | Thramann et al. | |
| 2004/0106977 A1 | 6/2004 | Sullivan et al. | |
| 2004/0111112 A1 | 6/2004 | Hoffmann | |
| 2004/0122467 A1 | 6/2004 | VanTassel et al. | |
| 2004/0122468 A1 | 6/2004 | Yodfat et al. | |
| 2004/0143239 A1 | 7/2004 | Zhou et al. | |
| 2004/0143286 A1 | 7/2004 | Johnson et al. | |
| 2004/0153119 A1 | 8/2004 | Kusleika et al. | |
| 2004/0162606 A1 | 8/2004 | Thompson | |
| 2004/0172056 A1 | 9/2004 | Guterman et al. | |
| 2004/0172121 A1 | 9/2004 | Eidenschink et al. | |
| 2004/0181253 A1 | 9/2004 | Sepetka et al. | |
| 2004/0186562 A1 | 9/2004 | Cox | |
| 2004/0193206 A1 | 9/2004 | Gerberding et al. | |
| 2004/0215229 A1 | 10/2004 | Coyle | |
| 2004/0215332 A1 | 10/2004 | Frid | |
| 2004/0249408 A1 | 12/2004 | Murphy et al. | |
| 2004/0267346 A1 | 12/2004 | Shelso | |
| 2005/0010281 A1 | 1/2005 | Yodfat et al. | |
| 2005/0021077 A1 | 1/2005 | Chin et al. | |
| 2005/0033408 A1 | 2/2005 | Jones et al. | |
| 2005/0033409 A1 | 2/2005 | Burke et al. | |
| 2005/0043759 A1 | 2/2005 | Chanduszko | |

(56) References Cited

U.S. PATENT DOCUMENTS

| | | |
|---|---|---|
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0222605 A1 | 10/2005 | Greenhalgh et al. |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1* | 3/2006 | Guterman et al. ............. 623/1.3 |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0217799 A1 | 9/2006 | Mailander et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von Oepen et al. |
| 2008/0058856 A1* | 3/2008 | Ramaiah et al. ............. 606/198 |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1* | 10/2009 | Riina et al. ................... 606/191 |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1 | 12/2009 | Linder et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0036390 A1 | 2/2010 | Gumm |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1* | 4/2010 | Gerberding et al. ......... 606/213 |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0222802 A1 | 9/2010 | Gillespie, Jr. et al. |
| 2010/0249894 A1 | 9/2010 | Oba et al. |
| 2010/0256667 A1 | 10/2010 | Ashby et al. |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |

(56) References Cited

U.S. PATENT DOCUMENTS

| | | |
|---|---|---|
| 2012/0143237 A1 | 6/2012 | cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2015/0157331 A1 | 6/2015 | Levy et al. |
| 2015/0245932 A1 | 9/2015 | Molaei et al. |

FOREIGN PATENT DOCUMENTS

| | | |
|---|---|---|
| DE | 1283434 B | 11/1968 |
| DE | 102008028308 | 4/2009 |
| DE | 102010050569 A1 | 5/2012 |
| DE | 102011011510 A1 | 8/2012 |
| EP | 743047 A2 | 11/1996 |
| EP | 775470 | 5/1997 |
| EP | 855170 A2 | 7/1998 |
| EP | 1621148 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 | 1/1996 |
| WO | WO-97/26939 | 7/1997 |
| WO | WO-99/03404 | 1/1999 |
| WO | WO 99/05977 | 2/1999 |
| WO | WO-99/08607 | 2/1999 |
| WO | WO 99/08743 | 2/1999 |
| WO | WO-99/40873 A1 | 8/1999 |
| WO | WO-99/62432 | 12/1999 |
| WO | WO-00/57815 A1 | 10/2000 |
| WO | WO 01/93782 | 12/2001 |
| WO | WO 02/00139 | 1/2002 |
| WO | WO-02/071977 A2 | 9/2002 |
| WO | WO-03/037191 A1 | 5/2003 |
| WO | WO-2005/117718 | 12/2005 |
| WO | WO-2006/026744 | 3/2006 |
| WO | WO-2006/034166 A2 | 3/2006 |
| WO | WO-2006/052322 A2 | 5/2006 |
| WO | WO-2006/091891 A2 | 8/2006 |
| WO | WO-2006/119422 A2 | 11/2006 |
| WO | WO-2007/047851 A2 | 4/2007 |
| WO | WO 2007/076480 | 7/2007 |
| WO | WO-2007/095031 A2 | 8/2007 |
| WO | WO-2007/121405 | 10/2007 |
| WO | WO 2008/022327 | 2/2008 |
| WO | WO-2008/109228 A2 | 9/2008 |
| WO | WO 2008/151204 * | 12/2008 |
| WO | WO 2008/151204 A1 | 12/2008 |
| WO | WO-2008/157507 A2 | 12/2008 |
| WO | WO 2009/076515 A1 | 6/2009 |
| WO | WO-2009/132045 A2 | 10/2009 |
| WO | WO-2009/134337 | 11/2009 |
| WO | WO-2009135166 A2 | 11/2009 |
| WO | WO-2010/028314 | 3/2010 |
| WO | WO-2010/030991 | 3/2010 |
| WO | WO-2010/147808 A1 | 12/2010 |
| WO | WO-2011/057002 A2 | 5/2011 |
| WO | WO-2011/057277 A2 | 5/2011 |
| WO | WO-2011/130081 | 10/2011 |
| WO | WO-2011/153304 | 12/2011 |
| WO | WO-2012/068175 A2 | 5/2012 |
| WO | WO-2012/112749 A2 | 8/2012 |
| WO | WO-2012/166804 A1 | 12/2012 |

OTHER PUBLICATIONS

International Search Report and Written Opinion for International Application No. PCT/US2009/051316, mailed on Nov. 23, 2009, in 17 pages.
Notification Concerning Transmittal of International Preliminary Report on Patentability for International Application No. PCT/US2009/051316; dated Feb. 3, 2011.
Hill, et al., "Initial Results of the AMPLATZER Vascular Plug in the Treatment of Congenital Heart Disease, Business Briefing," US Cardiology 2004.
Ronnen, "AMPLATZER Vascular Plug Case Study, Closure of Arteriovenous Fistula Between Deep Femoral Artery and Superficial Femoral Vein," AGA Medical Corporation, May 2007.
U.S. Appl. No. 13/629,678, filed Sep. 28, 2012.
International Search Report and Written Opinion dated Apr. 12, 2011 for International Application No. PCT/US 11/23054.
Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.
International Search Report and Written Opinion dated May 5, 2011 in International Application No. PCT/US 11/23058.
U.S. Appl. No. 13/669,652, filed Nov. 6, 2012.
U.S. Appl. No. 13/826,298, filed Mar. 14, 2013.
U.S. Appl. No. 13/795,556, filed Mar. 12, 2013.
U.S. Appl. No. 13/962,267, filed Aug. 8, 2013.

* cited by examiner

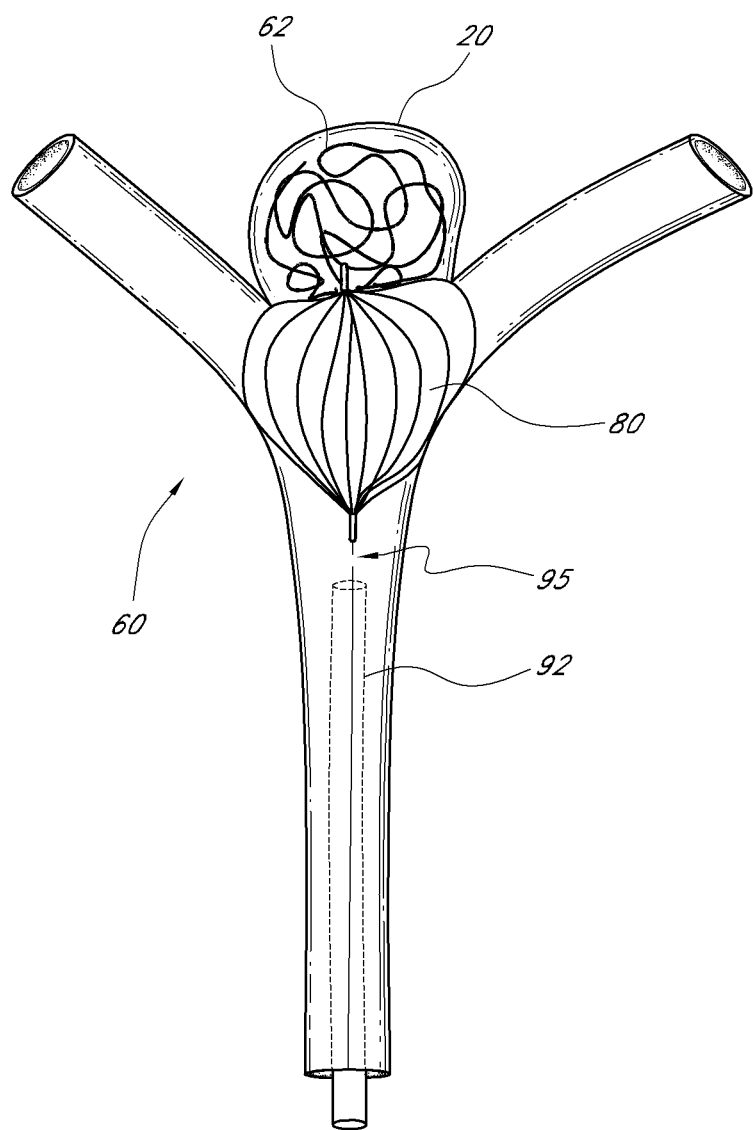
FIG. 9Ciia

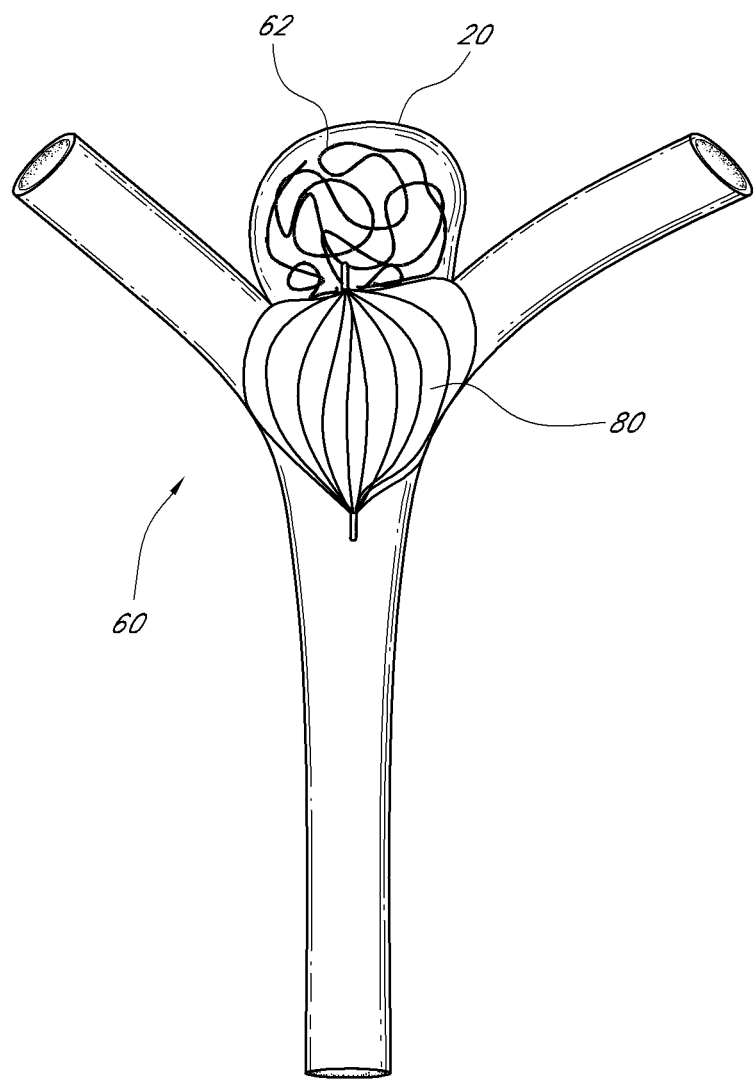
FIG. 9Ciib

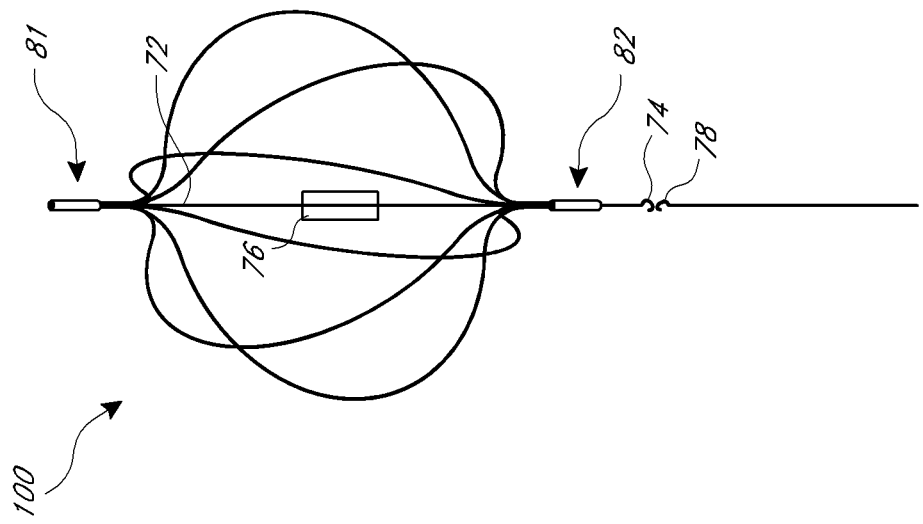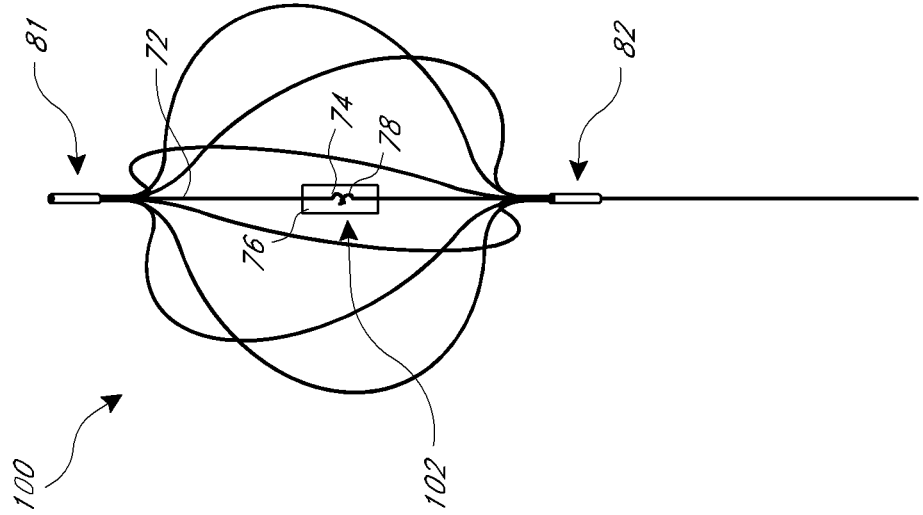

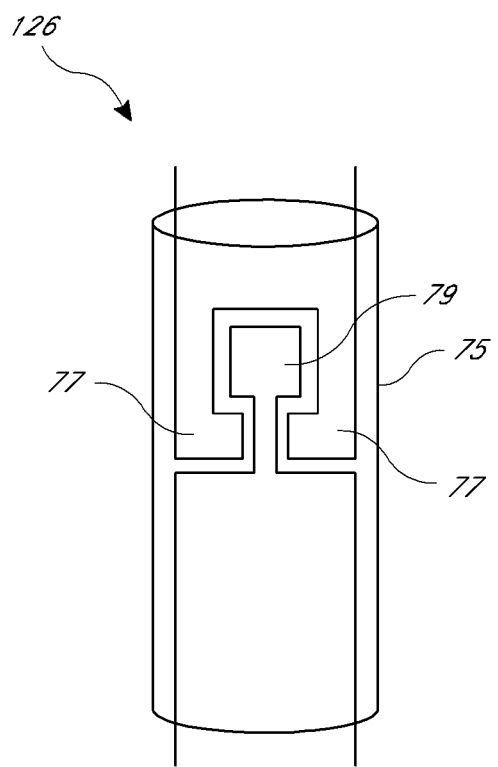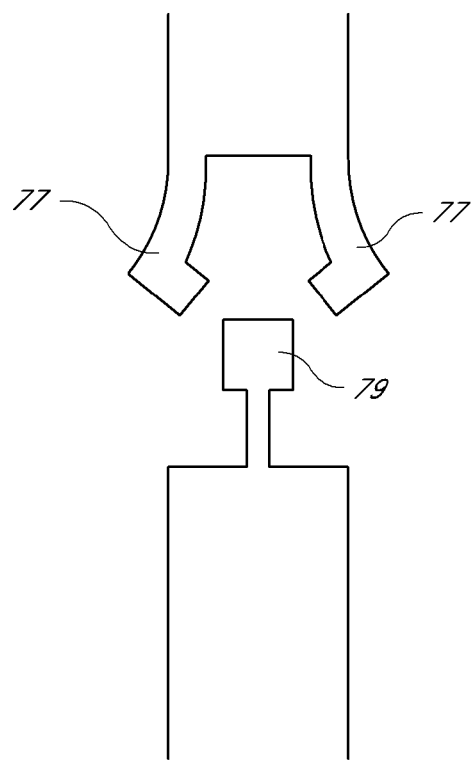
*FIG. 11C*
*FIG. 11D*

VASCULAR REMODELING DEVICE

This application claims priority benefit of U.S. Provisional Patent Application No. 61/299,254, filed Jan. 28, 2010, which is incorporated herein by reference in its entirety.

BACKGROUND

1. Field

The present application generally relates to vascular remodeling devices and to the manner of their positioning in vessels, and, more particularly, to the matter of their positioning at the junction of neurovascular bifurcations having an aneurysm.

2. Description of Related Art

Neurovascular or cerebral aneurysms affect about 5% of the population. Aneurysms may be located, for example, along arterial side walls (e.g., the aneurysm 10 illustrated in FIG. 1) and at arterial bifurcations (e.g., the aneurysm 20 illustrated in FIG. 2). The direction of fluid flow is generally indicated by the arrows 16, 26. The aneurysms 10, 20 each have a fundus 12, 22, a neck 14, 24, and a fundus-to-neck ratio or "neck ratio." If the neck ratio is greater than 2 to 1 or if the neck 14, 24 is less than 4 mm, the aneurysm 10, may be treated with embolization coils alone because the coils will generally constrain themselves within the aneurysm 10, 20 without herniating into parent vessels. If the neck ratio is less than 2 to 1 or if the neck 14, 24 is greater than 4 mm, the aneurysms 10, 20 may be difficult to treat with embolization coils alone because the coils may be prone to herniating into parent vessels, as illustrated in FIGS. 3A and 3B. Herniation of coils may cause arterial occlusion, stroke, and/or death. Compared to the bifurcation illustrated in FIG. 2, the efferent vessels of the bifurcation may be at substantially different angles, have substantially different sizes, and/or be a different quantity (e.g., three or more). Compared to the bifurcation illustrated in FIG. 2, the aneurysm 20 of the bifurcation may be offset with respect to the junction (e.g., having a neck substantially open to one efferent vessel), tilted with respect to a plane created by the vessels (e.g., into or out of the page), etc. Each of these would still be accurately characterized as a "bifurcation" herein.

In order to inhibit such herniation, tubular neck remodeling devices, for example Neuroform™, available from Boston Scientific, and Enterprise™, available from Cordis Neurovascular, may be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not herniate out of the aneurysm. As illustrated in FIG. 4A, tubular remodeling devices 40 are generally useful for side wall aneurysms 10. As illustrated in FIGS. 4B and 4C, tubular remodeling devices 42, 44 are generally less useful for aneurysms 20 at bifurcations, for example because shaping the remodeling devices to preserve blood flow through the afferent and efferent vessels while also inhibiting herniation of coils 28 out of the aneurysm 20 can be difficult.

Another current method used to inhibit herniation of embolization coils used to treat bifurcation aneurysms is balloon-assisted remodeling. In this method, a balloon is inflated at the bifurcation during the embolization process. The inflated balloon covers the neck of the aneurysm, inhibiting coils from herniating out of the aneurysm.

SUMMARY

In some embodiments described herein, an intraluminal apparatus, including a catheter and a vascular remodeling device, is provided. The device is positionable at a junction of afferent and efferent vessels of a bifurcation (e.g., a neurovascular bifurcation) having an aneurysm having a fundus and a neck. Positioning may comprise deployment from a compressed state at least partially inside a catheter to outside the catheter. Positioning may comprise reshaping the device by using a filament (e.g., a central filament) coupled to an end of the device to adjust the distance between the proximal and distal ends and locking the reshaped device into shape. After initial deployment, the device may be retracted into the catheter and then redeployed to achieve different shape or positioning. During deployment, the device may self-expand to conform to the junction. The device may lock into place across the arterial ostia and the neck of the aneurysm. Once the device is positioned at the junction, it may be optionally mechanically, electrolytically, or chemically released from the catheter. After positioning the device at the junction, the device acts as a scaffolding to inhibit or prevent herniation or prolapse of objects such as embolization coils and thrombi out of the neck of the aneurysm. Embolic material may be inserted in the fundus of the aneurysm before or after positioning the device, and before or after optional release of the device from the catheter. After positioning the device at the junction, the device permits perfusion of fluid (e.g., blood) to the efferent vessels. The device may then be retracted into the catheter and withdrawn from the vasculature. The device may have a proximal end, a distal end, and a plurality of filaments extending between and coupled at the proximal end and at the distal end. Certain such devices may be football shaped, pumpkin shaped, twisted, or acorn shaped. The filaments may comprise materials such as Nitinol, MP35N®, or L605. The filaments may comprise a self-expanding and/or a shape-memory material (e.g., comprising CoCr alloy, etc.). The filaments may comprise a variety of dimensions and geometries (e.g., round, flat, etc.) and may comprise individual wires (e.g., round wires or flat ribbons) or be cut from a tube or a sheet, which are heat set to an expanded position. The composition, quantity, and dimensions of the filaments may be related to the conformability of the device at the junction of a bifurcation. An acorn-shaped device may comprise a distal section of the plurality of filaments that comprises a feature (e.g., a leaf-shaped feature) configured to increase the surface area of the distal section. The device may comprise a distal section of the plurality of filaments that spirals towards the distal end of the device. Distal ends of the filaments may comprise a coating configured to preferentially repel certain material (e.g., liquid embolic material). The device may comprise a filament (e.g., a central filament) that can be used to reshape the device by adjusting a distance between the proximal and distal ends of the device. The device may be locked into its reshaped deployed state (e.g., using a ring proximate to an end of the device that catches on prongs located on the central filament). The distal end of the device may comprise a covering configured to inhibit herniation of embolic material out of the neck of the aneurysm. The covering may comprise materials such as polyester, nylon, polytetraflueoroethylene, polylactic acid, and polyglycolic acid. Radiopaque markers may be placed at one or both ends of the device and/or at least one of the filaments may comprise a radiopaque material (e.g., platinum).

In some embodiments, a method of treating an aneurysm is provided. The aneurysm is at a junction of a bifurcation having an afferent vessel and efferent vessels. The aneurysm has a neck and a fundus. The method comprises advancing a catheter proximate to the junction of the bifurcation. The catheter at least partially contains a device in a compressed state. The device comprises a plurality of filaments extending between the proximal end and the distal end and coupled at the proximal end and at the distal end. The method further comprises deploying the device from at least partially inside the catheter to outside the catheter at the junction of the bifurcation. During deployment, the device self-expands to conform in an expanded state to the junction of the bifurcation. After deployment, and while the proximal end of the device is connected to the catheter, the device acts as a scaffolding to inhibit herniation of objects out of the neck of the aneurysm and permits perfusion of fluid to the efferent vessels. The method further comprises retracting the device at least partially back inside the catheter and withdrawing the catheter and the device.

In some embodiments, an intraluminal apparatus is provided. The intraluminal apparatus comprises a catheter and a device. The device has a distal end and a proximal end and comprises a plurality of filaments extending between the proximal end and the distal end and coupled at the proximal end and at the distal end. The device is configured to self-expand from a compressed state upon deployment from at least partially inside the catheter to outside the catheter to conform in an expanded state to a junction of a bifurcation. The bifurcation has an afferent vessel, efferent vessels, and an aneurysm having a neck and a fundus. The device is configured to act as a scaffolding to inhibit herniation of objects out of the neck of the aneurysm and to permit perfusion of fluid to the efferent vessels while the proximal end of the device is connected to the catheter. The device is retractable from the expanded state at least partially back inside the catheter.

In some embodiments, an intraluminal apparatus is provided. The intraluminal apparatus comprises a catheter and a device having a distal end and a proximal end. The device is configured to self-expand upon deployment from at least partially inside the catheter to outside the catheter. The device is configured to conform in an expanded state to a junction of a bifurcation having an afferent vessel, efferent vessels, and an aneurysm having a neck and a fundus. The distal end of the device comprises a covering configured to act as a scaffolding to inhibit herniation of embolic material out of the neck of the aneurysm. The device is configured to permit perfusion of fluid to the efferent vessels.

In some embodiments, a method of treating an aneurysm at a junction of a bifurcation is provided. The bifurcation has an afferent vessel, efferent vessels, and an aneurysm having a neck and a fundus. The method comprises advancing a catheter proximate to the junction of the bifurcation. The catheter at least partially contains a device in a compressed state. The device comprises a plurality of filaments and a central filament. The method further comprises deploying the device from at least partially inside the catheter to outside the catheter at the junction of the bifurcation. During deployment, the device self-expands to conform to the junction of the bifurcation. The method further comprises reshaping the deployed device by using the central filament to adjust a distance between a proximal end of the device and a distal end of the device. After deployment, the device acts as a scaffolding to inhibit herniation of objects out of the neck of the aneurysm and permits perfusion of fluid to the efferent vessels. The method further comprises retracting the device at least partially back inside the catheter and withdrawing the catheter and the device.

In some embodiments, an intraluminal apparatus is provided. The intraluminal apparatus comprises a catheter and a device having a proximal end connected to the catheter and a distal end. The device comprises a plurality of filaments extending between the proximal end and the distal end and coupled at the proximal end and at the distal end. The filaments are configured to self-expand upon deployment from inside the catheter to outside the catheter. The filaments are configured to conform in an expanded state to a junction having an afferent vessel, efferent vessels, and an aneurysm having a neck and a fundus. The device further comprises a central filament extending between the proximal end and the distal end. The central filament is configured to reshape the device in the expanded state by adjusting a distance between the distal end and the proximal end. The device is configured to act as a scaffolding to inhibit herniation of objects out of the neck of the aneurysm and to permit perfusion of fluid to the efferent vessels while the proximal end of the device is connected to the catheter.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

FIGS. 10A and 10B illustrate an example embodiment of a mechanical release mechanism.

FIGS. 11A-11D illustrate other example embodiments of mechanical release mechanisms.

DETAILED DESCRIPTION

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Figure 5:
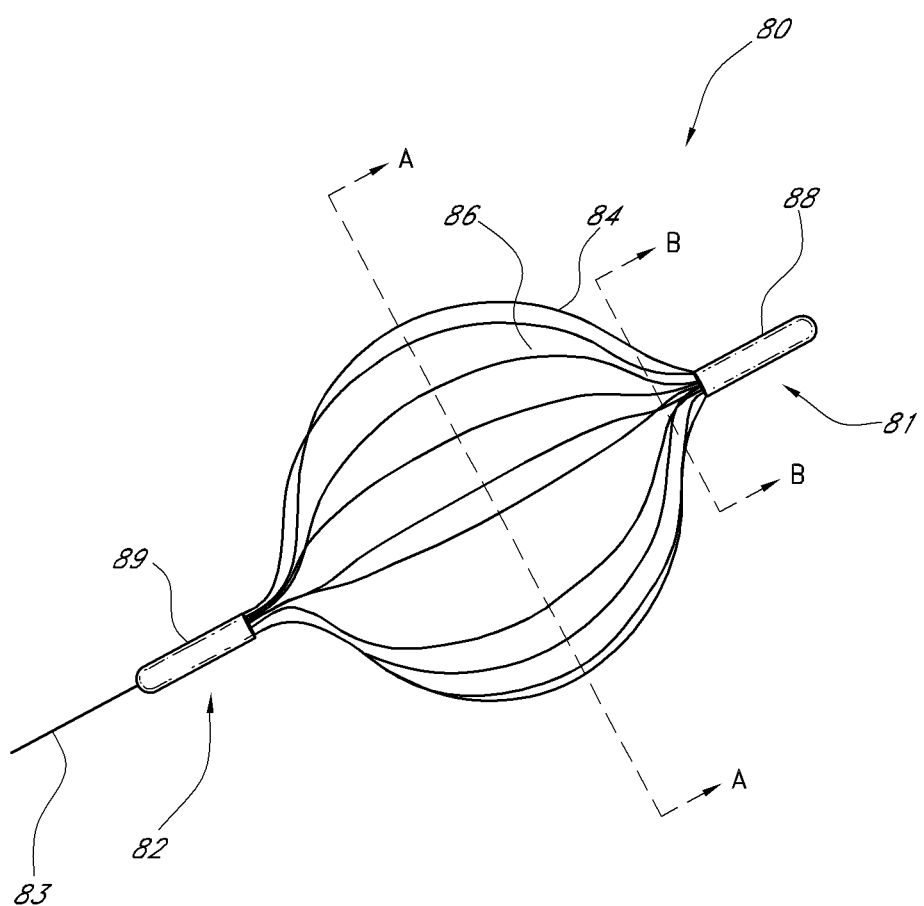
FIG. 5 illustrates an example embodiment of a vascular remodeling device.

FIG. 5 illustrates an example embodiment of a generally spherical vascular remodeling device 80. It will be appreciated that the device 80 may be more compliant than the vasculature in which it is deployed such that it may be somewhat misshapen (e.g., non-spherical, for example as illustrated in FIG. 9B) after being deployed, and that the phrase "generally spherical" describes the shape of the device 80 when in an expanded (e.g., fully expanded) state outside of vasculature. Additionally, the phrase "generally spherical" distinguishes the device 80, which is generally uniform in each dimension in an expanded state, from tubular devices having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 80 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm. Embodiments in which the length is greater than the width may be advantageous for positioning a portion of the device 80 in a portion of the aneurysm 20 (e.g., to aid in embolization).

The device 80 comprises a first or distal end 81 and a second or proximal end 82 substantially opposite the first end 81. The device 80 further comprises a plurality of filaments 84 extending between the distal end 81 and the proximal end 82. The distal end 81 extends outwardly and the proximal end 82 extends outwardly to form a generally spherical (e.g., oval or oblong) shape similar to a football, a rugby ball, or a watermelon. In certain embodiments, the filaments 84 are coupled at the distal end 81 and/or the proximal end 82 (e.g., by adhering, welding, soldering, combinations thereof, and the like). In some embodiments, the device 80 is connected to a catheter (e.g., the catheter 92 described herein) at the proximal end 82 of the device 80. In the embodiment illustrated in FIG. 5, the device 80 comprises a lead or tail 83, which may be used for releasing and/or retracting the device 80 after deployment, as described herein. In some embodiments, the device 80 is connected to a catheter (e.g., the catheter 92 described herein) at the lead or tail 83 of the device 80. In certain embodiments, the device 80 comprises a cut metallic sphere, a single filament (e.g., wrapped back and forth between the first and second ends), etc.

In certain embodiments, the device 80 is configured to be positioned at a junction of a bifurcation (e.g., a neurovascular bifurcation) comprising at least one afferent vessel, efferent vessels, and an aneurysm 20 having a fundus and a neck. For example, in some embodiments, the device 80 is suitably dimensioned to fit in a junction of a bifurcation (e.g., having a diameter between about 2 mm and about 12 mm, having a diameter between about 6 mm and about 8 mm, having a diameter less than about 12 mm, having a diameter greater than about 2 mm). For another example, in some embodiments, the device 80 is less rigid than a junction of a bifurcation (e.g., due to the number of filaments 84, the material of the filaments 84, the thickness of the filaments 84, the spacing of the filaments 84, the shape of the filaments 84, combinations thereof, and the like). In certain embodiments, the device 80 is configured to act as a scaffolding to inhibit or prevent herniation or prolapse of objects (e.g., embolization coils, embolic fluid, thrombi, etc.) out of a neck of an aneurysm 20. For example, in some embodiments, the filaments 84 are dense enough at or proximate to the neck of the aneurysm 20 that objects generally cannot pass. In certain embodiments, the device 80 is configured to permit perfusion of fluid (e.g., blood) to efferent vessels of a bifurcation.

In some embodiments, at least one of the filaments 84 comprises a self-expanding and/or a shape-memory material (e.g., comprising Nitinol, CoCr alloy, MP35N®, L605, etc.), thereby causing the device 80 to be self-expanding under certain conditions (e.g., not restrained by a catheter). In some embodiments, at least one of the filaments 84 comprises a different material than others of the filaments 84 (e.g., some filaments 84 comprising Nitinol and some filaments 84 comprising Nitinol and platinum). In some embodiments, at least one of the filaments 84 comprises a radiopaque material (e.g., platinum). In certain such embodiments, an even number of filaments 84 (e.g., two, four, etc.) comprises a radiopaque material (e.g., platinum). In some embodiments, at least one of the filaments 84 comprises a radiopaque material (e.g., platinum) at least partially wrapped (e.g., coiled) around a self-expanding material (e.g., Nitinol). In some embodiments, at least one of the filaments 84 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, inter alia, on price, desired level of radiopacity, mechanical properties of the radiopaque material, and corrosion properties of the radiopaque material. In certain embodiments, the filaments 84 have a substantially circular or ovoid cross section (e.g., embodiments, in which the filaments 84 comprise separate wires). In some embodiments, the filaments 84 have a substantially rectangular or flat cross section (e.g., embodiments, in which the filaments 84 comprise uncut portions of a metallic tube, as described below, or ribbons). Other shapes of filaments 84 and combinations of shapes of filaments 84 are also possible. In certain embodiments, the plurality of filaments 84 comprises between about six and about twelve filaments 84. In certain embodiments, the plurality of filaments 84 comprises at least about six filaments 84, at least about eight filaments 84, or at least about twelve filaments 84. Other numbers of filaments 84 are also possible.

The device 80 comprises a plurality of perforations or cells 86 between the filaments 84. In some embodiments, a percentage of the outer surface of the device 80 or a portion thereof (e.g., approximately at the line B-B in FIG. 5) covered by the filaments 84 is greater than or equal to about 3%. In some embodiments, a percentage of the outer surface of the device 80 or a portion thereof (e.g., approximately at the line B-B in FIG. 5) covered by the filaments 84 is between about 3% and about 15% (e.g., about 5%). In some embodiments, a percentage of the outer surface of the device 80 or a portion thereof (e.g., approximately at the line B-B in FIG. 5) covered by the filaments 84 is between about 3% and about 25%. In some embodiments, a percentage of the outer surface of the device 80 or a portion thereof (e.g., approximately at the line B-B in FIG. 5) covered by the cells 86 is less than or equal to about 97%. In some embodiments, a percentage of the outer surface of the device 80 or a portion thereof (e.g., approximately at the line B-B in FIG. 5) covered by the cells 86 is between about 85% and about 97% (e.g., about 95%). In some embodiments, a percentage of the outer surface of the device 80 or a portion thereof (e.g., approximately at the line B-B in FIG. 5) covered by the cells 86 is between about 75% and about 97%. In certain embodiments, a percentage of the outer surface of the device 80 or a portion thereof (e.g., approximately at the line B-B in FIG. 5) covered by the filaments 84 is between about 25% and about 40%. In certain embodiments, a percentage of the outer surface of the device 80 or a portion thereof (e.g., approximately at the line B-B in FIG. 5) covered by the cells 86 is between about 60% and about 75%. Other porosities are also possible. In some embodiments, porosity distally increases between the proximal end 82 and an approximate midpoint (e.g., approximately at the line A-A in FIG. 5) and distally decreases between the approximate midpoint and the distal end 81. For example, cross-sections taken along the lines A-A and B-B in FIG. 5 each have the same number of filaments 84, but at the cross-section A-A the filaments 84 are spaced further apart from each other than at the cross-section B-B. As an example, if the device comprises ten filaments 84 each having a thickness of 0.5 mm, the porosity at the cross-section A-A would be about 80% with an example circumference of about 25 mm:

$$100\% \times [1-(\approx 0.5 \text{ mm/filament} \times 10 \text{ filaments}/\approx 25 \text{ mm})] \approx 80\%$$

and the porosity at the cross-section B-B would be about 33% with an example circumference of about 7.5 mm:

$$100\% \times [1-(\approx 0.5 \text{ mm/filament} \times 10 \text{ filaments}/\approx 7.5 \text{ mm})] \approx 33\%.$$

High porosity proximate to a midpoint of the device 80 may provide good fluid flow to efferent vessels. Low porosity proximate to the distal end 81 of the device 80 may provide good scaffolding properties.

In some embodiments, the device 80 comprises a radiopaque marker 88 proximate to the distal end 81 and/or a radiopaque marker 89 proximate to the proximal end 82. In certain embodiments, the radiopaque marker 88 may extend at least partially into the aneurysm 20 when the device 80 is positioned at the junction of a bifurcation. In some embodiments, the radiopaque markers 88, 89 may comprise a sleeve positioned or wrapped around the filaments 84, thereby coupling the filaments 84. The radiopaque markers 88, 89 may aid in positioning the device 80 at the junction of a bifurcation.

In certain embodiments, the device 80 is configured to be highly conformable to the junction of a bifurcation (e.g., a neurovascular bifurcation) comprising at least one afferent vessel, efferent vessels, and an aneurysm 20 having a fundus and a neck. For example, in certain such embodiments, the remodeling device 80 comprises filaments 84 comprising a material and having a thickness and cross-sectional shape that conforms to and allows good compliance with the vasculature at the junction of the bifurcation.

In some embodiments, at least one filament 84 of the plurality of filaments 84 comprises a round wire (e.g., having a circular cross-section). In certain such embodiments, the round wire has a diameter between about 0.002" (approx. 0.05 mm) and about 0.006" (approx. 0.15 mm), between about 0.0025" (approx. 0.05 mm) and about 0.004" (approx. 0.10 mm), or between about 0.003" (approx. 0.08 mm) and about 0.0037" (approx. 0.09 mm). In some embodiments, the round wire comprises an outer sheath comprising a first material and an inner core comprising a second material (e.g., comprising platinum, platinum-tungsten, tantalum, silver, or gold). In some embodiments, the second material of the inner core is radiopaque. In some embodiments, at least one filament 84 comprises a thin wire coiled around a round wire. In certain such embodiments, the thin wire has a diameter between about 0.009" (approx. 0.023 mm) and about 0.002" (approx. 0.051 mm), between about 0.001" (approx. 0.025 mm) and about 0.0175" (approx. 0.044 mm), or between about 0.00125" (approx. 0.032 mm) and about 0.0015" (approx. 0.038 mm). In some embodiments, the thin wire comprises platinum, platinum-tungsten, tantalum, silver, or gold. In some embodiments, the thin wire comprises a radiopaque material.

In certain embodiments, at least one filament 84 of the plurality of filaments 84 comprises a flat wire or ribbon (e.g., having a rectangular cross-section). In certain such embodiments, the flat wire has a thickness between about 0.001" (approx. 0.0025 mm) and about 0.003" (approx. 0.076 mm)

and a width between about 0.003" and about 0.005", a thickness between about 0.0015" (approx. 0.0381 mm) and about 0.0025" (approx. 0.064 mm) and a width between about 0.0035" (approx. 0.089 mm) and about 0.0045" (approx. 0.114 mm), or a thickness between about 0.00175" (approx. 0.044 mm) and about 0.00225" (approx. 0.057 mm) and a width between about 0.00375" (approx. 0.095 mm) and about 0.00425" (approx. 0.108 mm).

In certain embodiments, the device 80 comprises between about 4 filaments 84 and about 12 filaments 84 or between about 6 filaments 84 and about 12 filaments 84. Other numbers of filaments 84 are also possible. In certain embodiments, combinations of different filaments 84 are used in the same device 80 (e.g., 6 filaments comprising Nitinol and 2 round filaments comprising Nitinol and having a thin platinum wire coiled around the two round filaments).

The disclosures of U.S. Provisional Patent Application No. 61/082,579, filed Jul. 22, 2008, and U.S. patent application Ser. No. 12/506,945, filed Jul. 21, 2009, may be relevant to certain of the generally spherical vascular remodeling devices described herein such as the device 80, and the disclosure each of those applications is incorporated herein by reference in its entirety.

Figure 6A:
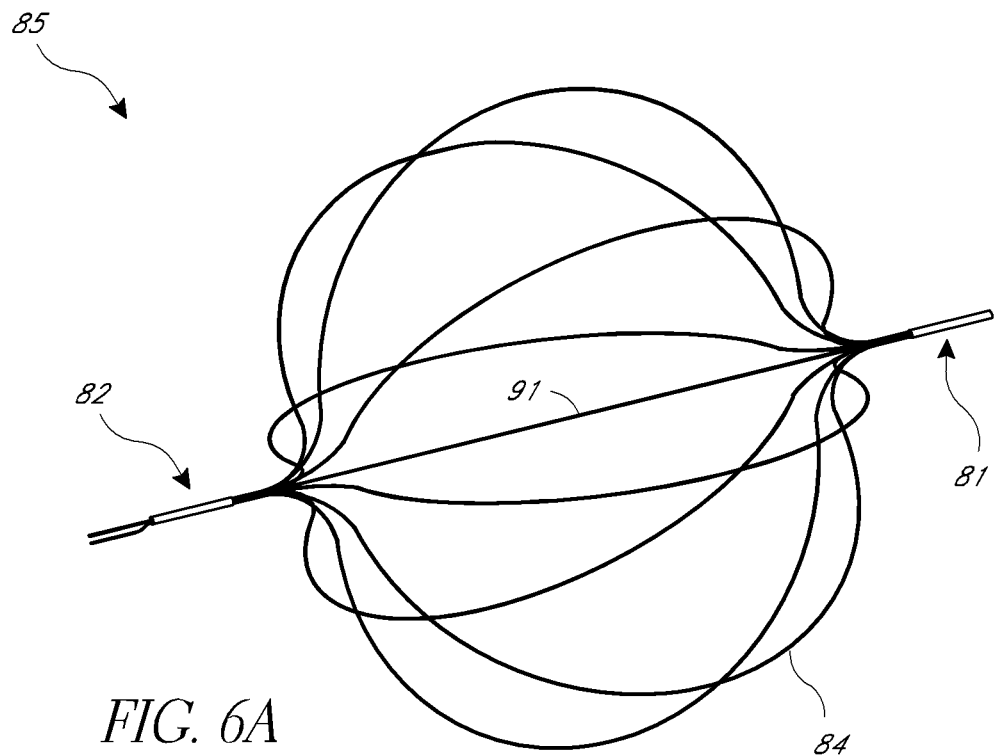
FIGS. 6A and 6B illustrate another example embodiment of a vascular remodeling device.
Figure 6B:
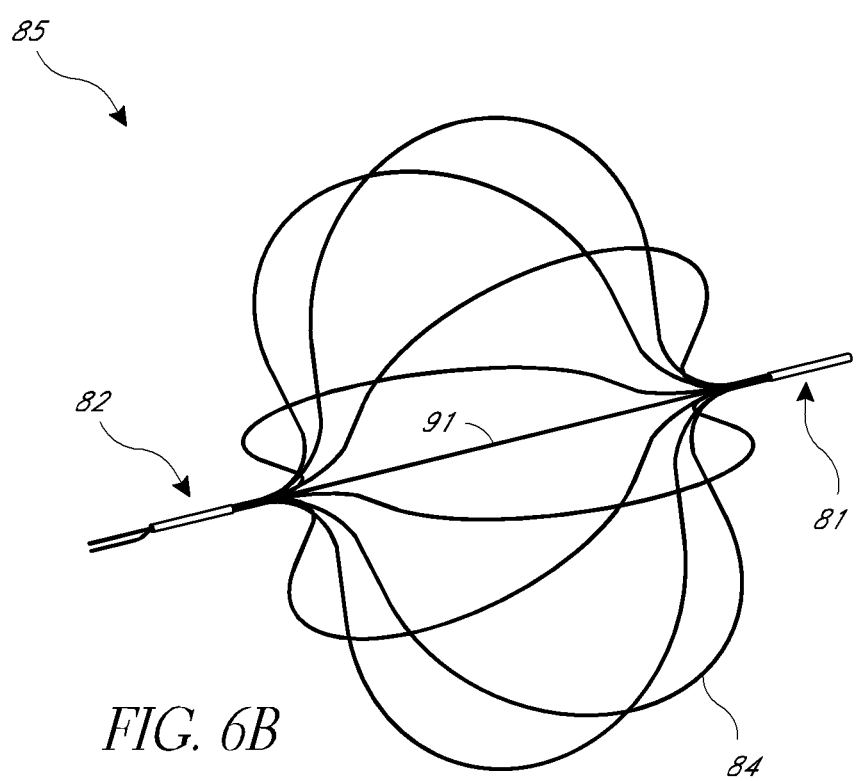

FIGS. 6A and 6B illustrate an example embodiment of a generally spherical vascular remodeling device 85 that is reshapable. In some embodiments, the device 85 comprises a plurality of filaments 84 extending between the second or proximal end 82 and the first or distal end 81 and coupled at the proximal 82 and distal ends 81 and defining a generally spherical shape. In some embodiments, the device 85 and the filaments 84 are configured to conform to a junction of a bifurcation having an afferent vessel, efferent vessels, and an aneurysm 20 having a neck and a fundus. The device 85 may be used during treatment of the aneurysm 20 to act as a scaffolding to inhibit herniation of objects out of the neck of the aneurysm 20 and to permit perfusion of fluid to the efferent vessels. In some embodiments, the device 85 comprises a central filament 91 extending between the proximal end 82 and the distal end 81. The central filament 91 is configured to reshape the device 85 while the device 85 is in an expanded state. In some embodiments, the central filament 91 is rigid (e.g., having a size and/or shape configured to allow pushing and pulling without significant deformation of the central filament).

In some embodiments, the central filament 91 can reshape the device 85 by adjusting the distance between the distal end 81 and the proximal end 82. For example, pulling the central filament 91 (e.g., by manipulating the central filament 91 by action on a proximal portion of the central filament 91 or a mechanism coupled thereto), which is coupled to the distal end 81, can pull the distal end 81 towards the proximal end 82 (e.g., because the proximal end 82 abuts a catheter and/or the ostium of the afferent vessel), thereby squeezing the ends 81, 82 of the device 85 together and changing the shape of the device 85, for example causing radial bulging as depicted in FIG. 6B. For another example, pushing the central filament 91 (e.g., by manipulating the central filament 91 by action on a proximal portion of the central filament 91 or a mechanism coupled thereto), which is coupled to the distal end 81, can push the distal end 81 away from the proximal end 82, thereby lengthening the device 85 and changing the shape of the device 85. In some embodiments, the central filament 91 may act as a guide for reshaping the device 85. For example, the proximal end 82 may be pushed along the central filament 91 towards the distal end 81 (e.g., because the distal end 81 abuts the neck of the aneurysm), thereby squeezing the ends 81, 82 of the device 85 together and changing the shape of the device 85. For another example, the proximal end 82 may be pulled along the central filament 91 away from the distal end 81, thereby lengthening the device 85 and changing the shape of the device 85. In some embodiments, a filament that can be used to reshape the device 85 may be coupled to the proximal end 82 and does not extend through the device 85. For example, pushing the filament (e.g., by manipulating the filament by action on a proximal portion of the filament or a mechanism coupled thereto), which is coupled to the proximal end 82, can push the proximal end 82 towards the distal end 81, thereby squeezing the ends 81, 82 of the device 85 together and changing the shape of the device 85, for example causing radial bulging. For another example, pulling the filament (e.g., by manipulating the filament by action on a proximal portion of the filament or a mechanism coupled thereto), which is coupled to the proximal end 82, can pull the proximal end 82 away from the distal end 81, thereby lengthening the device 85 and changing the shape of the device 85.

Figure 7A:
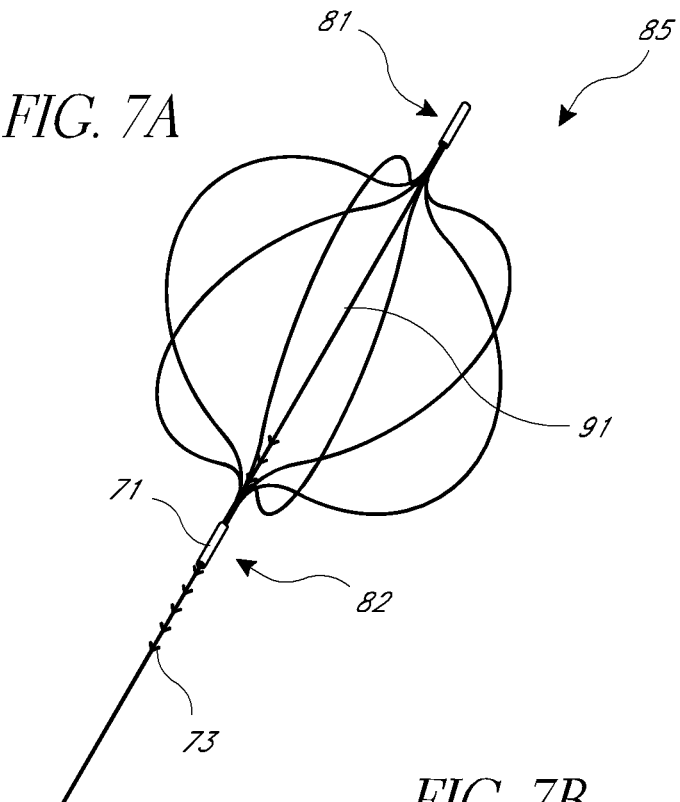
FIGS. 7A and 7B illustrate an example embodiment of reshaping the device of FIGS. 6A and 6B.
Figure 7B:
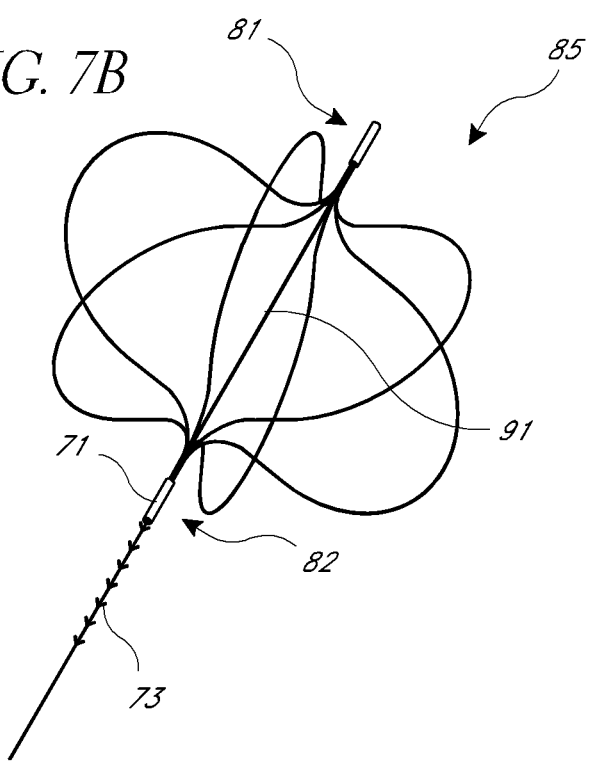

In some embodiments, once the desired shape is achieved, the device 85 may maintain that shape using a locking mechanism. For example, FIGS. 7A and 713 illustrate an example embodiment of a device 85 comprising a central filament 91, prongs 73, and a ring 71 proximate to the proximal end 82. The ring 71 is configured to slice past the prongs 73 as the ring 71 is advanced distally, but to catch on the prongs 73 as the ring 71 is advanced proximally. FIG. 7B depicts the device 85 after the proximal end 82 has been pushed towards the distal end 81, shortening the device 85. In some embodiments, the ring 71 is configured to slide past the prongs 73 as the ring 71 is advanced proximally, but to catch on the prongs 73 as the ring 71 is advanced distally, lengthening the device 85. The ring 73 may be configured to be capable of sliding past the prongs 73 in both the distal and proximal direction, but to catch on the prongs 73 to maintain the reshaped state. In some embodiments, the reshaping capability of the device 85 may advantageously allow the device 85 to be conformable to a junction of a bifurcation. Although illustrated and described as a "central" filament, other arrangements of one or more filaments or other mechanisms may be used to reshape a deployed device.

Figure 8A:
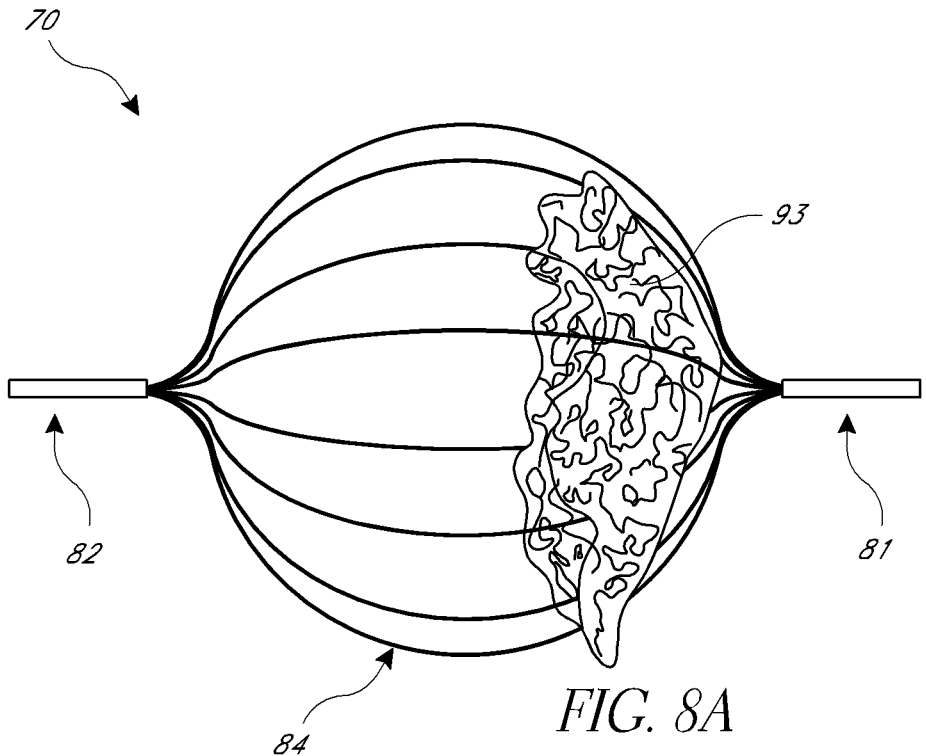
FIGS. 8A and 8B illustrate an example embodiment of another vascular remodeling device.
Figure 8B:
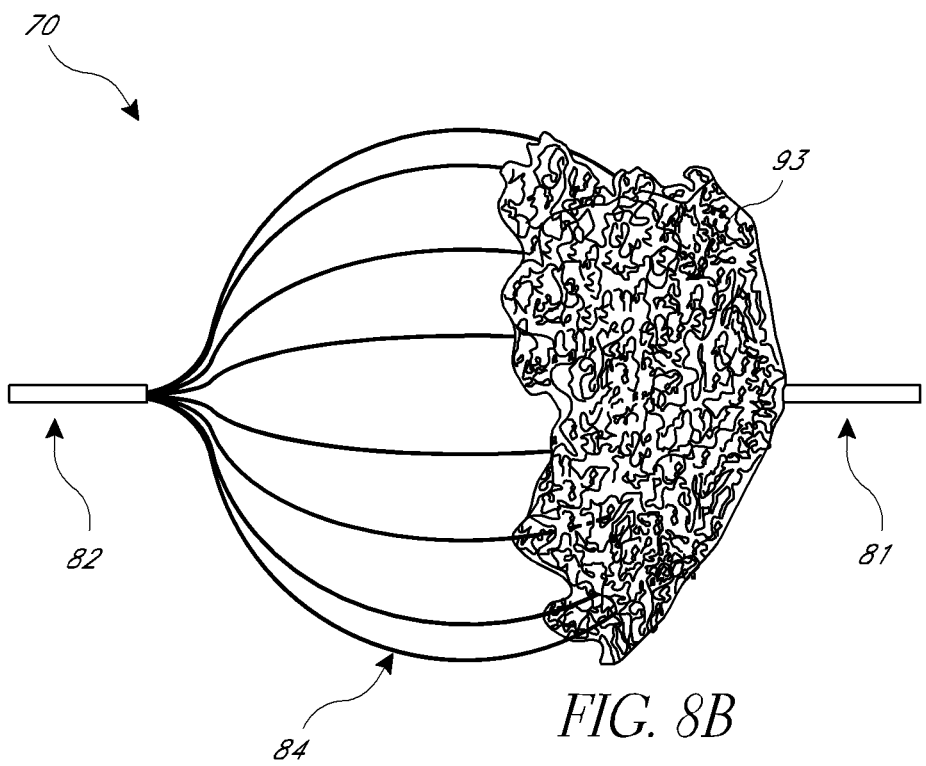

FIGS. 8A and 8B illustrate example embodiments of generally spherical remodeling device 70. In some embodiments, the device 70 has a proximal end 82 and a distal end 81. In some embodiments, the device 70 comprises a plurality of filaments 84 extending between the proximal end 82 and the distal end 81. In some embodiments, the device 70 comprises a covering 93 (e.g., comprising a porous, semi-porous (e.g., as depicted in FIG. 8A), or non-porous (e.g., as depicted in FIG. 8B) material) coupled or attached to the distal end 81. The covering 93 is configured to act as a scaffolding to inhibit herniation of objects out of the neck of the aneurysm 20. In some embodiments, the covering 92 is configured to act as a scaffolding to inhibit herniation of embolic material out of the neck of the aneurysm 20. In some embodiments, the device 70 is configured to conform to a junction of a bifurcation having an afferent vessel, efferent vessels, and an aneurysm 20 having a neck and a fundus. The device 70 is configured to permit perfusion of fluid to the efferent vessels. A catheter may be used to deliver the device 70 in a collapsed state to a location in the vasculature.

In certain embodiments, the covering 93 comprises a polymer (e.g., polyester, nylon, polytetrafluoroethylene (PTFE), combinations thereof, and the like). In some embodiments, the covering 93 comprises a bio-absorbable polymer (e.g., polylactic acid (PLA), polyglycolic acid (PGA), combinations thereof, and the like). Other polymers and materials are possible.

The covering 93 may have varying levels of porosity. In some embodiments, the covering 93 comprises a few polymer filaments sewn together, creating a very porous covering 93. In some embodiments, the covering 93 comprises a semi-porous material (e.g., as depicted in FIG. 8A). For example, the covering 93 may comprise braided polymer filaments or a perforated polymer sheet. In some embodiments, the covering 93 comprises a virtually non-porous material (e.g., as depicted in FIG. 8B).

In certain embodiments, attaching the covering 93 to the device 70 comprises sewing the covering 93 from a preformed thin film. In certain embodiments, attaching the covering 93 to the device 70 comprises mechanical attachment (e.g., wrapped around, looped through, etc.) to the filaments 84. In certain embodiments, attaching the covering 93 to the device 70 comprises depositing (e.g., via physical vapor deposition, chemical vapor deposition, etc.) the covering 93 on the filaments 84. Other portions of the device 70 may also comprise a covering as long as flow between the afferent vessel and the efferent vessels is maintained.

In certain embodiments, attaching the covering 93 to the device 70 comprises forming polymer whiskers on the distal ends of the filaments 84. In certain such embodiments, forming the polymer whiskers comprises chemically treating the distal ends of the filaments 84. After formation of the device 70, the whiskers may be sown, chemically treated, mechanically attached, or coupled in another manner in order to form a porous, semi-porous, or non-porous covering 93.

In some embodiments, the covering 93 and the plurality of filaments 84 together act as a scaffolding to inhibit herniation of objects out of the neck of the aneurysm 20 by reducing the porosity at the distal end 81, thereby further inhibiting or preventing the herniation or prolapse of embolic material from the aneurysm 20.

In certain embodiments, a device 70 comprising a covering 93 on at least a portion of the device 70 can allow the device 70 to comprise fewer filaments 84. For example, in some embodiments in which the device 70 comprises a covering 93, the covering 93 may alone provide suitable scaffolding properties, and the filaments 84 do not need to provide scaffolding properties, thereby allowing the device 70 to comprise fewer filaments 84. A reduced number of filaments 84 may decrease material and manufacturing costs associated with the device 70, for example because the device 70 uses less filament material. A reduced number of filaments may increase the conformability of the device 70 because fewer filaments 84 contain fewer nodes where the filaments 84 contact the vasculature, which can allow for greater flexibility and conformability to the junction of a bifurcation 60 containing an aneurysm 20. A reduced number of filaments can allow the device 70 to be more collapsible and more easily manipulated within the vasculature and delivered to the treatment site.

A remodeling device comprising filaments 84 such as certain embodiments described herein may possess greater conformability at the junction of a bifurcation 60 than balloon remodeling devices, for example those described in U.S. patent application Ser. No. 10/235,064, filed Sep. 4, 2002, and U.S. patent application Ser. No. 11/868,049, filed Oct. 5, 2007, each of which are incorporated herein by reference in its entirety. This greater conformability may occur because a balloon has a continuous surface that generally wholly conforms to a junction, whereas the remodeling devices described herein can conform to the junction only where the filaments 84 contact the vasculature.

A remodeling device comprising filaments 84 such as certain embodiments described herein may reduce damage to vasculature by permitting blood to flow to efferent vessels of a bifurcation 60 throughout a treatment process after a single deployment from a catheter, whereas balloon remodeling devices generally occlude flow to the efferent vessels such that the balloon is periodically deflated in order to restore perfusion, and such repeated inflation and deflation may damage the vasculature.

In certain embodiments, the distal ends of the filaments 84 and/or a covering 93 may comprise a coating configured to preferentially repel certain material. For example, the coating may be configured to preferentially repel liquid embolic material (e.g., Onyx®). In some embodiments, forming such a coating on the distal ends of the filaments 84 comprises chemically treating the filaments 84. Certain such coatings may allow delivery of liquid embolic material through the device 80 while inhibiting, reducing, or preventing permeation of the liquid embolic material from out of the aneurysm through the device 80.

Figure 9A:
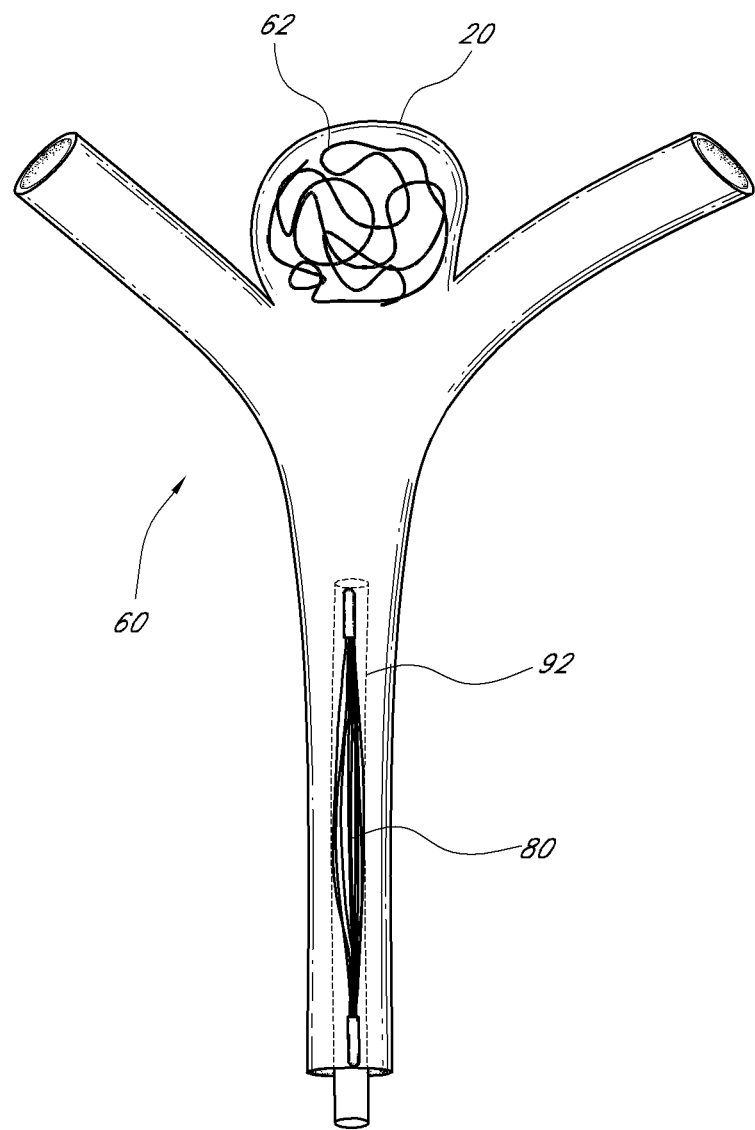
FIGS. 9A-9Ciib illustrate example embodiments of methods for treating an aneurysm using the device of FIG. 5.
Figure 9B:
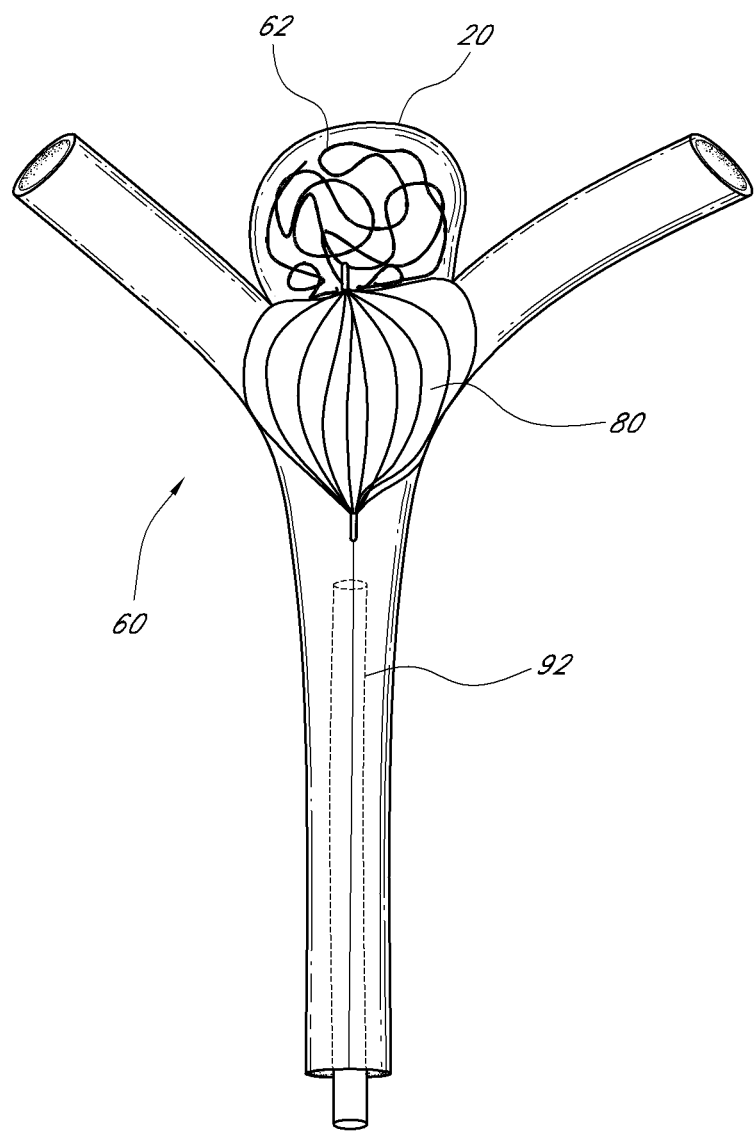
Figure 9C:
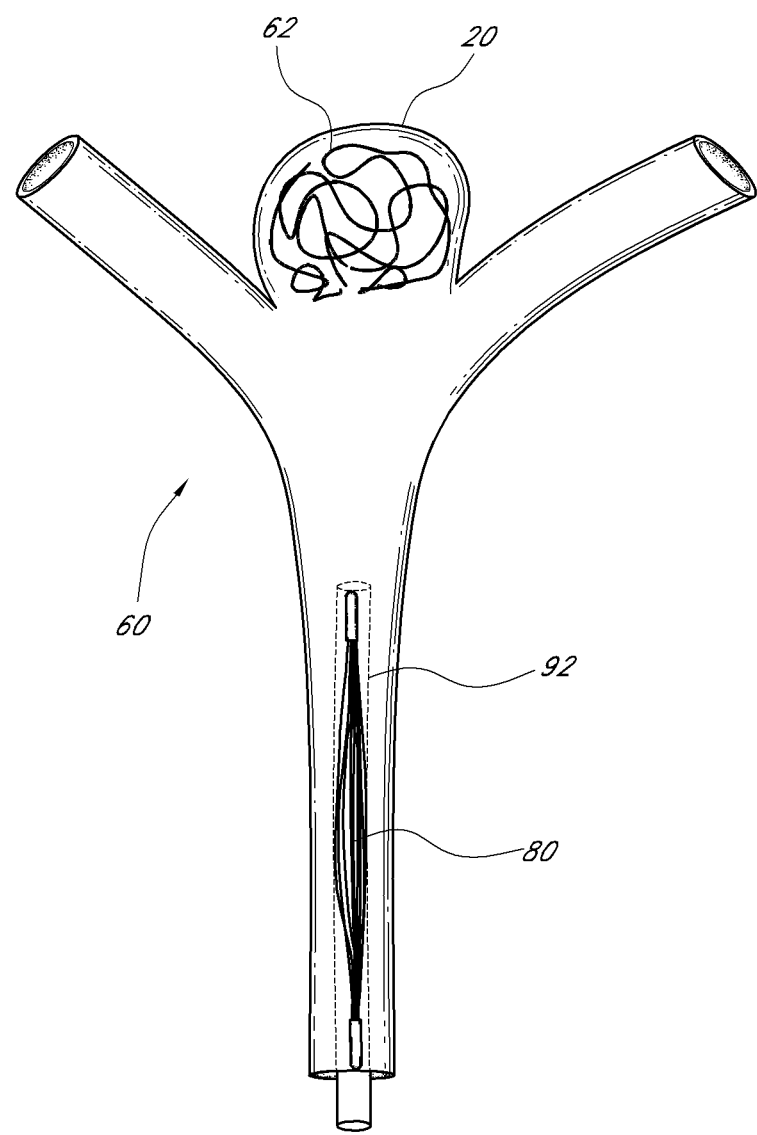

FIGS. 9A-9Ciib illustrate an example embodiment of a method for treating an aneurysm 20 using an apparatus comprising the device 80 and a catheter 92. FIG. 9A illustrates a confluence of afferent and efferent vessels or "junction" at a bifurcation 60 having an aneurysm 20. In some embodiments, the vasculature is neurovascular or cranial. The aneurysm 20 may be treated by inserting material (e.g., embolic coils, embolic liquid) into the aneurysm 20. The aneurysm 20 is illustrated with a plurality of embolization coils 62 having been inserted in the fundus of the aneurysm 20. It will be appreciated that the embolization coils 62 may be a single embolization coil or other embolic material (e.g., Onyx® liquid embolic material). A catheter 92 (e.g., a microcatheter), at least partially containing a constricted or compressed device 80, is also shown in the afferent vessel. The catheter 92 is small enough and flexible enough to be routed through the vasculature and situated proximate to the aneurysm 20 (e.g., as depicted in FIG. 9A). In some embodiments, the embolization coils 62 are inserted in the fundus of the aneurysm 20 using the catheter 92. In some embodiments, the embolization coils 62 are inserted in the fundus of the aneurysm 20 using a different catheter. In certain such embodiments, a guidewire may be used to guide both catheters.

FIG. 9B illustrates the bifurcation 60 after the device 80 has been deployed from the catheter 92 (e.g., by being pushed out with a plunger, by retracting the catheter 92 while the device 80 remains stationary, combinations thereof, and the like) at the junction of the bifurcation 60. After being deployed from the catheter 92, the device 80 may expand. In some embodiments, the device 80 comprises a self-expanding and/or a shape-memory material that automatically expands towards an uncompressed state or expands towards an uncompressed state upon the application of warm fluid (e.g., saline). In some embodiments, the device 80 expands upon being forced radially outwardly by a balloon upon inflation. Other expansion mechanisms are also possible. The device 80 may substantially conform to the shape of the junction of the bifurcation 60 (e.g., not substantially including portions extending into the afferent and efferent vessels) and locks into place across the ostia of the afferent and efferent vessels and the neck of the aneurysm 20. The device 80 at least partially covers the neck of the aneurysm 20 as well as the afferent and efferent vessels, but does not need to divert flow. The device 80 acts as a scaffolding to inhibit or prevent herniation or prolapse of objects such as the embolization coils 62 and/or thrombi out of the aneurysm 20. The device 80 also allows perfusion of fluid (e.g., blood) from the afferent vessel(s) to the efferent vessel(s).

Referring again to FIGS. 6A and 6B, in some embodiments, the device may be optionally reshaped after it has been deployed from the catheter 92 and is in an expanded state, for example to conform to the shape of the junction of the bifurcation 60 or to better conform to the shape of the junction of the bifurcation 60. Referring again to FIGS. 7A and 7B, in some embodiments, the device may be reshaped by advancing or retracting the proximal end 82 of the device along a central filament 91 and using a locking mechanism 71, 73 to lock the device in the reshaped state.

FIG. 9Ci illustrates an embodiment in which the device 80 is withdrawn from the vasculature after the device 80 has been retracted into the catheter 92. In certain such embodiments, after the device 80 performs a function (e.g., inhibiting herniation of objects from the neck of the aneurysm 20) in a deployed state while connected to the catheter 92, the device 80 is retracted into the catheter 92 and the entire apparatus is withdrawn from the vasculature.

In some embodiments, the device 80 may be retracted into the catheter 92 after being deployed from the catheter 92 (e.g., by pulling on a tail). The device 80 may then be redeployed, for example at a new angle, at a new rotational position) more proximal or distal to an afferent vessel and/or an efferent vessel, etc. For example, although the device 80 expands towards an uncompressed state after deployment, the resulting shape of the device 80 at the junction of the bifurcation 60 may vary depending on the details of the deployment from the catheter 92 because the device 80 adapts to the shape of the anatomy (e.g., due to the size, shape, number, etc. of the filaments 84). Once the user is satisfied with properties of the device 80 (e.g., position, tilt, rotation, shape, interaction with the vessels, etc.), the device 80 may optionally be released as described herein.

FIGS. 9Ciia and 9Ciib depict an optional embodiment in which the device 80 is released from the catheter 92 after the deployment illustrated in FIG. 9B or after redeployment. FIG. 9Ciia illustrates releasing the device 80 from the catheter 92 (e.g., by a mechanical, chemical, or electrolytic release mechanism) at a release point 95. FIG. 9Ciib illustrates the device 80 remaining in position at the junction of the bifurcation 60 after the catheter 92 has been withdrawn from the vasculature.

It will be appreciated that the devices described herein (e.g. devices 70, 80, 85, 110, 130, 150, 170, 175, 180) may be used in any of the methods described herein (e.g., the method described with respect to FIGS. 9Ci-9Ciib, the methods described with respect to FIGS. 12A-12D, the methods described the methods described with respect to FIGS. 19A-19D), combinations of the same, or the like.

FIGS. 10A and 10B illustrate a device 100 comprising an example embodiment of a release mechanism 102. The release mechanism 102 comprises a wire 72, hooks 74, 78, and a sleeve 76. The wire 72 extends between the proximal end 82 and the distal end 81 (e.g., through the center of the device 100). In some embodiments, the wire 72 may be the same as the central filament 91 described with respect to the device 85 herein, and it may be possible to change and lock the shape of the device 100. The proximal end of the wire 72 comprises the hook 74. The distal end of the catheter comprises (e.g., is integrally part of, is connected to, etc.) the hook 78. The hook 74 is intertwined with the hook 78 within the sleeve 76. While in the sleeve 76, the hooks 74, 78 cannot be disconnected. FIG. 10B illustrates the device 100 after retracting the sleeve 76 (e.g., by retracting the wire 72) to expose the hooks 74, 78, which allows the hook 74 to disconnect from the hook 78, thereby mechanically releasing the device 100 from the catheter. In some embodiments, the device 100 is mechanically released from the catheter, or a component of the catheter, by disconnecting an interlock holding the catheter to a wire of the device 100 (e.g., a tail).

Figure 11A:
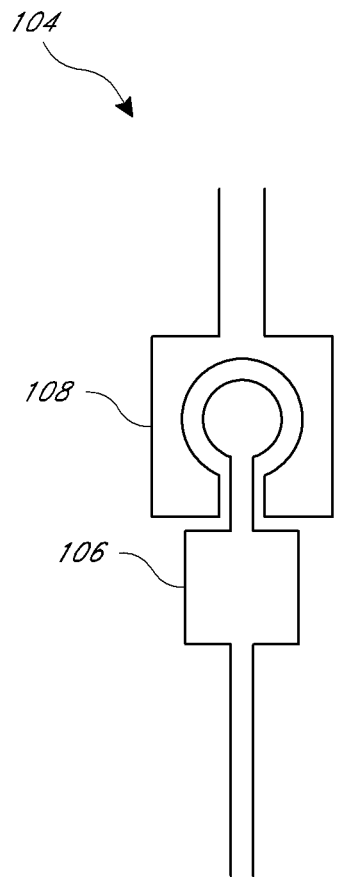
Figure 11B:
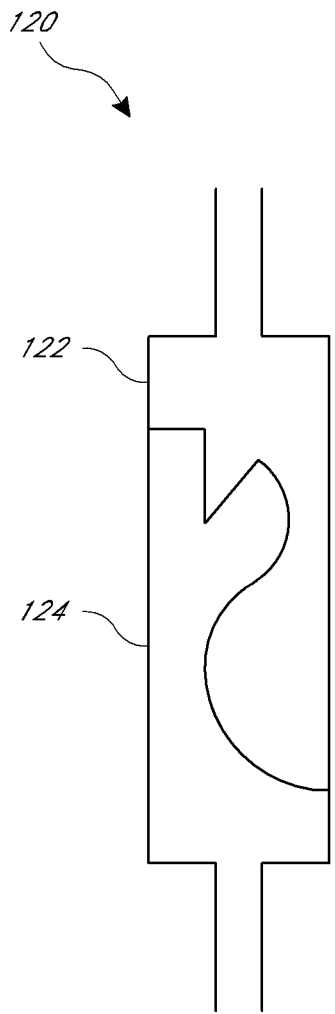

In some embodiments, the interlock comprises a keyway, for example as described in International Application No. PCT/US2007/066722, which is incorporated herein by reference in its entirety, and the device 100 may be optionally released from the catheter, or a component connected to the catheter, by manipulating the keyway. FIG. 11A illustrates an example embodiment of a keyway 104. The keyway 104 comprises a male end 106 and a female end 108. The device 100 may be optionally released from the catheter, or a component connected to the catheter, by manipulating the male and female ends 106, 108 and separating them. In some embodiments the male end 106 is selectively slidable out of the female end 108. In some embodiments, the male and female ends 106, 108 are confined within a sleeve. Upon removal from the sleeve, the male and female ends 106, 108 may be released from one another. The device 100 may comprise the female end 108 and the catheter may comprise the male end 106. Alternatively, the catheter may comprise (e.g., is integrally part of, is connected to, etc.) the female end 108 and the device 100 may comprise the male end 106. FIG. 11B illustrates an example embodiment of a release mechanism 120 comprising a plurality of puzzle pieces 122, 124. The device 100 may be optionally released from the catheter, or a component connected to the catheter, by manipulating the puzzle pieces 122, 124 and separating them. In some embodiments, the puzzle pieces 122, 124 are confined within a sleeve. Upon removal from the sleeve, the puzzle pieces 122, 124 may be released from one another.

FIGS. 11C and 11D illustrate an example embodiment of a release mechanism comprising a pop out mechanism 126. The pop out mechanism 126 comprises a sleeve 75, arms 77, and a bulbous portion 79. The device may be optionally released from the catheter, or a component connected to the catheter, by manipulating the sleeve 75. When the sleeve 75 is in place (FIG. 11C), the arms 77 are held in place around the bulbous portion 79. Once the sleeve 75 is removed (FIG. 11D), the arms 77 are able to expand (e.g., due to self-expanding properties, due to being easily moved by ambient forces, being moved by opposing force of the bulbous portion 79, etc.) and the arms 77 no longer hold the bulbous portion 79 in place. Although illustrated as square features, the arms 77 and the bulbous portion 79 may have any suitable shape. For example, the arms 77 and/or the bulbous portion 79 may include angled features to aid movement of the arms 77 upon application of an opposing force (e.g., acting as a plane to convert longitudinal movement into lateral movement). In some embodiments, the device (e.g., a proximal end of the device, a filament of the device, a central filament of the device, etc.) comprises (e.g., is integrally part of, is connected to, etc.) the arms 77 and the catheter comprises (e.g., is integrally part of, is connected to, etc.) the bulbous portion 79. In some embodiments, the device (e.g., a proximal end of the device, a filament of the device, a central filament of the device, etc.) comprises (e.g., is integrally part of, is connected to, etc.) the bulbous portion 79 and the catheter comprises (e.g., is integrally part of, is connected to, etc.) the arms 77.

Figures 12A, 12B:
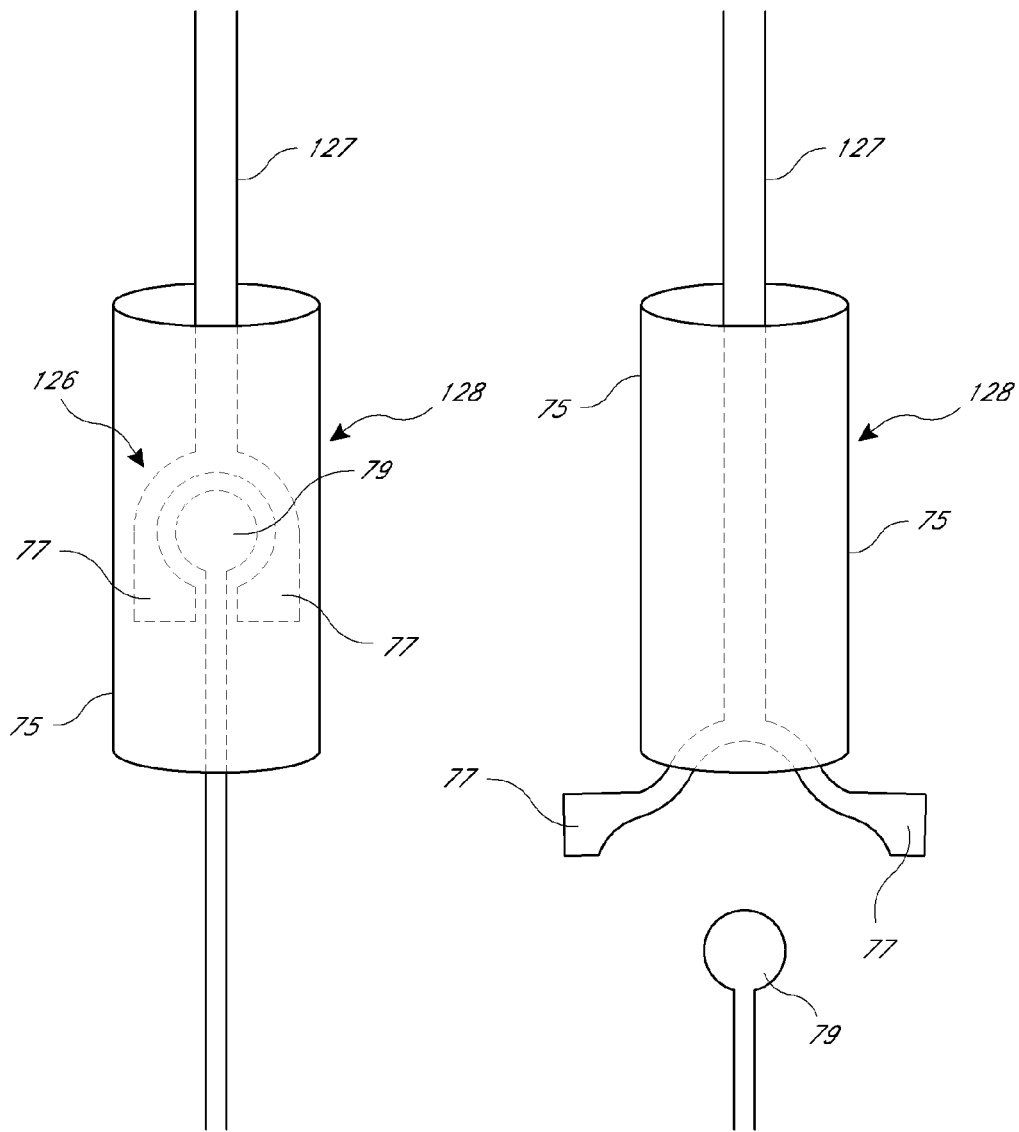
FIGS. 12A and 12B illustrate an example embodiment of a mechanism for releasing and reshaping the device.

FIGS. 12A and 12B depict an embodiment of the pop out mechanism 126 described herein, in which the mechanism 126 may be used to release a device 85 comprising a central filament 127, for example as described with respect to FIGS. 6A and 6B. The pop out mechanism 126 and the central filament 127 may be configured to release the device 85 from the catheter and to lock the device 85 in a reshaped state. In certain such embodiments, the central filament 127 comprises (e.g., is integrally part of, is connected to, etc.) a plurality of outwardly-biased arms 77, the catheter comprises (e.g., is integrally part of, is connected to, etc.) a bulbous portion 79, and the proximal end 128 of the device 85 comprises a sleeve 75. In some embodiments, the sleeve 75 is used to couple the filaments 84 (filaments 84 not shown in FIGS. 12A and 12B) at the proximal end 128 of the device 85. The central filament 127 is slidable within the sleeve 75. In some embodiments, the central filament 127 is only slidable within the sleeve 75 in one direction (e.g., proximally). The sleeve 75 is configured to contain the plurality of arms 77 around the bulbous portion 79 when the central filament 127 is in a first position relative to the sleeve 75 (e.g., FIG. 12A). In some embodiments, the sleeve 75 comprises a substantially uniform tube. In some embodiments, the sleeve 75 comprises a narrow side and an expanded side, for example to limit movement of the contained plurality of arms 77 and bulbous portion 79 (e.g., the narrow side preventing distal movement of the contained plurality of arms 77 and bulbous portion 79). In some embodiments, the sleeve 75 comprises a crimp, for example to limit movement of the contained plurality of arms 77 and bulbous portion 79 (e.g., the crimp preventing distal movement of the contained plurality of arms 77 and bulbous portion 79). The plurality of arms 77 are each configured to outwardly expand (e.g., self-expand to an outwardly expanded state when not confined by the sleeve 75 as a result of being heat set in the outwardly expanded state) to lock into shape the reshaped deployed device 85 and to release the bulbous portion 79 when the central filament 127 is in a second position relative to the sleeve 75 (e.g., FIG. 12B). The second position is proximal to the first position. In some embodiments, the central filament 127 is pulled proximally to release the arms 77 from the sleeve 75. In some embodiments, the proximal end 128 is pushed distally to release the arms 77 from the sleeve 75. The plurality of arms 77 are configured to catch on a proximal end of the sleeve 75, holding the proximally-pulled central filament 127 in place and locking into place the reshaped device 85. In some embodiments, the further the second position is from the first position, the shorter the distance between the proximal end and the distal end of the reshaped device 85.

It will be appreciated that all of the devices described herein (e.g., device 70, 80, 85, 110, 130, 150, 170, 175, 180) may comprise any of the release mechanisms described herein (e.g., the release mechanisms described with respect to FIGS. 10A-12B, combinations of the same, and the like).

Referring again to FIG. 9Ciia, in some embodiments, the device 80 may be optionally released from the catheter 92 electrolytically (e.g., by applying a small current until a portion of a tail proximal to the device 80 corrodes away, as illustrated by the gap 95). The catheter 92 is then withdrawn from the bifurcation 60, thereby leaving or permanently positioning the device 80 at the junction of the bifurcation 60. In some embodiments, the device 80 is optionally released from the catheter 92 chemically (e.g., by dissolving a coating or segment with dimethyl sulfoxide (DMSO) (e.g., as illustrated by the gap 95)).

Figure 13A:
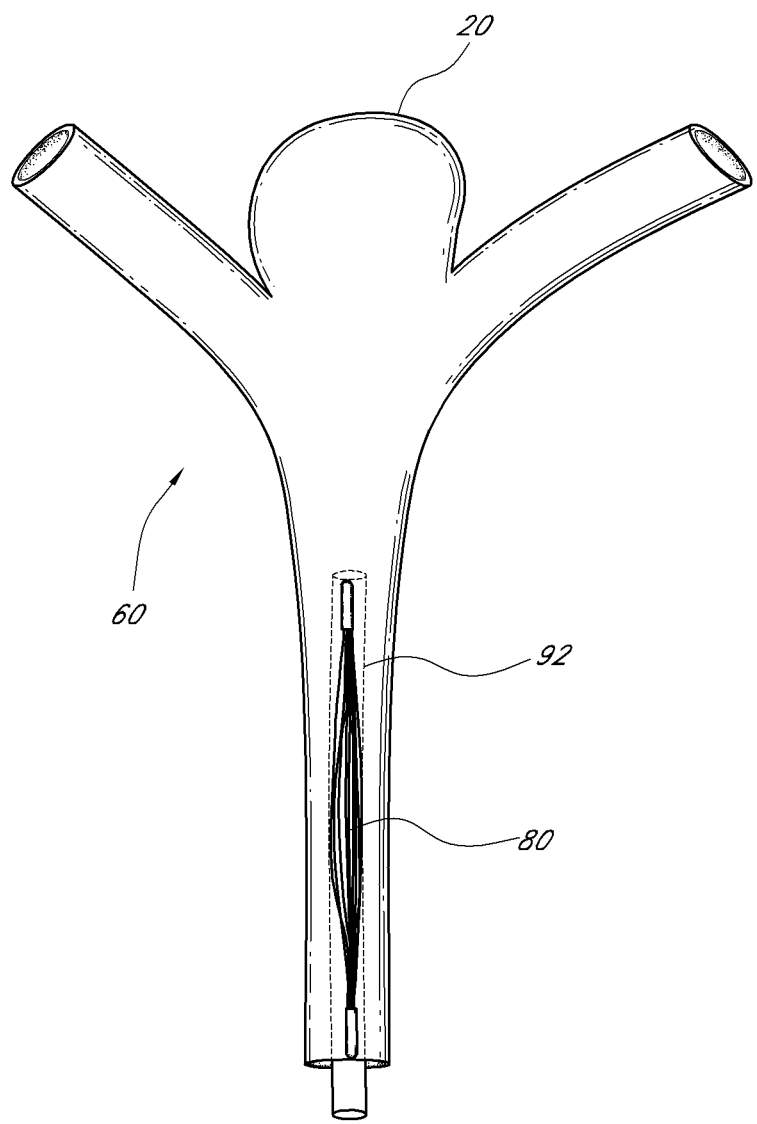
FIGS. 13A-13D illustrate another example embodiment of a method for treating an aneurysm using the device of FIG. 5.

FIGS. 13A-13D illustrate another example embodiment of a method for treating an aneurysm 20 using an apparatus comprising the device 80 and a catheter 92. FIG. 9A illustrates a confluence of afferent and efferent vessels or "junction" at a bifurcation 60 having an aneurysm 20. In some embodiments, the vasculature is neurovascular or cranial. The aneurysm 20 may be treated by inserting material (e.g., embolic coils, embolic liquid) into the aneurysm 20. A catheter 92 (e.g., a microcatheter), at least partially containing a constricted or compressed device 80, is also shown in the afferent vessel. The catheter 92 is small enough and flexible enough to be routed through the vasculature and situated proximate to the aneurysm 20 (e.g., as depicted in FIG. 13A).

Figure 13B:
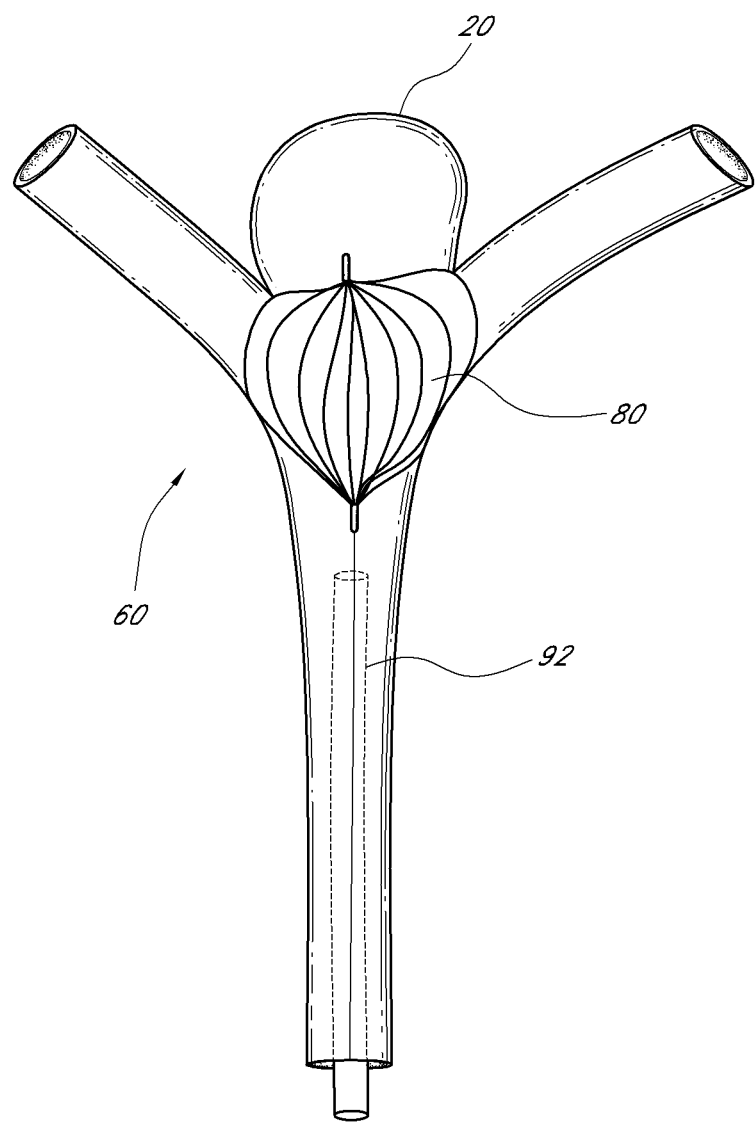

FIG. 13B illustrates the bifurcation 60 after the device 80 has been deployed from the catheter 92 (e.g., by being pushed out with a plunger, by retracting the catheter 92 while the device 80 remains stationary, combinations thereof, and the like) at the junction of the bifurcation 60. After being deployed from the catheter 92, the device 80 may expand. In some embodiments, the device 80 comprises a self-expanding and/or a shape-memory material that automatically expands towards an uncompressed state or expands towards an uncompressed state upon the application of warm fluid (e.g., saline). In some embodiments, the device 80 expands upon being forced radially outwardly by a balloon upon inflation. Other expansion mechanisms are also possible. The device 80 may substantially conform to the shape of the junction of the bifurcation 60 (e.g., not substantially including portions extending into the afferent and efferent vessels) and locks into place across the ostia of the afferent and efferent vessels and the neck of the aneurysm 20. The device 80 at least partially covers the neck of the aneurysm 20 as well as the afferent and efferent vessels, but does not need to divert flow. The device 80 acts as a scaffolding to inhibit or prevent herniation or prolapse of objects such as thrombi out of the aneurysm 20. The device 80 allows perfusion of fluid (e.g., blood) from the afferent vessel(s) to the efferent vessel(s).

As described above with respect to FIG. 9Ci, in some embodiments, the device 80 may be retracted into the catheter 92 after being deployed from the catheter 92 (e.g., by pulling on a tail). The device 80 may then be redeployed, for example at a new angle, at a new rotational position, more proximal or distal to an afferent vessel and/or an efferent vessel, etc. For example, although the device 80 expands towards an uncompressed state after deployment, the resulting shape of the device 80 at the junction of the bifurcation 60 may vary depending on the details of the deployment from the catheter 92 because the device 80 adapts to the shape of the anatomy (e.g., due to the size, shape, number, etc. of the filaments 84). Once the user is satisfied with properties of the device 80 (e.g., position, tilt, rotation, shape, interaction with the vessels, etc.), the device 80 may optionally be released as described herein.

Figure 13C:
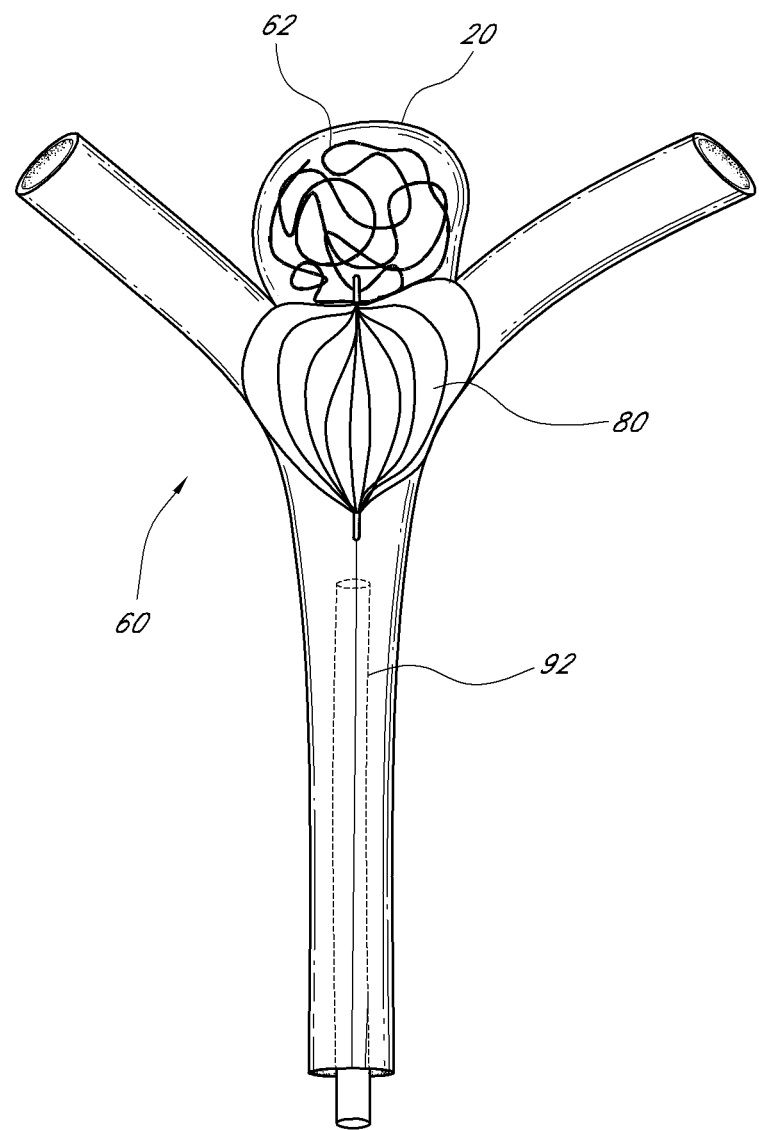

FIG. 13C illustrates the bifurcation 60 after a plurality of embolization coils 62 have been inserted in the fundus of the aneurysm 20. It will be appreciated that the embolization coils 62 may be a single embolization coil or other embolic material (e.g., Onyx® liquid embolic material). In some embodiments, the embolization coils 62 are inserted in the fundus of the aneurysm 20 using the catheter 92. In some embodiments, the embolization coils 62 are inserted in the fundus of the aneurysm 20 using a different catheter. In certain such embodiments, a guidewire may be used to guide both catheters. The device 80 acts as a scaffolding to inhibit or prevent herniation or prolapse of objects such as the embolization coils 62 and/or thrombi out of the aneurysm 20.

Figure 13D:
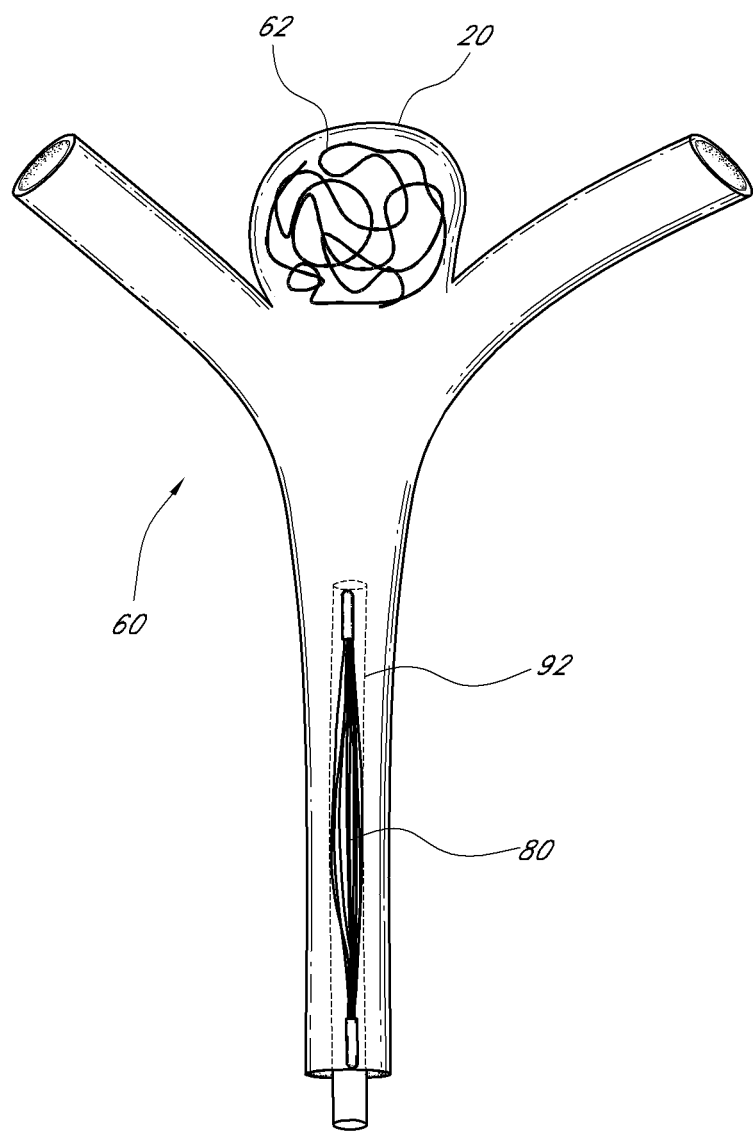

FIG. 13D illustrates the bifurcation 60 after the catheter 92 and the device 80 have been removed. In the embodiment illustrated in FIGS. 13A-13D, the device 80 is connected to the catheter 92 for the total duration of the procedure. Different combinations are also possible. For example, the embolization coils 62 may be inserted in the fundus 22 of the aneurysm 20 after the device 80 has been deployed from the catheter 92, but prior to withdrawal of the apparatus or optional release of the device 80 from the catheter 92. For another example, the embolization coils 62 may be inserted in the fundus of the aneurysm 20 after the device 80 has been deployed from the catheter 92 and after the device 80 has been optionally released from the catheter 92. For another example, the embolization coils 62 may be inserted into the fundus of the aneurysm 20 after the device 80 has been deployed from the catheter 92 (e.g., in a coil state), and the device 80 may be retracted and redeployed from the catheter 92 (e.g., in a final state).

It will be appreciated that the devices described herein (e.g., devices 70, 80, 85, 110, 130, 150, 170, 175, 180) may be used in any of the methods described herein (e.g., the methods described with respect to FIGS. 9Ci-9Ciib, the methods described with respect to FIGS. 13A-13D, the methods described with respect to FIGS. 20A-20D), combinations of the same, or the like.

Figure 14:
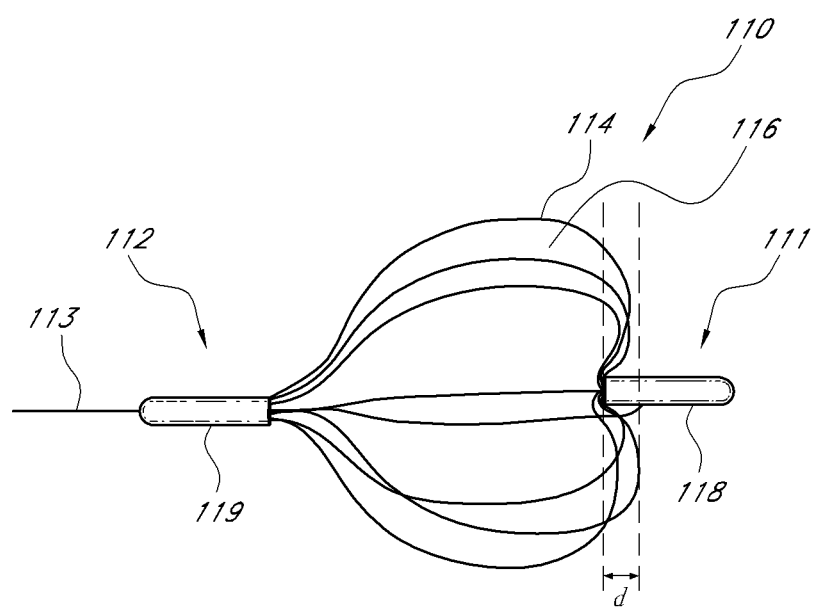
FIG. 14 illustrates another example embodiment of a vascular remodeling device.

FIG. 14 illustrates another example embodiment of a generally spherical vascular remodeling device 110. It will be appreciated that the device 110 may be more compliant than the vasculature in which it is deployed such that it may be somewhat misshapen (e.g., non-spherical) after being deployed, and that the phrase "generally spherical" describes the shape of the device 110 when in an expanded (e.g., fully expanded) state outside of vasculature. Additionally, the phrase "generally spherical" distinguishes the device 110, which is generally uniform in each dimension in an expanded state, from tubular devices having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 110 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm 20. Embodiments in which the length is greater than the width may be advantageous for positioning a portion of the device 110 in a portion of the aneurysm 20 (e.g., to aid in embolization).

The device 110 comprises a first or distal end 111 and a second or proximal end 112 substantially opposite the distal end 111. The device 110 further comprises a plurality of filaments 114 extending between the distal end 111 and the proximal end 112. In the device 110 illustrated in FIG. 14, the distal end 111 extends inwardly and the proximal end 112 extends outwardly to form a generally spherical shape similar to a pumpkin, a garlic bulb, or a rutabaga. In some embodiments, the filaments 114 are coupled at a position proximal to a bend at a distal end of the device 110 (e.g., as illustrated by the dimension d in FIG. 14). In certain embodiments, the filaments 114 are coupled at the distal end 111 and/or the proximal end 112 (e.g., by adhering, welding, soldering, combinations thereof, and the like). The device 110 may be connected to a catheter (e.g., the catheter 92 described herein) at the proximal end 112 of the device 110.

In the embodiment illustrated in FIG. 14, the device 110 comprises a lead or tail 113, which may be used for releasing and/or retracting the device 110 after deployment, as described herein. In some embodiments, the device 110 may be connected to the catheter at the lead or tail 113 of the device 110. In certain embodiments, the device 110 comprises a cut metallic sphere, a single filament (e.g., wrapped back and forth between the first and second ends), etc. It will be appreciated that a device in which the distal end extends outwardly and the proximal end extends inwardly and a device in which the distal end extends inwardly and the proximal end extends inwardly are also possible.

In certain embodiments, the device 110 is configured to be positioned at a junction of a bifurcation 60 (e.g., a neurovascular bifurcation) comprising at least one afferent vessel, efferent vessels, and an aneurysm 20 having a fundus and a neck. For example, in some embodiments, the device 110 is suitably dimensioned to fit in a junction of a bifurcation (e.g., having a diameter between about 2 mm and about 12 mm, having a diameter between about 6 mm and about 8 mm, having a diameter less than about 12 mm, having a diameter greater than about 2 mm). For another example, in some embodiments, the device 110 is less rigid than a junction of a bifurcation 60 (e.g., due to the number of filaments 114, the material of the filaments 114, the thickness of the filaments 114, the spacing of the filaments 114, the shape of the filaments 114, combinations thereof, and the like). In certain embodiments, the device 110 is configured to act as a scaffolding to inhibit or prevent herniation or prolapse of objects (e.g., embolization coils, thrombi, etc.) out of a neck of an aneurysm 20. For example, in some embodiments, the filaments 114 are dense enough at or proximate to the neck of the aneurysm 20 that objects generally cannot pass. In certain embodiments, the device 110 is configured to permit perfusion of fluid (e.g., blood) to efferent vessels of a bifurcation 60.

In some embodiments, at least one of the filaments 114 comprises a self-expanding and/or a shape-memory material (e.g., comprising Nitinol, CoCr alloy, MP35N®, L605, etc.), thereby causing the device 110 to be self-expanding under certain conditions (e.g., not restrained by a catheter). In some embodiments, at least one of the filaments 114 comprises a different material than others of the filaments 114 (e.g., some filaments 114 comprising Nitinol and some filaments 114 comprising Nitinol and platinum). In some embodiments, at least one of the filaments 114 comprises a radiopaque material (e.g., platinum). In certain such embodiments, an even number of filaments 84 (e.g. two, four, etc.) comprises a radiopaque material (e.g., platinum). In some embodiments, at least one of the filaments 84 comprises a radiopaque material (e.g., platinum) at least partially wrapped (e.g., coiled) around a self-expanding material (e.g., Nitinol). In some embodiments, at least one of the filaments 84 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, inter alia, on price, desired level of radiopacity, mechanical properties of the radiopaque material, and corrosion properties of the radiopaque material. In certain embodiments, the filaments 114 have a substantially circular or ovoid cross section (e.g., embodiments, in which the filaments 84 comprise separate wires). In some embodiments, the filaments 114 have a substantially rectangular or flat cross section (e.g., embodiments, in which the filaments 84 comprise uncut portions of a metallic tube, or ribbons). Other shapes of filaments 114 and combinations of shapes of filaments 114 are also possible. In certain embodiments, the plurality of filaments 84 comprises between about six and about twelve filaments 114. In certain embodiments, the plurality of filaments 114 comprises at least about six filaments 114, at least about eight filaments 114, or at least about twelve filaments 114. Other numbers of filaments 114 are also possible.

The device 110 comprises a plurality of perforations or cells 116 between the filaments 114. In some embodiments, a percentage of the outer surface of the device 110 or a portion thereof (e.g., proximate to the distal end 111) covered by the filaments 114 is greater than or equal to about 3%. In some embodiments, a percentage of the outer surface of the device 110 or a portion thereof (e.g., proximate to the distal end 111) covered by the filaments 114 is between about 3% and about 15% (e.g., about 5%). In some embodiments, a percentage of the outer surface of the device 110 or a portion thereof (e.g., proximate to the distal end 111) covered by the filaments 114 is between about 3% and about 25%. In some embodiments, a percentage of the outer surface of the device 110 or a portion thereof (e.g., proximate to the distal end 111) covered by the cells 116 is less than or equal to about 97%. In some embodiments, a percentage of the outer surface of the device 110 or a portion thereof (e.g., proximate to the distal end 111) covered by the cells 116 is between about 85% and about 97% (e.g., about 95%). In some embodiments, a percentage of the outer surface of the device 110 or a portion thereof (e.g., proximate to the distal end 111) covered by the cells 116 is between about 75% and about 97%. In certain embodiments, a percentage of the outer surface of the device 110 or a portion thereof (e.g., proximate to the distal end 111) covered by the filaments 114 is between about 25% and about 40%. In certain embodiments, a percentage of the outer surface of the device 110 or a portion thereof (e.g., proximate to the distal end 111) covered by the cells 116 is between about 60% and about 75%. Other porosities are also possible. In some embodiments, porosity distally increases between the proximal end 112 and an approximate midpoint and distally decreases between the approximate midpoint and the distal end 111.

In some embodiments, the device 110 comprises a radiopaque marker 118 proximate to the distal end 111 and/or a radiopaque marker 119 proximate to the proximal end 112. In certain embodiments, the radiopaque marker 118 may extend at least partially into the aneurysm 20 when the device 110 is positioned at the junction of a bifurcation 60. In some embodiments, the radiopaque markers 118, 119 may comprise a sleeve situated or wrapped around the filaments 114, thereby coupling the filaments 114. The radiopaque markers 118, 119 may aid in positioning the device 110 at the junction of a bifurcation 60.

In certain embodiments, the device 110 is configured to be highly conformable to the junction of a bifurcation 60 (e.g., a neurovascular bifurcation) comprising at least one afferent vessel, efferent vessels, and an aneurysm 20 having a fundus and a neck. For example, in certain embodiments, the remodeling device 110 comprises filaments 114 comprising a material and having a thickness and cross-sectional shape that allows good compliance with and conformability to the vasculature at the junction of the bifurcation 60.

In some embodiments, at least one filament 114 of the plurality of filaments 114 comprises a round wire (e.g., having a circular cross-section). In certain such embodiments, the round wire has a diameter between about 0.002" (approx. 0.05 mm) and about 0.006" (approx. 0.15 mm), between about 0.0025" (approx. 0.05 mm) and about 0.004" (approx. 0.10 mm) or between about 0.003" (approx. 0.08 mm) and about 0.0037" (approx. 0.09 mm). In some embodiments, the round wire comprises and outer sheath comprising a first material and an inner core comprising a second material (e.g., comprising platinum, platinum-tungsten, tantalum, silver, or gold). In some embodiments, the second material of the inner core is radiopaque. In some embodiments, at least one filament 114 comprises a thin wire coiled around a round wire. In certain such embodiments, the thin wire has a diameter between about 0.009" (approx. 0.023 mm) and about 0.002" (approx. 0.051 mm), between about 0.001" (approx. 0.025 mm) and about 0.0175" (approx. 0.044 mm), or between about 0.00125" (approx. 0.032 mm) and about 0.0015" (approx. 0.038 mm). In some embodiments, the thin wire comprises platinum, platinum-tungsten, tantalum, silver, or gold. In some embodiments, the thin wire comprises a radiopaque material.

In certain embodiments, at least one filament 114 of the plurality of filaments 114 comprises a flat wire or ribbon (e.g., having a rectangular cross-section). In certain such embodiments, the flat wire has a thickness between about 0.001" (approx. 0.0025 mm) and about 0.003" (approx. 0.076 mm) and a width between about 0.003" and about 0.005", a thickness between about 0.0015" (approx. 0.0381 mm) and about 0.0025" (approx. 0.064 mm) and a width between about 0.0035" (approx. 0.089 mm) and about 0.0045" (approx. 0.114 mm), or a thickness between about 0.00175" (approx. 0.044 mm) and about 0.00225" (approx. 0.057 mm) and a width between about 0.00375" (approx. 0.095 mm) and about 0.00425" (approx. 0.108 mm).

In certain embodiments, the device comprises between about 4 filaments 114 and about 12 filaments 114 or between about 6 filaments 114 and about 12 filaments 114. Other numbers of filaments 114 are also possible. In certain embodiments, combinations of different filaments 114 are used in the same device 110 (e.g., 6 filaments comprising Nitinol and 2 filaments comprising Nitinol and having a thin platinum wire coiled around the two round filaments).

The disclosures of U.S. Provisional Patent Application No. 61/082,579, filed Jul. 22, 2008, and U.S. patent application Ser. No. 12/506,945, filed Jul. 21, 2009, may be relevant to certain of the generally spherical vascular remodeling devices described herein such as the device 110, and the disclosure each of those applications is incorporated herein by reference in its entirety.

In some embodiments, the device 110 is reshapable and/or lockable, for example comprising certain features described herein and depicted in FIGS. 6A-7B. In some embodiments, the device 110 may further comprise a covering as described herein and depicted in FIGS. 8A and 8B. In certain embodiments the distal ends of the filaments 114 comprise a coating configured to preferentially repel certain material. In some embodiments, the coating is configured to preferentially repel liquid embolic material (e.g., Onyx®). In some embodiments, forming the coating on the distal ends of the filaments 114 comprises chemically treating the filaments 114. Certain such coatings may allow delivery of liquid embolic material through the device 110 while inhibiting, reducing, or preventing permeation of the liquid embolic material from out of the aneurysm through the device 110.

A highly conformable remodeling device comprising filaments 114 such as certain embodiments described herein may possess greater conformability at the junction of a bifurcation 60 than a balloon-remodeling device designed to perform the same function (for example those described herein and in U.S. patent application Ser. No. 10/235,064, filed Sep. 4, 2002, and U.S. patent application Ser. No. 11/868,049, filed Oct. 5, 2007, each of which are incorporated herein by reference in its entirety), for example possibly because a balloon has a continuous surface that generally wholly conforms to a junction, whereas a highly conformable remodeling device described herein only conforms to the junction where the filaments 114 contact the vasculature.

A remodeling device comprising filaments 114 such as certain embodiments described herein may reduce damage to vasculature by permitting blood to flow to efferent vessels of a bifurcation 60 throughout a treatment process after a single deployment from a catheter, whereas a balloon-remodeling device generally occludes flow to the efferent vessels such that the balloon is periodically deflated in order to restore perfusion, and such repeated inflation and deflation may damage the vasculature.

The disclosures of U.S. Provisional Patent Application No. 61/082,579, filed Jul. 22, 2008, and U.S. patent application Ser. No. 12/506,945, filed Jul. 21, 2009, may be relevant to certain of the generally spherical vascular remodeling devices described herein such as the device 110, and the disclosure each of those applications is incorporated herein by reference in its entirety.

In some embodiments, the apparatus 110 is used to treat an aneurysm 20 using a method similar to the method depicted in FIGS. 9A-9Ciib. In some embodiments, the apparatus 110 is used to treat an aneurysm 20 using a method similar to the method depicted in FIGS. 12A-12D. Other treatment methods are also possible.

As described above, the term "bifurcation" described herein is not limited to the particular vasculature illustrated in FIGS. 9A-9Ciib and 13A-13D, for example having efferent vessels at substantially different angles, having efferent vessels that are substantially different sizes, and/or having a different quantity of efferent vessels and/or the aneurysm of the bifurcation may be offset with respect to the junction (e.g., having a neck substantially open to one efferent vessel), tilted with respect to a plane created by the vessels (e.g., into or out of the page), etc.

Figure 15:
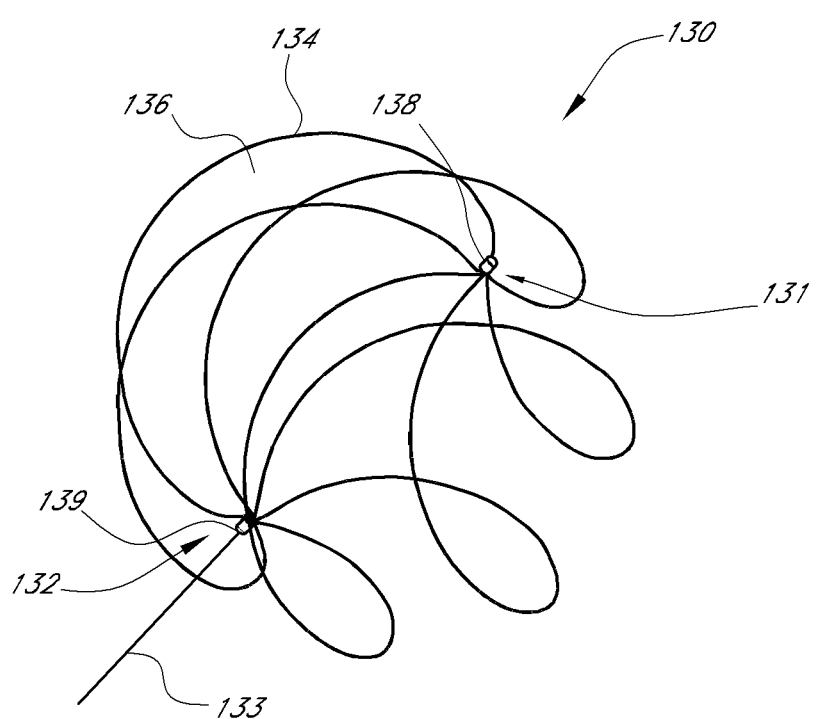
FIG. 15 illustrates another example embodiment of a vascular remodeling device.

FIG. 15 illustrates still another example embodiment of a generally spherical vascular remodeling device 130. It will be appreciated that the device 130 may be more compliant than the vasculature in which it is deployed such that it may be somewhat misshapen (e.g., non-spherical) after being deployed, and that the phrase "generally spherical" describes the shape of the device 130 when in an expanded (e.g., fully expanded) state outside of vasculature. Additionally, the phrase "generally spherical" distinguishes the device 130, which is generally uniform in each dimension in an expanded state, from tubular stents having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 130 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm 20. Embodiments in which the length is greater than the width may be advantageous for positioning a portion of the device 130 in a portion of the aneurysm 20 (e.g., to aid in embolization).

The device 130 comprises a first or distal end 131 and a proximal or proximal end 132 substantially opposite the distal end 131. The device 130 further comprises a plurality of filaments 134 extending between the distal end 131 and the proximal end 132. In the device 130 illustrated in FIG. 15, the distal end 131 extends outwardly and the proximal end 132 extends outwardly to form a generally spherical shape similar to a twisted sphere (e.g., after rotating one or both ends 81, 82 of the device 80 illustrated in FIG. 5 with respect to each other). In certain embodiments, the filaments 134 are coupled at the distal end 131 and/or the proximal end 132 (e.g., by adhering, welding, soldering, combinations thereof, and the like). In contrast to the filaments 84 of the device 80 illustrated in FIG. 5, which in some embodiments are straight enough to form a plane, the filaments 134 of the device 130 are longitudinally angled at or adjacent to at least the proximal end 132. The device 130 may be connected to a catheter (e.g., the catheter 92 described herein) at the proximal end 132 of the device 130. In the embodiment illustrated in FIG. 15, the device 130 comprises a lead or tail 133, which may be used for releasing and/or retracting the device 130 after deployment, as described herein. In some embodiments, the device 130 may be connected to the catheter 92 at the lead or tail 133 of the device 130. In some embodiments, deployment and/or retraction of the device 130 uses less force than retraction of for example, the devices 50, 80, 110. In certain embodiments, the device 130 comprises a cut metallic sphere, a single filament (e.g., wrapped back and forth between the first and second ends), etc.

In certain embodiments, the device 130 is configured to be positioned at a junction of a bifurcation 60 (e.g., a neurovascular bifurcation) comprising at least one afferent vessel, efferent vessels, and an aneurysm 20 having a fundus and a neck. For example, in some embodiments, the device 130 is suitably dimensioned to fit in a junction of a bifurcation 60 (e.g., having a diameter between about 2 mm and about 12 mm, having a diameter between about 6 mm and about 8 mm, having a diameter less than about 12 mm, having a diameter greater than about 2 mm). For another example, in some embodiments, the device 130 is less rigid than a junction of a bifurcation 60 (e.g., due to the number of filaments 134, the material of the filaments 134, the thickness of the filaments 134, the spacing of the filaments 134, the shape of the filaments 134, combinations thereof, and the like). In certain embodiments, the device 130 is configured to act as a scaffolding to inhibit or prevent herniation or prolapse of objects (e.g., embolization coils, thrombi, etc.) out of a neck of an aneurysm 20. For example, in some embodiments, the filaments 134 are dense enough at or proximate to the neck of the aneurysm 20 that objects generally cannot pass. In certain embodiments, the device 130 is configured to permit perfusion of fluid (e.g., blood) to efferent vessels of a bifurcation 60.

In some embodiments, at least one of the filaments 134 comprises a self-expanding and/or a shape-memory material (e.g., comprising Nitinol, CoCr alloy, MP35N®, L605, etc.), thereby causing the device 130 to be self-expanding under certain conditions (e.g., not restrained by a catheter). In some embodiments, at least one of the filaments 134 comprises a different material than others of the filaments 134 (e.g., some filaments 134 comprising Nitinol and some filaments 134 comprising Nitinol and platinum). In some embodiments, at least one of the filaments 134 comprises a radiopaque material (e.g., platinum). In certain such embodiments, an even number of filaments 84 (e.g. two, four, etc.) comprises a radiopaque material (e.g., platinum). In some embodiments, at least one of the filaments 84 comprises a radiopaque material (e.g., platinum) at least partially wrapped (e.g., coiled) around a self-expanding material (e.g., Nitinol). In some embodiments, at least one of the filaments 84 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, infer alia, on price, desired level of radiopacity, mechanical properties of the radiopaque material, and corrosion properties of the radiopaque material. In certain embodiments, the filaments 134 have a substantially circular or ovoid cross section (e.g., embodiments, in which the filaments 84 comprise separate wires). In some embodiments, the filaments 134 have a substantially rectangular or flat cross section (e.g., embodiments, in which the filaments 84 comprise uncut portions of a metallic tube, or ribbons). Other shapes of filaments 134 and combinations of shapes of filaments 134 are also possible. In certain embodiments, the plurality of filaments 84 comprises between about six and about twelve filaments 134. In certain embodiments, the plurality of filaments 134 comprises at least about six filaments 134, at least about eight filaments 134, or at least about twelve filaments 134. Other numbers of filaments 134 are also possible.

The device 130 comprises a plurality of perforations or cells 136 between the filaments 134. In some embodiments, a percentage of the outer surface of the device 130 or a portion thereof (e.g., proximate to the distal end 131) covered by the filaments 134 is greater than or equal to about 3%. In some embodiments, a percentage of the outer surface of the device 130 or a portion thereof (e.g., proximate to the distal end 131) covered by the filaments 134 is between about 3% and about 15% (e.g., about 5%). In some embodiments, a percentage of the outer surface of the device 130 or a portion thereof (e.g., proximate to the distal end 131) covered by the filaments 134 is between about 3% and about 25%. In some embodiments, a percentage of the outer surface of the device 130 or a portion thereof (e.g., proximate to the distal end 131) covered by the cells 136 is less than or equal to about 97%. In some embodiments, a percentage of the outer surface of the device 130 or a portion thereof (e.g., proximate to the distal end 131) covered by the cells 136 is between about 85% and about 97% (e.g., about 95%). In some embodiments, a percentage of the outer surface of the device 130 or a portion thereof (e.g., proximate to the distal end 131) covered by the cells 136 is between about 75% and about 97%. In certain embodiments, a percentage of the outer surface of the device 130 or a portion thereof (e.g., proximate to the distal end 131) covered by the filaments 134 is between about 25% and about 40%. In certain embodiments, a percentage of the outer surface of the device 130 or a portion thereof (e.g., proximate to the distal end 131) covered by the cells 136 is between about 60% and about 75%. Other porosities are also possible. In some embodiments, porosity distally increases between the proximal end 132 and an approximate midpoint and distally decreases between the approximate midpoint and the distal end 131.

In some embodiments, the device 130 comprises a radiopaque marker 138 proximate to the distal end 131 and/or a radiopaque marker 139 proximate to the proximal end 132. In certain embodiments, the radiopaque marker 138 may extend at least partially into the aneurysm 20 when the device 130 is positioned at the junction of a bifurcation 60.

In some embodiments, the radiopaque markers 138, 139 may comprise a sleeve situated or wrapped around the filaments 134, thereby coupling the filaments 134. The radiopaque markers 138, 139 may aid in positioning the device 130 at the junction of a bifurcation 60.

In certain embodiments, the device 130 is configured to be highly conformable to the junction of a bifurcation 60 (e.g., a neurovascular bifurcation) comprising at least one afferent vessel, efferent vessels, and an aneurysm 20 having a fundus and a neck. For example, in certain such embodiments, the remodeling device 130 comprises filaments 134 comprising a material and having a thickness and cross-sectional shape that allows good compliance with and conformability to the vasculature at the junction of the bifurcation 60.

In some embodiments, at least one filament 134 of the plurality of filaments 134 comprises a round wire (e.g., having a circular cross-section). In certain such embodiments the round wire has a diameter between about 0.002" (approx. 0.05 mm) and about 0.006" (approx. 0.15 mm), between about 0.0025" (approx. 0.05 mm) and about 0.004" (approx. 0.10 mm), or between about 0.003" (approx. 0.08 mm) and about 0.0037" (approx. 0.09 mm). In some embodiments, the round wire comprises an outer sheath comprising a first material and an inner core comprising a second material (e.g., platinum, platinum-tungsten, tantalum, silver, or gold). In some embodiments, the second material of the inner core is radiopaque. In some embodiments, at least one filament 134 of the plurality of filaments 134 comprises a thin wire coiled around a round wire. In certain such embodiments, the thin wire has a diameter between about 0.009" (approx. 0.023 mm) and about 0.002" (approx. 0.051 mm), between about 0.001" (approx. 0.025 mm) and about 0.0175" (approx. 0.044 mm), or between about 0.00125" (approx. 0.032 mm) and about 0.0015" (approx. 0.038 mm). In some embodiments, the thin wire comprises platinum, platinum-tungsten, tantalum, silver, or gold. In some embodiments, the thin wire comprises a radiopaque material.

In certain embodiments, at least one filament 134 of the plurality of filaments 134 comprises a flat wire or ribbon (e.g., having a rectangular cross-section). In certain such embodiments, the flat wire has a thickness between about 0.001" (approx. 0.0025 mm) and about 0.003" (approx. 0.076 mm) and a width between about 0.003" and about 0.005", a thickness between about 0.0015" (approx. 0.0381 mm) and about 0.0025" (approx. 0.064 mm) and a width between about 0.0035" (approx. 0.089 mm) and about 0.0045" (approx. 0.114 mm), or a thickness between about 0.00175" (approx. 0.044 mm) and about 0.00225" (approx. 0.057 mm) and a width between about 0.00375" (approx. 0.095 mm) and about 0.00425" (approx. 0.108 mm).

In certain embodiments, the device 130 comprises about 4 filaments 134 to about 12 filaments 134 or between about 6 filaments 134 and about 12 filaments 134. Other numbers of filaments 134 are also possible. In certain embodiments, combinations of different filaments 134 are used in the same device 130 (e.g., 6 filaments comprising Nitinol and 2 round filaments comprising Nitinol and having a thin platinum wire coiled around the two round filaments).

The disclosures of U.S. Provisional Patent Application No. 61/082,579, filed Jul. 22, 2008, and U.S. patent application Ser. No. 12/506,945, filed Jul. 21, 2009, may be relevant to certain of the generally spherical vascular remodeling devices described herein such as the device 110, and the disclosure each of those applications is incorporated herein by reference in its entirety.

In some embodiments, the device 130 is reshapable and/or lockable, for example comprising certain features described herein and depicted in FIGS. 6A-7B. In some embodiments, the device 130 comprises a covering, for example as described herein with respect to FIGS. 8A and 8B. In certain embodiments the distal ends of the filaments 134 comprise a coating configured to preferentially repel certain material. In some embodiments, the coating is configured to preferentially repel liquid embolic material (e.g., Onyx®). In some embodiments, forming the coating on the distal ends of the filaments 134 comprises chemically treating the filaments 134. Certain such coatings may allow delivery of liquid embolic material through the device 130 while inhibiting, reducing, or preventing permeation of the liquid embolic material from out of the aneurysm through the device 130.

A highly conformable remodeling device comprising filaments 134 such as certain embodiments described herein may possess greater conformability at the junction of a bifurcation 60 than a balloon-remodeling device designed to perform the same function (for example those described herein and in U.S. patent application Ser. No. 10/235,064, filed Sep. 4, 2002, and U.S. patent application Ser. No. 11/868,049, filed Oct. 5, 2007, each of which are incorporated herein by reference in its entirety), for example possibly because a balloon has a continuous surface that generally wholly conforms to a junction, whereas a highly conformable remodeling device described herein only conforms to the junction where the filaments 134 contact the vasculature.

A remodeling device comprising filaments 134 such as certain embodiments described herein may reduce damage to vasculature by permitting blood to flow to efferent vessels of a bifurcation 60 throughout a treatment process after a single deployment from a catheter, whereas a balloon-remodeling device generally occludes flow to the efferent vessels such that the balloon is periodically deflated in order to restore perfusion, and such repeated inflation and deflation may damage the vasculature.

In some embodiments, the apparatus 130 is used to treat an aneurysm 20 using a method similar to the method depicted in FIGS. 9A-9Ciib. In some embodiments, the apparatus 130 is used to treat an aneurysm 20 using a method similar to the method depicted in FIGS. 13A-13D. Other treatment methods are also possible.

As described above, the term "bifurcation" described herein is not limited to the particular vasculature illustrated in FIGS. 9A-9Ciib and 13A-13D, for example having efferent vessels at substantially different angles, having efferent vessels that are substantially different sizes, and/or having a different quantity of efferent vessels and/or the aneurysm of the bifurcation may be offset with respect to the junction (e.g., having a neck substantially open to one efferent vessel), tilted with respect to a plane created by the vessels (e.g., into or out of the page), etc.

Figure 16A:
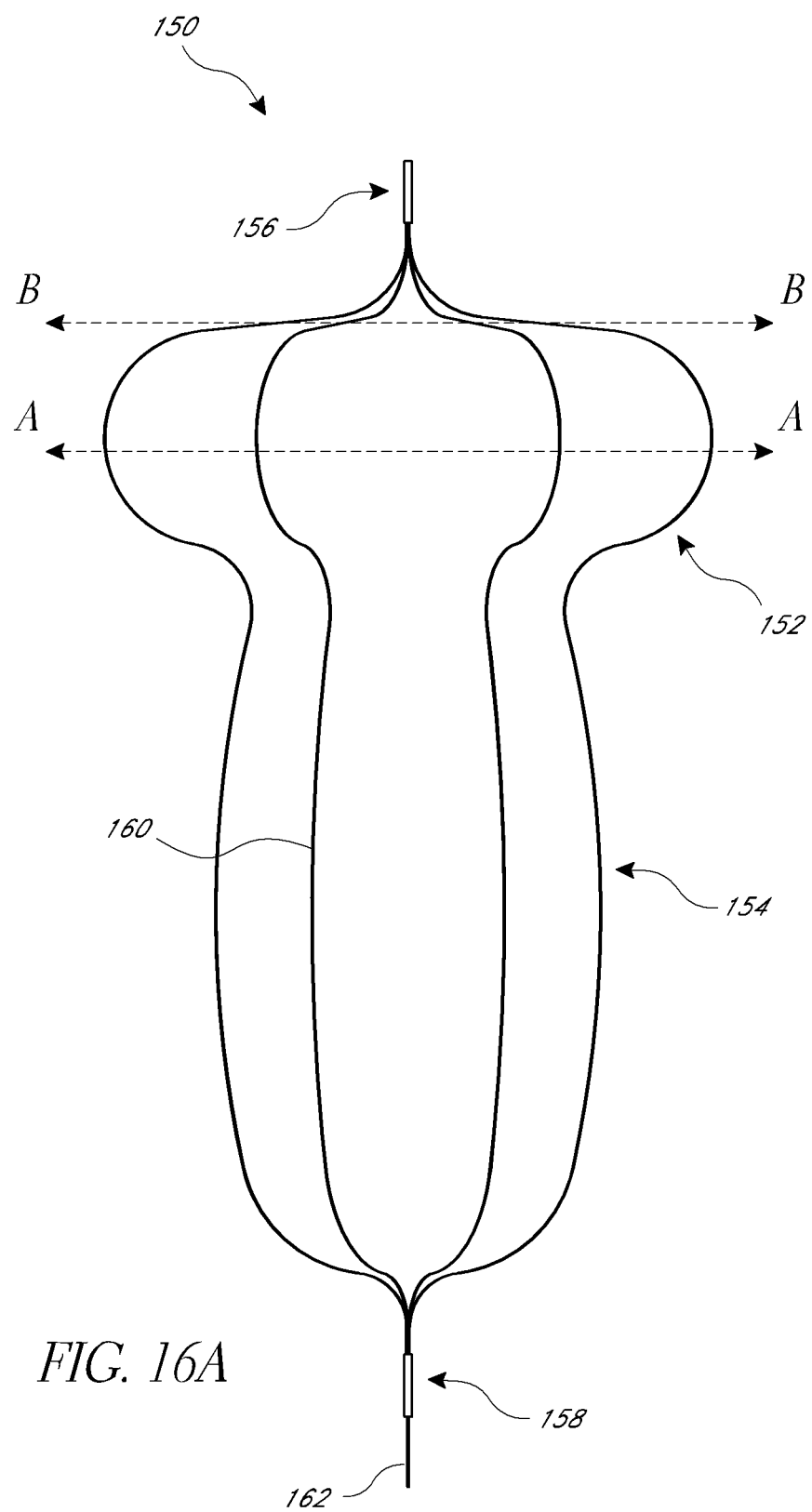
FIG. 16A illustrates a side elevational view of another example embodiment of a vascular remodeling device.
Figure 16B:
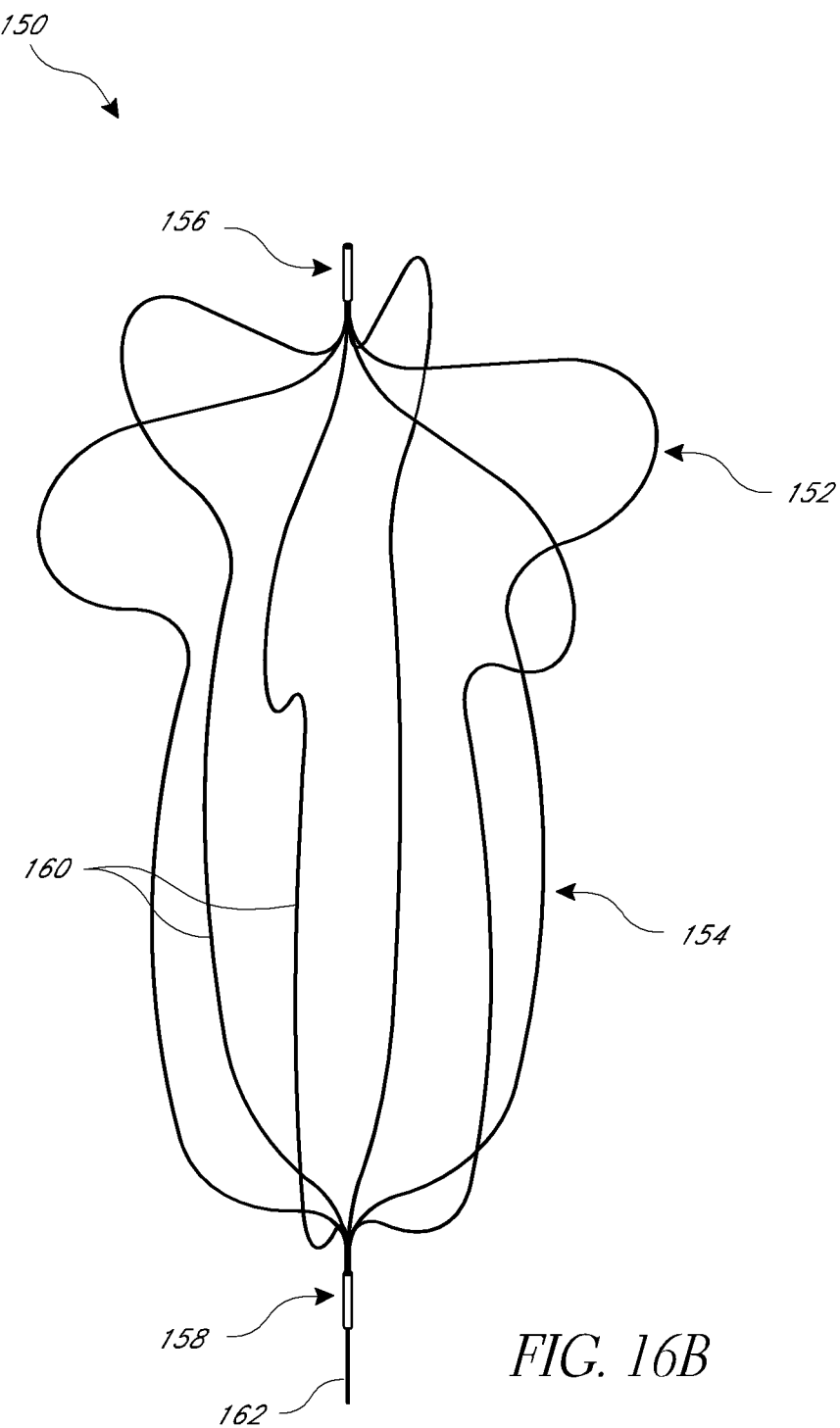
FIG. 16B illustrates a top perspective view of the device of FIG. 16A.
Figure 16C:
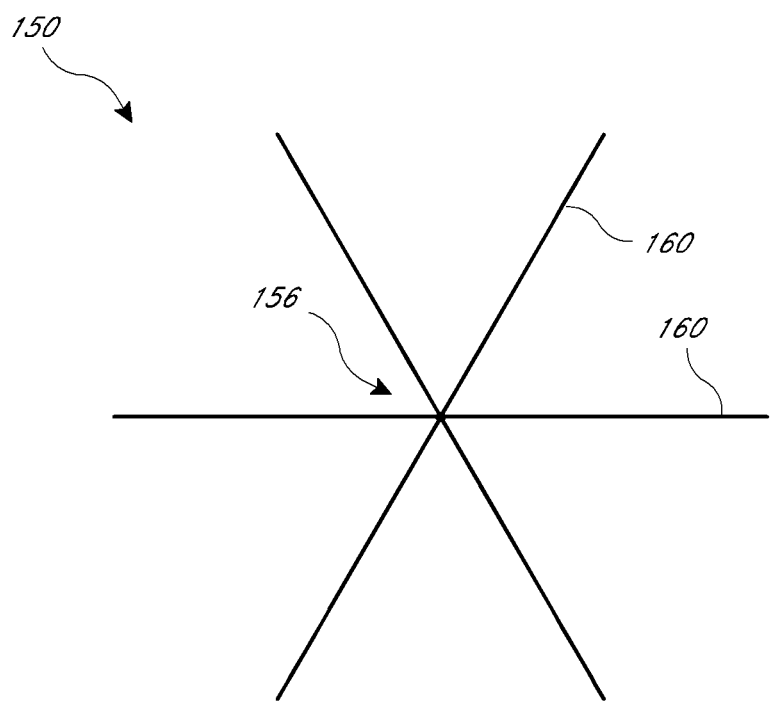
FIG. 16C illustrates a top plan view of the device of FIG. 15A.

FIGS. 16A-16C depict an example embodiment of a generally butternut squash, winter squash, or harvest squash-shaped or an acorn-shaped device 150. It will be appreciated that the device 150 may be more compliant than the vasculature in which it is deployed such that it may be somewhat misshapen (e.g., non-squash shaped, for example as illustrated in FIG. 20D) after being deployed, and that the shapes herein describe the shape of the device 150 when in an expanded (e.g., fully expanded) state outside of vasculature. Additionally, the shapes described herein distinguish the device 150 from tubular devices having a small and uniform radial dimension and a large longitudinal dimension in an expanded state.

As depicted in FIGS. 16A and 16B, the device 150 comprises a first or distal end 156 and a second or proximal end 158. The device 150 further comprises a first or distal portion 152 and a second or proximal portion 154. The distal portion 152 is between the distal end 156 and the proximal portion 154, and the proximal portion 154 is between the distal portion 152 and the proximal end 158. The device 150 comprises a plurality of filaments 160 extending between the distal end 156 and the proximal end 158 and coupled at the proximal end 158 and at the distal end 152. The filaments 160 may at least partially define a device 150 that is generally shaped like a butternut squash, winter squash, or harvest squash or an acorn. In an expanded state, starting at the proximal end 158, the filaments 160 extend radially outwardly, are substantially parallel (e.g., having slight bends from proximal to distal) in the proximal portion 154, and extend further radially outwardly and then radially inwardly in the distal portion 152. The filaments 160 may comprise an arcuate (e.g., semi-circular) shape in the distal portion 152. The filaments 160 may define a generally oblong shape in the proximal portion 154. The filaments 160 may define a generally spherical shape if the proximal portion 154 is longitudinally short. In some embodiments, the diameter of at least a section of the distal portion 152 is greater than the diameter of the proximal portion 154. In certain embodiments, the diameter of a section of the distal portion 152 near an approximate midpoint of the distal portion 152 (e.g., at the line A-A in FIG. 16A) is greater than the diameter of the proximal portion 154. In some embodiments, the filaments 160 are coupled at the distal end 156 and/or the proximal end 158 (e.g., by adhering, welding, soldering, combinations thereof, and the like). In some embodiments, the device 150 is connected to a catheter (e.g., the catheter 168 described herein) at the proximal end 158 of the device 150. The device 150 may comprise a lead or tail 162, which may be used for releasing and/or retracting the device 150 after deployment, as described herein. The device 150 may be connected to a catheter (e.g., the catheter 168 described herein) at the lead or tail 162 of the device 150. In certain embodiments, the device 150 comprises a cut metallic sphere, a single filament (e.g., wrapped back and forth between the first and second ends). etc. FIG. 16C is a top plan view (from the distal end 156) of the device 150, and illustrates the filaments 160 that can act as a scaffolding to inhibit herniation of objects out of an aneurysm.

In certain embodiments, the device 150 is configured to be positioned at a junction of a bifurcation (e.g., a neurovascular bifurcation) comprising at least one afferent vessel, efferent vessels, and an aneurysm 20 having a fundus and a neck. For example, in some embodiments, the device 150 is suitably dimensioned to fit in a junction of a bifurcation (e.g., having a largest diameter between about 2 mm and about 12 mm, having a largest diameter between about 6 mm and about 8 mm, having a largest diameter less than about 12 mm, having a largest diameter greater than about 2 mm). In certain embodiments, the device 150 is configured to be positioned in a junction of a bifurcation, wherein the proximal portion 154 is configured to abut an ostium of the afferent vessel, as illustrated in FIG. 20D. For another example, in some embodiments, the device 150 is less rigid than a junction of a bifurcation (e.g., due to the number of filaments 160, the material of the filaments 160, the thickness of the filaments 160, the spacing of the filaments 160, the shape of the filaments 160, combinations thereof, and the like). In certain embodiments, the device 150 is configured to act as a scaffolding to inhibit or prevent herniation or prolapse of objects (e.g., embolization coils, embolic fluid, thrombi, etc.) out of a neck of an aneurysm 20. For example, in some embodiments, the filaments 160 are dense enough at or proximate to the neck of the aneurysm 20 that objects generally cannot pass. In certain embodiments, the device 160 is configured to permit perfusion of fluid (e.g., blood) to efferent vessels of a bifurcation.

In some embodiments, at least one of the filaments 160 comprises a self-expanding and/or a shape-memory material (e.g., comprising Nitinol, CoCr alloy, MP35N®, L605, etc.), thereby causing the device 150 to be self-expanding under certain conditions (e.g., not restrained by a catheter). In some embodiments, at least one of the filaments 160 comprises a different material than others of the filaments 160 (e.g., some filaments 160 comprising Nitinol and some filaments 160 comprising Nitinol and platinum). In some embodiments, at least one of the filaments 160 comprises a radiopaque material (e.g., platinum). In certain such embodiments, an even number of filaments 160 (e.g., two, four, etc.) comprises a radiopaque material (e.g., platinum). In some embodiments, at least one of the filaments 160 comprises a radiopaque material (e.g., platinum) at least partially wrapped (e.g., coiled) around a self-expanding material (e.g., Nitinol). In some embodiments, at least one of the filaments 160 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, infer alia, on price, desired level of radiopacity, mechanical properties of the radiopaque material, and corrosion properties of the radiopaque material. In certain embodiments, the filaments 160 have a substantially circular or ovoid cross section (e.g., embodiments, in which the filaments 160 comprise separate wires). In some embodiments, the filaments 160 have a substantially rectangular or flat cross section (e.g., embodiments, in which the filaments 160 comprise uncut portions of a metallic tube, as described below, or ribbons). Other shapes of filaments 160 and combinations of shapes of filaments 160 are also possible. In certain embodiments, the plurality of filaments 160 comprises between about six and about twelve filaments 160. In certain embodiments, the plurality of filaments 160 comprises at least about six filaments 160, at least about eight filaments 160, or at least about twelve filaments 160. Other numbers of filaments 160 are also possible.

The device 150 comprises a plurality of perforations or cells 164 between the filaments 160. In some embodiments, a percentage of the outer surface of the device 150 or a portion thereof (e.g., approximately at the line B-B in FIG. 16A) covered by the filaments 160 is greater than or equal to about 3%. In some embodiments, a percentage of the outer surface of the device 150 or a portion thereof (e.g., approximately at the line B-B in FIG. 16A) covered by the filaments 160 is between about 3% and about 15% (e.g., about 5%). In some embodiments, a percentage of the outer surface of the device 150 or a portion thereof (e.g., approximately at the line B-B in FIG. 16A) covered by the filaments 160 is between about 3% and about 25%. In some embodiments, a percentage of the outer surface of the device 150 or a portion thereof (e.g., approximately at the line B-B in FIG. 16A) covered by the cells 164 is less than or equal to about 97%. In some embodiments, a percentage of the outer surface of the device 150 or a portion thereof (e.g., approxi-mately at the line B-B in FIG. 16A) covered by the cells 164 is between about 85% and about 97% (e.g., about 95%). In some embodiments, a percentage of the outer surface of the device 150 or a portion thereof (e.g., approximately at the line B-B in FIG. 16A) covered by the cells 164 is between about 75% and about 97%. In certain embodiments, a percentage of the outer surface of the device 150 or a portion thereof (e.g., approximately at the line B-B in FIG. 16A) covered by the filaments 160 is between about 25% and about 40%. In certain embodiments, a percentage of the outer surface of the device 150 or a portion thereof (e.g., approximately at the line B-B in FIG. 16A) covered by the cells 164 is between about 60% and about 75%. Other porosities are also possible. In some embodiments, porosity distally increases between the distal end 156 and an approximate midpoint of the distal portion 152 (e.g., approximately at the line A-A in FIG. 16A). For example, cross-sections taken along the lines A-A and B-B in FIG. 16A each have the same number of filaments 160, but at the cross-section A-A the filaments 160 are spaced further apart from each other than at the cross-section B-B. As an example, if the device comprises ten filaments 160 each having a thickness of 0.5 mm, the porosity at the cross-section A-A would be about 80% with an example circumference of about 25 mm:

$$100\% \times [1-(\approx 0.5 \text{ mm/filament} \times 10 \text{ filaments}/\approx 25 \text{ mm})] \approx 80\%$$

and the porosity at the cross-section B-B would be about 33% with an example circumference of about 7.5 mm:

$$100\% \times [1-(\approx 0.5 \text{ mm/filament} \times 10 \text{ filaments}/ \text{ mm})] \approx 33\%.$$

High porosity proximate to a midpoint of the distal portion 152 and in the proximal portion 154 of the device 150 may provide good fluid flow to efferent vessels. Low porosity proximate to the distal end 156 of the device 150 may provide good scaffolding properties.

Figure 17A:
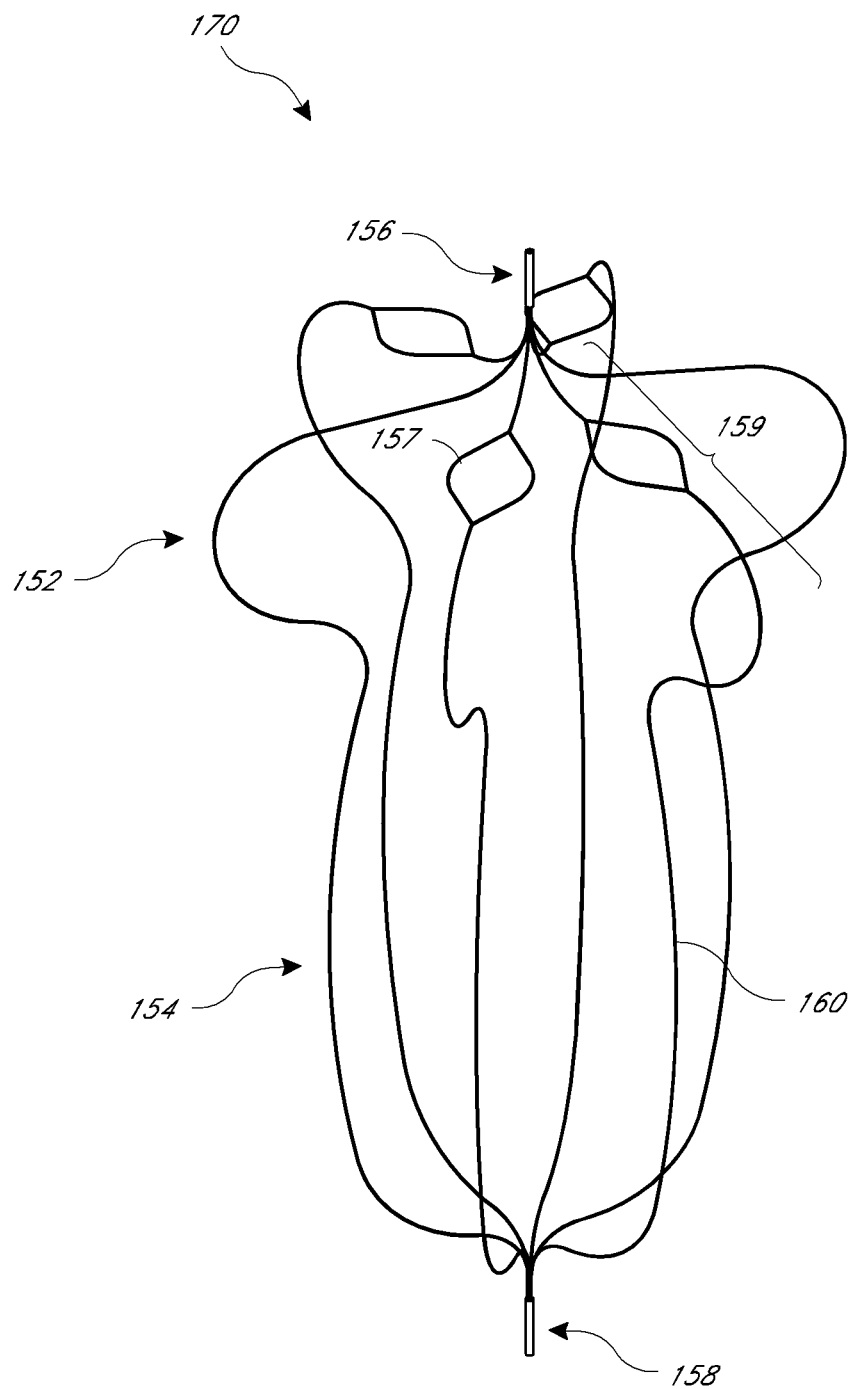
FIG. 17A illustrates a top perspective view of another example embodiment of a vascular remodeling device.
Figure 17B:
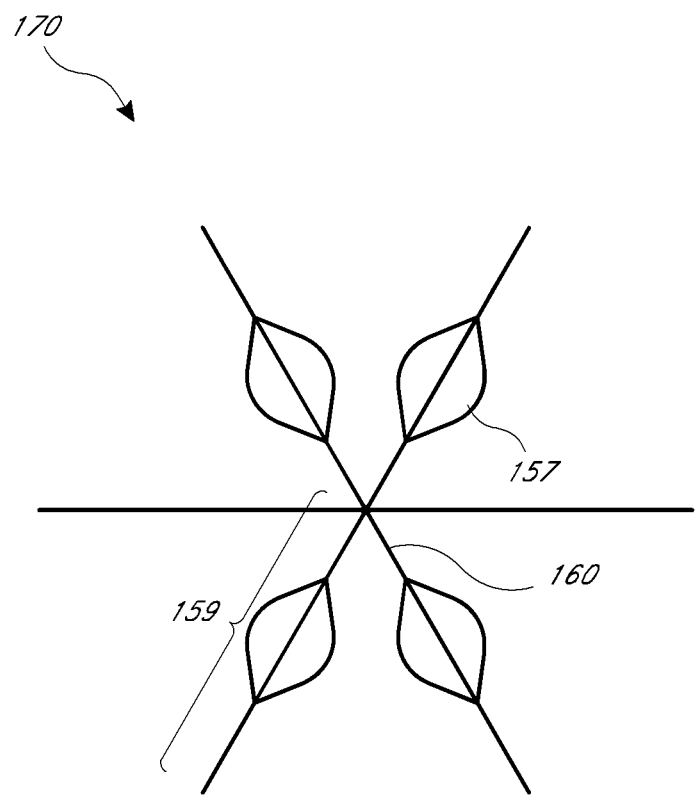
FIG. 17B illustrates a top plan view of the device of FIG. 17A.
Figure 18A:
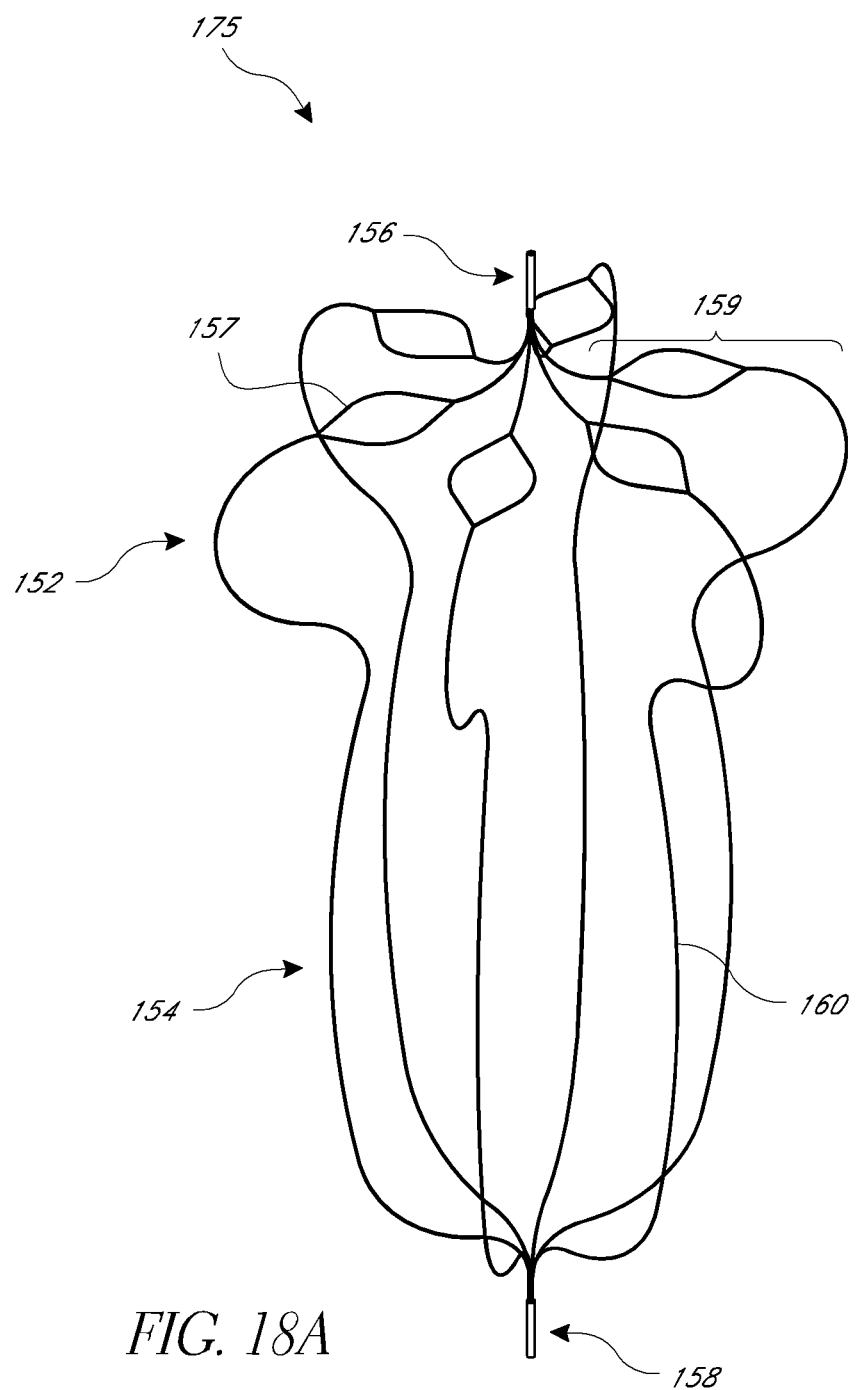
FIG. 18A illustrates a top perspective view of another example embodiment of a vascular remodeling device.
Figure 18B:
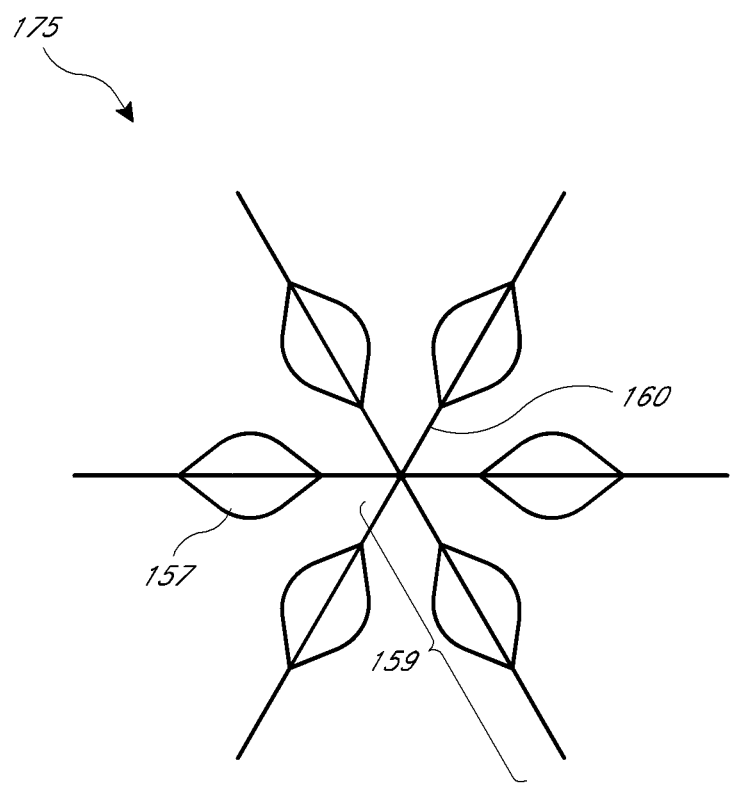
FIG. 18B illustrates a top plan view of the device of FIG. 18A.

FIGS. 17A and 17B, 18A and 18B, and 19A and 19B illustrate devices 170, 175, 185, respectively, that are squash-shaped but that have been modified to increase the amount of material or to decrease the porosity at the distal end 156. In some embodiments, a percentage of the distal end 156 covered by the filaments 160 is greater than or equal to about 3%. In some embodiments, a percentage of the distal end 156 covered by the filaments 160 is between about 3% and about 15% (e.g., about 5%). In some embodiments, a percentage of the distal end 156 covered by the filaments 160 is between about 3% and about 25%. In some embodiments, a percentage of the distal end 156 covered by the cells 164 is less than or equal to about 97%. In some embodiments, a percentage of the distal end 156 covered by the cells 164 is between about 85% and about 97% (e.g., about 95%). In some embodiments, a percentage of the distal end 156 covered by the cells 164 is between about 75% and about 97%. In some embodiments, a percentage of the distal end 156 covered by the filaments 160 may be between about 25% and about 40%. In some embodiments, a percentage of the distal end 156 covered by the cells 164 is between about 60% and about 75%. FIG. 17A depicts a device 170 in which some of the filaments 160 comprise an almond-shaped or leaf-shaped feature 157 at a distal section 159 of the filaments 160, creating a snowflake-like pattern best seen in the top plan view of FIG. 17B. Comparing FIG. 16C to FIG. 17B, the amount of material that can act as scaffolding to inhibit herniation of objects out of an aneurysm is greater in FIG. 17B due to the features 157. FIGS. 18A and 18B depict an embodiment of a device 175 in which all of the filaments 160 comprise an almond-shaped feature 157, providing even more material that can act as scaffolding to inhibit herniation of objects out of an aneurysm is than in FIGS. 16C and 17B. In some embodiments, the features 157 are hollow (e.g., as depicted in FIGS. 17A-18B). In some embodiments, the widths of the material forming the features 157 is the same as the width of the filaments 160. In some embodiments, the widths of the material forming the features 157 is different than the width of the filaments 160. In some embodiments, the features 157 are solid. Other shapes of features 157 are also possible (e.g. zig-zags, concentric shapes, polygons, spirals, combinations thereof, and the like). In some embodiments, the filaments 160 may comprise more than one feature 157 (e.g., substantially spanning the distal section 159).

Figure 19A:
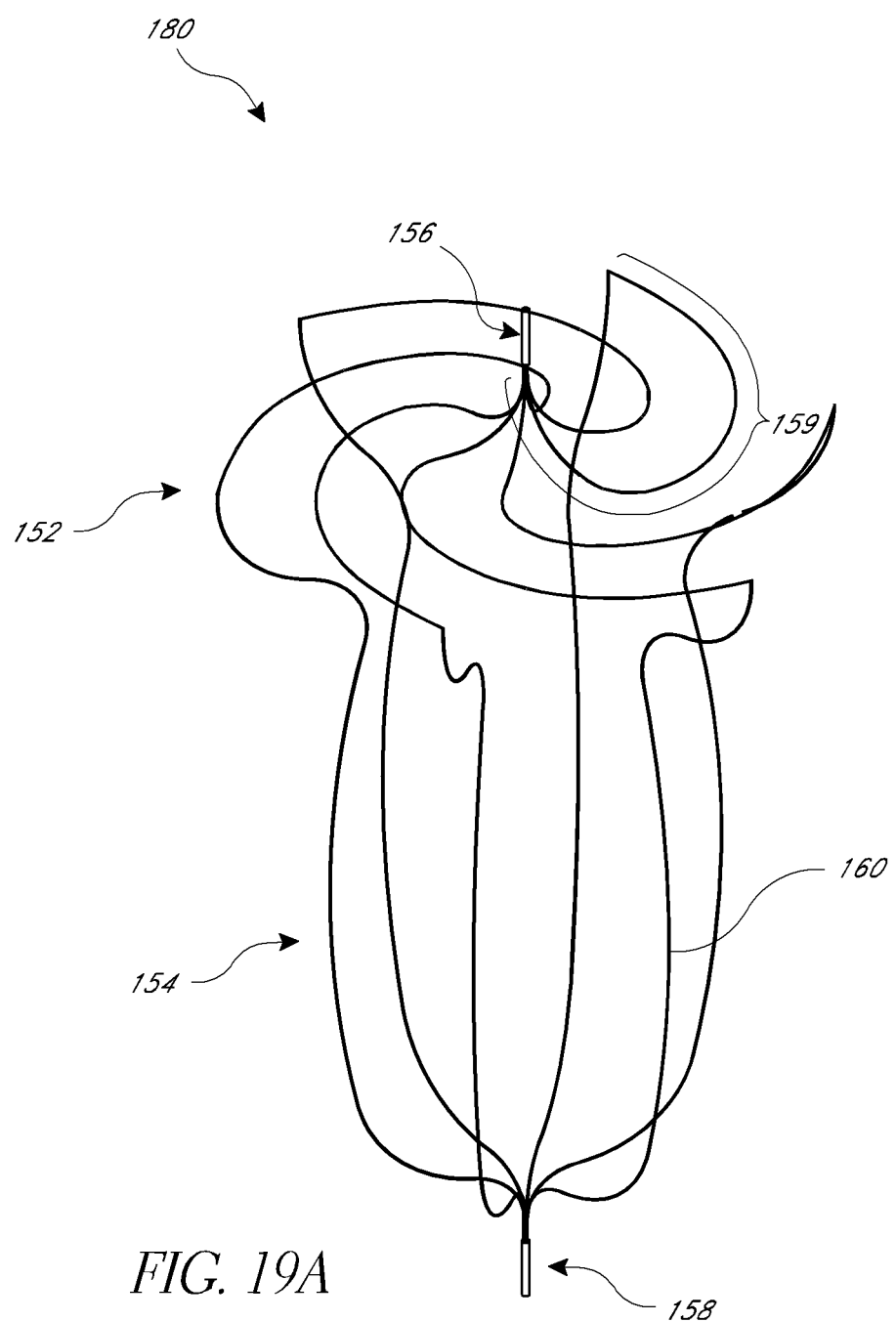
FIG. 19A illustrates a top perspective view of another example embodiment of a vascular remodeling device.
Figure 19B:
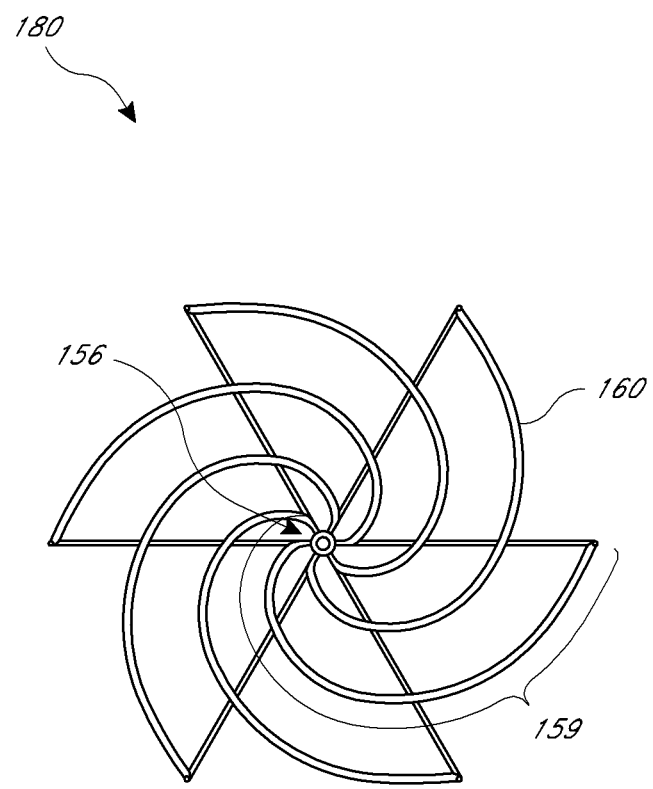
FIG. 19B illustrates a top plan view of the device of FIG. 19A.

FIG. 19A illustrates an example embodiment of a device 180 in which the filaments 160 in the distal section 159 spiral towards the distal end 156 of the device 150 after having been non-overlapping proximal to the distal section 159. In certain such embodiments, the surface area of a distal section 159 of the filaments 160 may be greater than the surface area of the filaments 160 proximal to the distal section 159. FIG. 18B illustrates a top plan view of the device 190, showing the spiral-pattern. Comparing FIG. 16C to FIG. 19B, the amount of material that can act as scaffolding to inhibit herniation of objects out of an aneurysm is greater in FIG. 19B due to the spiral in the distal section 159. Other configurations reducing the porosity near the distal end 156 are also possible. For example, the spirals in the distal section 159 of the device 190 may comprise features 157 as described with respect to the devices 170, 175.

In some embodiments, the device 150 comprises a radiopaque marker 166 proximate to the distal end 156 and/or a radiopaque marker 167 proximate to the proximal end 158. Some embodiments of the device 150 may comprise more than one or two radiopaque markers proximate to the distal and proximal ends 156, 158. In certain embodiments, the radiopaque marker 166 may extend at least partially into the aneurysm 20 when the device 150 is positioned at the junction of a bifurcation. In some embodiments, the radiopaque markers 166, 167 may comprise a sleeve positioned or wrapped around the filaments 160, thereby coupling the filaments 160. The radiopaque markers 166, 167 may aid in positioning the device 150 at the junction of a bifurcation.

In certain embodiments, the device 150 is configured to be highly conformable to the junction of a bifurcation (e.g., a neurovascular bifurcation) comprising at least one afferent vessel, efferent vessels, and an aneurysm 20 having a fundus and a neck. For example, in certain such embodiments, the device 150 comprises filaments 160 comprising a material and having a thickness and cross-sectional shape that conforms to and allows good compliance with the vasculature at the junction of the bifurcation.

In some embodiments, at least one filament 160 of the plurality of filaments 160 comprises a round wire (e.g., having a circular cross-section). In certain such embodiments, the round wire has a diameter between about 0.002" (approx. 0.05 mm) and about 0.006" (approx. 0.15 mm), between about 0.0025" (approx. 0.05 mm) and about 0.004" (approx. 0.10 mm), or between about 0.003" (approx. 0.08 mm) and about 0.0037" (approx. 0.09 mm). In some embodiments, the round wire comprises an outer sheath comprising a first material and an inner core comprising a second material (e.g., comprising platinum, platinum-tungsten, tantalum, silver, or gold). In some embodiments, the second material of the inner core is radiopaque. In some embodiments, at least one filament 160 comprises a thin wire coiled around a round wire. In certain such embodiments, the thin wire has a diameter between about 0.009" (approx. 0.023 mm) and about 0.002" (approx. 0.051 mm), between about 0.001" (approx. 0.025 mm) and about 0.0175" (approx. 0.044 mm), or between about 0.00125" (approx. 0.032 mm) and about 0.0015" (approx. 0.038 mm). In some embodiments, the thin wire comprises platinum, platinum-tungsten, tantalum, silver, or gold. In some embodiments, the thin wire comprises a radiopaque material.

In certain embodiments, at least one filament 160 of the plurality of filaments 160 comprises a flat wire or ribbon (e.g., having a rectangular cross-section). In certain such embodiments, the flat wire has a thickness between about 0.001" (approx. 0.0025 mm) and about 0.003" (approx. 0.076 mm) and a width between about 0.003" and about 0.005", a thickness between about 0.0015" (approx. 0.0381 mm) and about 0.0025" (approx. 0.064 mm) and a width between about 0.0035" (approx. 0.089 mm) and about 0.0045" (approx. 0.114 mm), or a thickness between about 0.00175" (approx. 0.044 mm) and about 0.00225" (approx. 0.057 mm) and a width between about 0.00375" (approx. 0.095 mm) and about 0.00425" (approx. 0.108 mm).

In certain embodiments, the device 150 comprises between about 4 filaments 160 and about 12 filaments 160 or between about 6 filaments 160 and about 12 filaments 160. Other numbers of filaments 160 are also possible. In certain embodiments, combinations of different filaments 160 are used in the same device 150 (e.g., 6 filaments comprising Nitinol and 2 round filaments comprising Nitinol and having a thin platinum wire coiled around the two round filaments).

In some embodiments, the device 150 is reshapable and/or lockable, for example comprising certain features described herein and depicted in FIGS. 6A-7B. In some embodiments, the device 150 may further comprise a covering as described herein and depicted in FIGS. 8A and 8B. In certain embodiments the distal ends of the filaments 160 comprise a coating configured to preferentially repel certain material. In some embodiments, the coating is configured to preferentially repel liquid embolic material (e.g. Onyx'). In some embodiments, forming the coating on the distal ends of the filaments 134 comprises chemically treating the filaments 160. Certain such coatings may allow delivery of liquid embolic material through the device 150 while inhibiting, reducing, or preventing permeation of the liquid embolic material from out of the aneurysm through the device 150.

A highly conformable remodeling device comprising filaments 160 such as certain embodiments described herein may possess greater conformability at the junction of a bifurcation 60 than a balloon-remodeling device designed to perform the same function (for example those described herein and in U.S. patent application Ser. No. 10/235,064, filed Sep. 4, 2002, and U.S. patent application Ser. No. 11/868,049, filed Oct. 5, 2007, each of which are incorporated herein by reference in its entirety), for example possibly because a balloon has a continuous surface that generally wholly conforms to a junction, whereas a highly conformable remodeling device described herein only conforms to the junction where the filaments 160 contact the vasculature.

A highly conformable remodeling device comprising filaments 160 such as certain embodiments described herein may reduce damage to vasculature by permitting blood to flow to efferent vessels of a bifurcation 60 throughout a treatment process after a single deployment from a catheter, whereas a balloon-remodeling device generally occludes flow to the efferent vessels such that the balloon is periodically deflated in order to restore perfusion, and such repeated inflation and deflation may damage the vasculature.

Figure 20A:
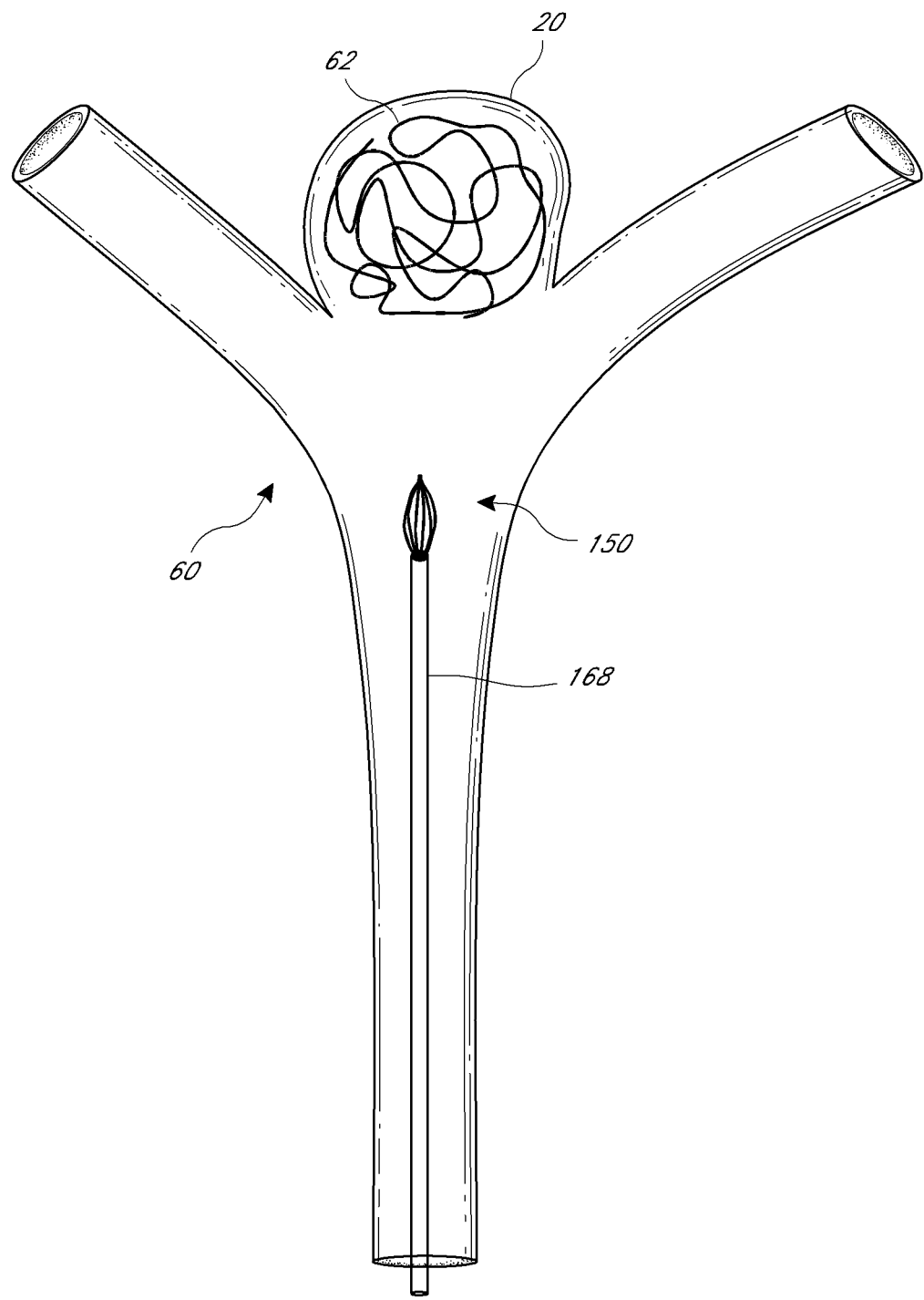
FIGS. 20A-20D illustrate an example embodiment of a method for treating an aneurysm using the device of FIG. 15A.
Figure 20B:
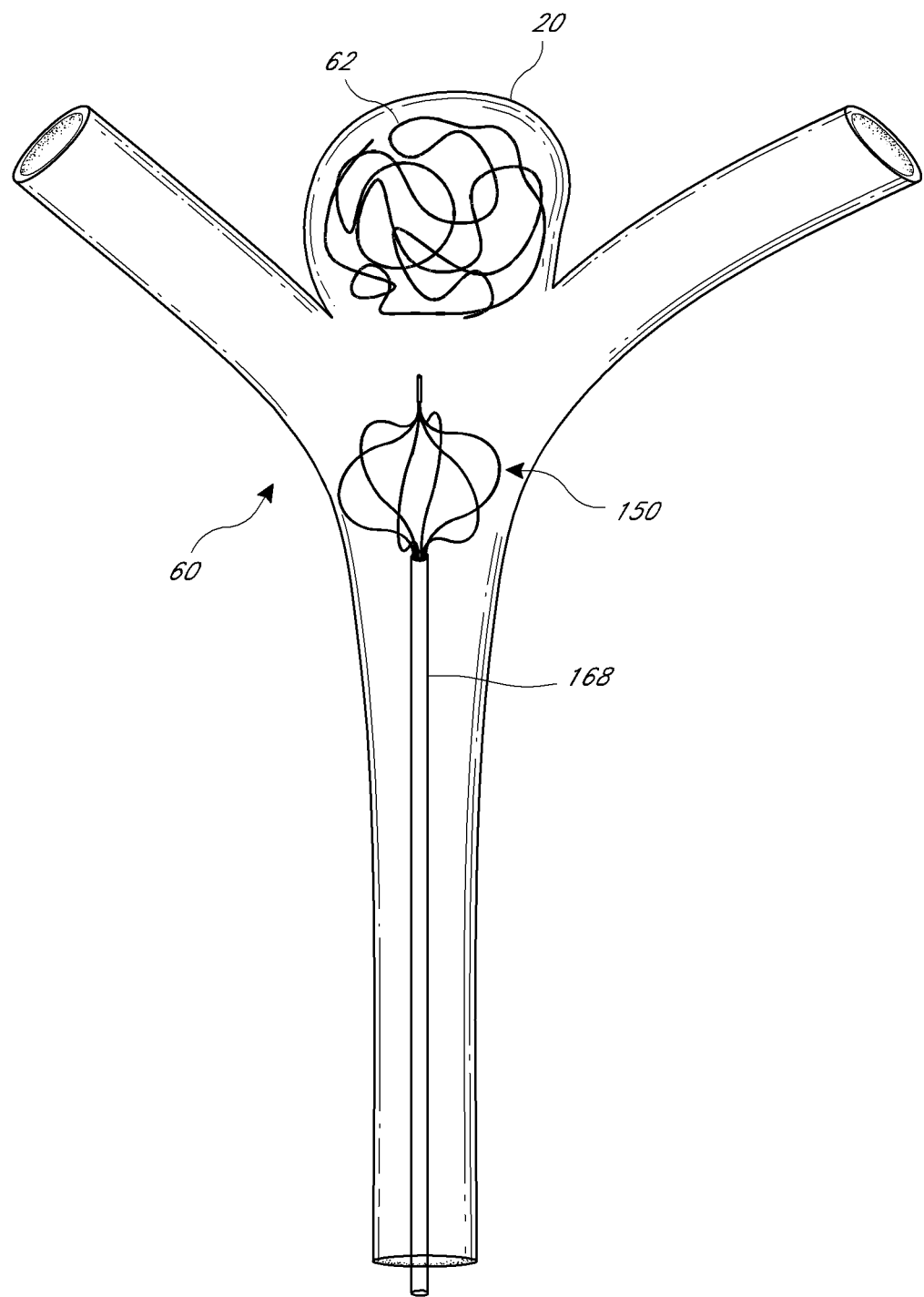
Figure 20C:
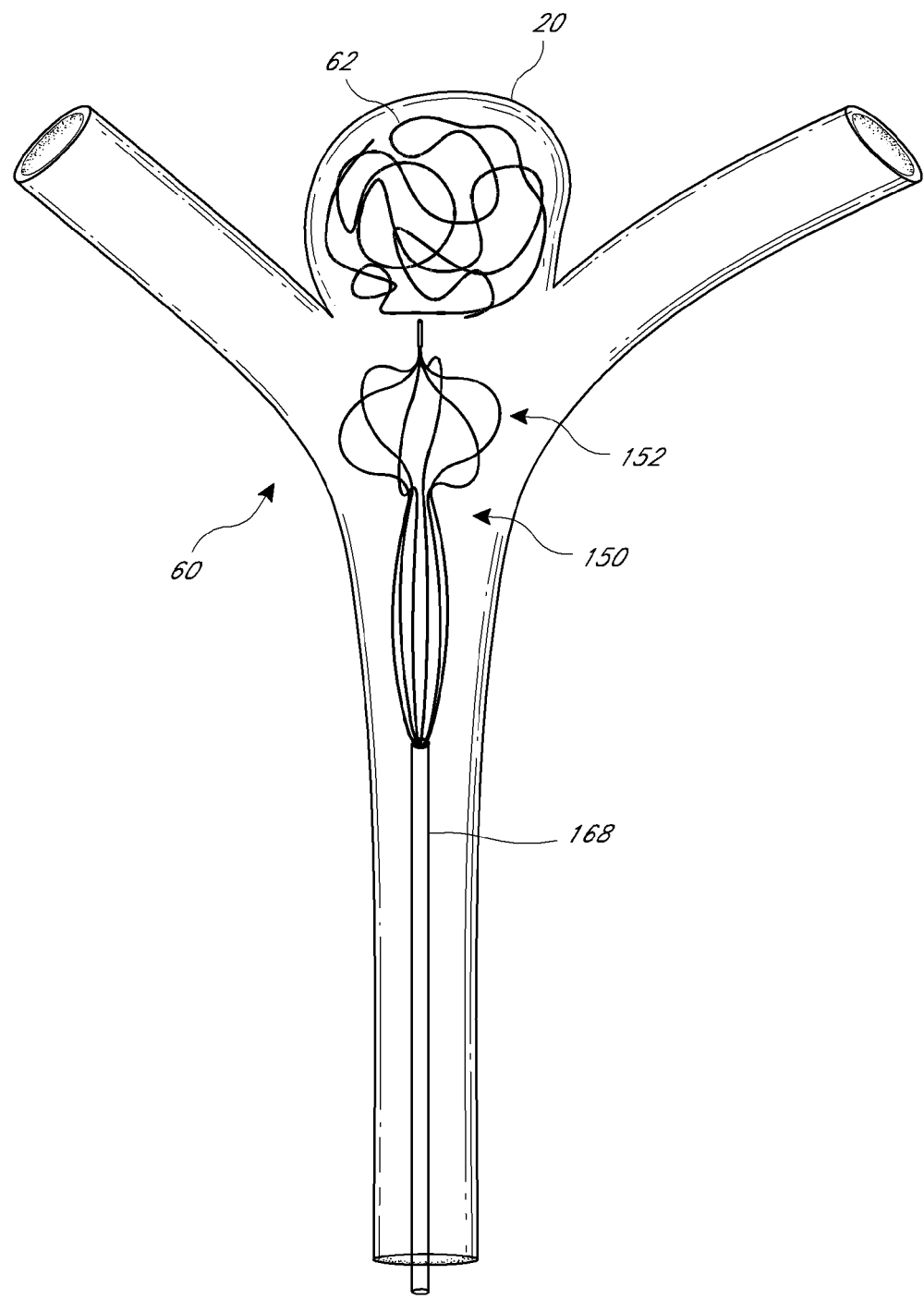
Figure 20D:
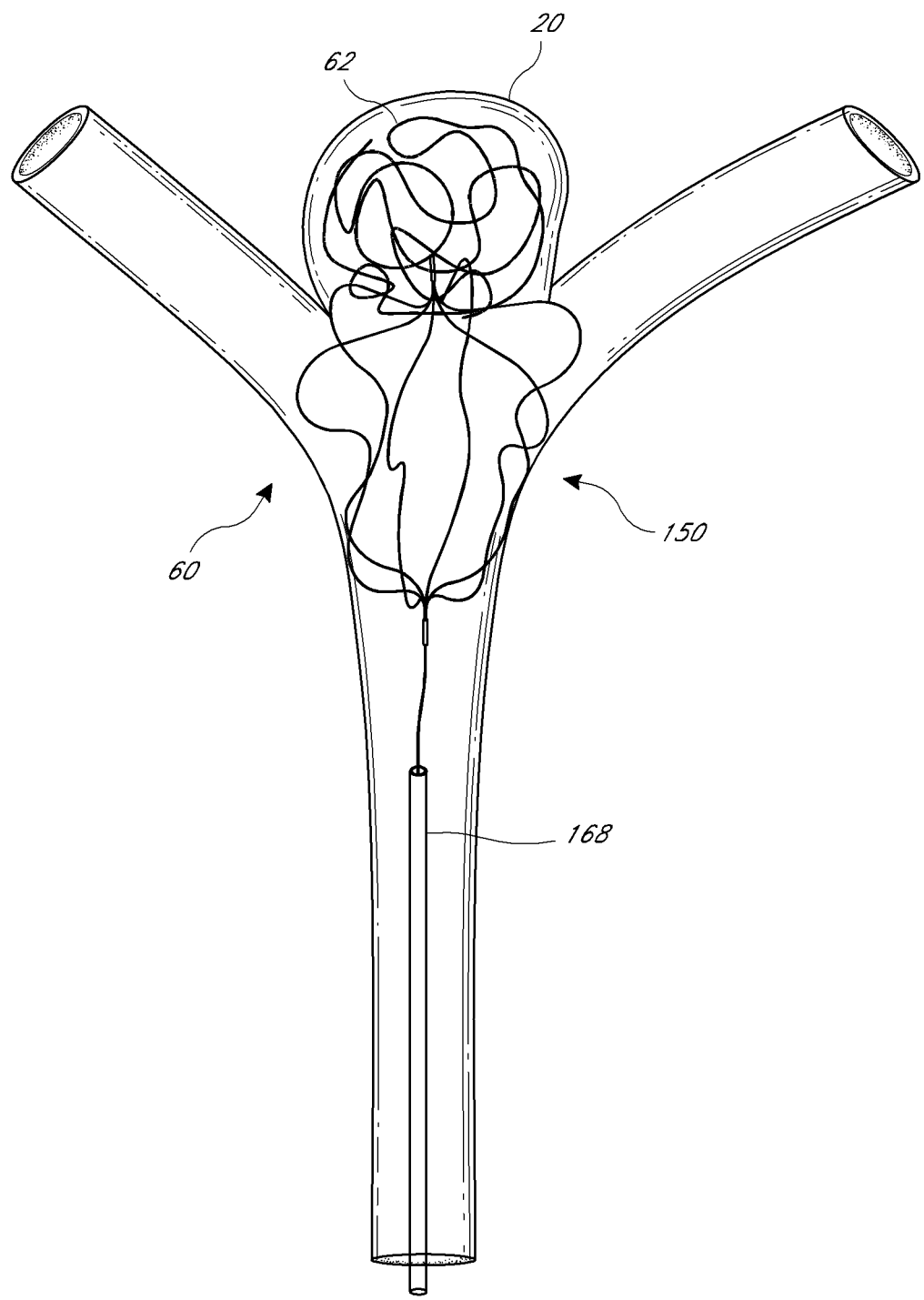

FIGS. 20A-20D illustrate an example embodiment of a method for treating an aneurysm 20 using an apparatus comprising a device 150 (or a device 170, 175. 180) and a catheter 168. FIG. 20A illustrates a confluence of afferent and efferent vessels or "junction" at a bifurcation 60 having an aneurysm 20. In some embodiments, the vessels are neurovascular or cranial. The aneurysm 20 may be treated by inserting material into the aneurysm 20. The aneurysm 20 is illustrated with a plurality of embolization coils 62 having been inserted in the fundus of the aneurysm 20. It will be appreciated that the embolization coils 62 may be a single embolization coil or other embolic material (e.g., Onyx® liquid embolic material). A catheter 168 (e.g., a microcatheter), at least partially containing a constricted or compressed device 150, is also shown in the afferent vessel. The catheter 168 is small enough and flexible enough to be routed through the vasculature and situated proximate to the aneurysm 20, as shown in FIG. 20A. The device 150 may be pre-loaded into or pushed through the situated catheter 168. In some embodiments, the embolization coils 62 are inserted in the fundus of the aneurysm 20 using the catheter 168. In some embodiments, the embolization coils 62 are inserted in the fundus of the aneurysm 20 using a different catheter. In certain such embodiments, a guidewire may be used to guide both catheters.

FIGS. 20A-20C illustrate the bifurcation 60 as the device 150 is being deployed from the catheter 168 at the junction of the bifurcation 60. In some embodiments, the device 150 is deployed from the catheter 168 (e.g., by being pushed out with a plunger or pusher wire, by retracting the catheter 168 while the device 150 remains stationary, combinations thereof, and the like) at the junction of the bifurcation 60. During and/or after being deployed from the catheter 168, parts of the device 150 may expand. In some embodiments, the device 150 comprises a self-expanding and/or a shape-memory material that automatically expands towards an uncompressed state or expands towards an uncompressed state upon the application of warm fluid (e.g., saline). In some embodiments, the device 150 expands upon being forced radially outwardly by a balloon upon inflation. The device 150 may substantially conform to the shape of the junction of the bifurcation 60. FIG. 20C shows the distal portion 152 of the device 150 in a more expanded state, but not fully deployed, state. FIG. 20D depicts the device 150 after the device 150 has been fully deployed from the catheter 168. In some embodiments, the device 150 may substantially conform to the shape of the junction of the bifurcation 60 (e.g., not substantially including portions extending into the afferent and efferent vessels) and locks into place across the ostia of the afferent and efferent vessels and the neck of the aneurysm 20. The device 150 at least partially covers the neck of the aneurysm 20 as well as the afferent and efferent vessels, but does not need to divert flow. The device 150 acts as a scaffolding to inhibit or prevent herniation or prolapse of objects such as the embolization coils 62 and/or thrombi out of the aneurysm 20. The device 150 also allows perfusion of fluid (e.g., blood) from the afferent vessel(s) to the efferent vessel(s).

In some embodiments, the device 150 may be retracted into the catheter 168 after being deployed from the catheter 168 (e.g., by pulling on a tail). The device 150 may then be redeployed, for example at a new angle, at a new rotational position, more proximal or distal to an afferent vessel and/or an efferent vessel, etc. For example, although the device 150 expands towards an uncompressed state after deployment, the resulting shape of the device 150 at the junction of the bifurcation 60 may vary depending on the details of the deployment from the catheter 168 because the device 150 adapts to the shape of the anatomy (e.g., due to the size, shape, number, etc. of the filaments 160). Once the user is satisfied with properties of the device 150 (e.g., position, tilt, rotation, shape interaction with the vesels, etc.), the device 150 may be optionally released (e.g., electrolytically, chemically, mechanically (e.g., using the mechanisms described herein), etc).

In some embodiments, the device 150 is not attached or otherwise coupled to the distal end of the catheter 168 and can be pushed out of the catheter 168 (e.g., using a plunger or pusher wire). In certain such embodiments, the device 150 is not respositionable or resheathable.

It will be appreciated that the devices described herein (e.g., devices 70, 80, 85, 110, 130, 150, 170, 175, 180) may be used in any of the methods described herein (e.g., the method described with respect to FIGS. 9Ci-9Ciib, the methods described with respect to FIGS. 13A-13D, the methods described with respect to FIGS. 20A-20D), combinations of the same, or the like.

In some embodiments, the aneurysm 20 is treated after the device 150 has been deployed from the catheter. For example, the embolization coils 62 may be inserted in the fundus of the aneurysm 20 after the device 150 has been deployed from the catheter 168. The device 150 may remain connected to the catheter 168 for the total duration of its deployment. The device 150 may then be retracted into the catheter 168 and the entire apparatus may be withdrawn from the vasculature. Different combinations are also possible. For example, the embolization coils 62 may be inserted in the fundus of the aneurysm 20 after deployment of the device 150, but prior to withdrawal of the apparatus or optional release of the device 150 from the catheter 168. For another example, the embolization coils 62 may alternatively be inserted in the fundus 22 of the aneurysm 20 after the device has been deployed and released from the catheter 168. For another example, the embolization coils 62 may be inserted into the fundus of the aneurysm 20 after the device 150 has been deployed from the catheter 168 (e.g., in a coil state), and the device 168 may be retracted and redeployed from the catheter 168 (e.g., in a final state).

In certain embodiments, the device 150, 170, 175, 180 may comprise sufficient scaffolding in the distal section to divert blood flow from the aneurysm 20. In some embodiments, properties of the filaments 160 (e.g., filament density, filament configuration, filament surface area, etc.) may cause low porosity. In some embodiments, a covering proximate to the distal end 156 may reduce porosity. An ability to divert blood flow from the aneurysm 20 may reduce pressure on the aneurysm 20 and may be useful, for example, in treating aneurysms 20 comprising a wide neck.

Figure 21:
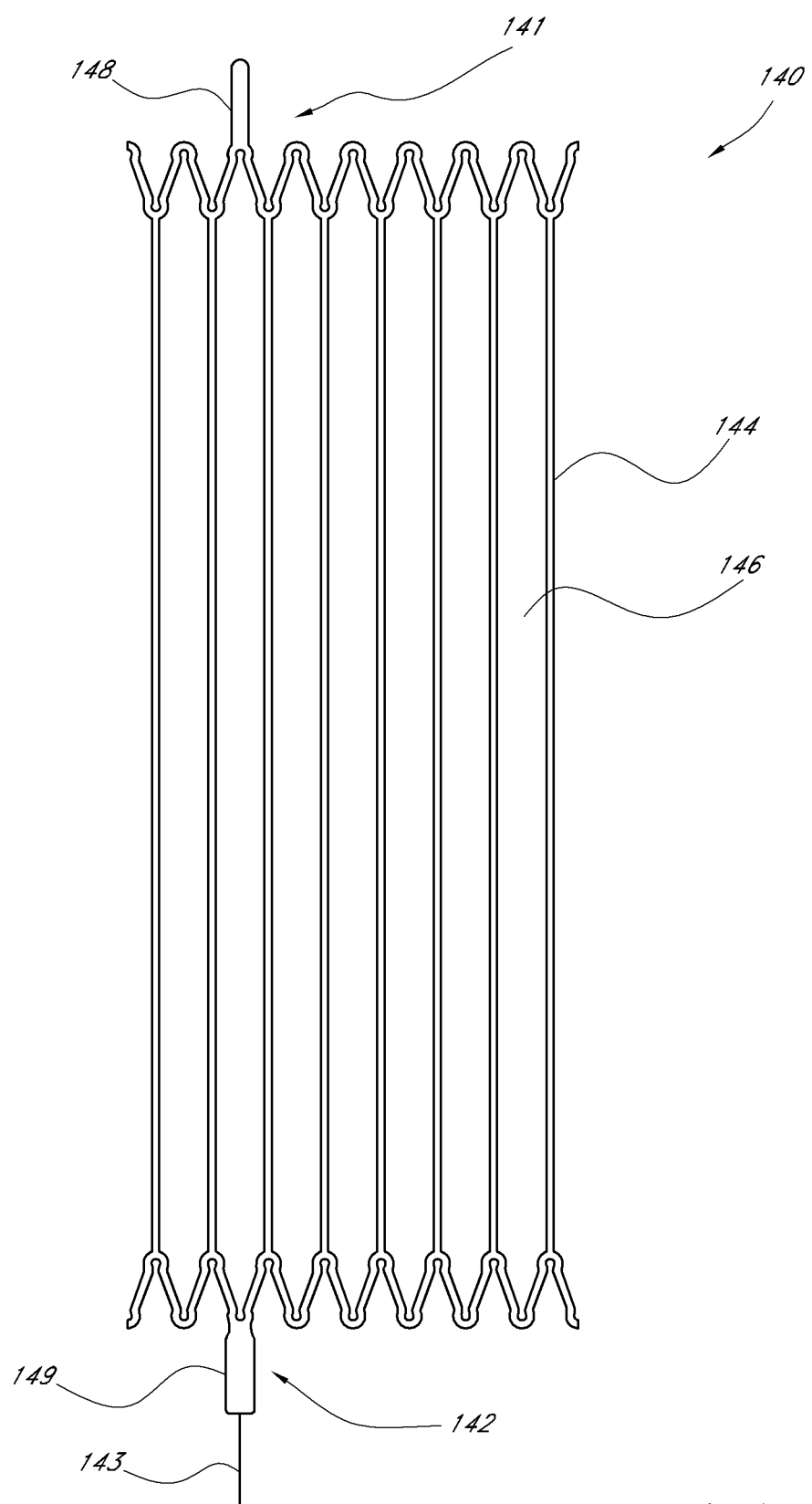
FIG. 21 illustrates an example embodiment of a vascular remodeling device at a stage of an example manufacturing process.

FIG. 21 illustrates an example embodiment of a vascular remodeling device 140 at a stage of an example manufacturing process comprising cutting and shaping a metallic tube (e.g., a laser cut hypotube), albeit illustrated in a flat form. It will be appreciated that certain methods described herein also work for cutting a flat sheet and then forming a tube (e.g., either attaching the lateral edges or leaving an open slit). In some embodiments, the starting tube has a diameter between about 0.5 mm and about 3 mm or between about 1 mm and about 2 mm (e.g., about 1 mm, about 1.5 mm, about 2 mm, etc.). Other diameters are also possible.

The device 140 has a first or distal end 141 and a second or proximal end 142 substantially opposite the distal end 141. A laser may cut out portions 146 of the tube, leaving a plurality of filaments 144 extending between the distal end 141 and the proximal end 142. In the embodiment illustrated in FIG. 21, the filaments 144 are coupled at the distal end 141 and the proximal end 142 (e.g., due to being integrally formed with the metallic tube and not cut away from each other). In some embodiments, a lead or tail 143, which may be used for releasing and/or retracting the device 140 after deployment, for example as described herein, may be attached to the device 140 (e.g., by adhering, soldering, welding, etc.). In certain embodiments, a tail 143 may be integral with the device 140 by being defined by the cut tube.

In some embodiments, the device 140 further comprises a radiopaque marker 148 proximate to the distal end 141 and/or a radiopaque marker 149 proximate to the proximal end 142. In certain embodiments, the radiopaque marker 148 may extend at least partially into the aneurysm 20 when the device 140 is positioned at the junction of a bifurcation 60. In some embodiments, the radiopaque markers 148, 149 may be integral with the device by being defined by the cut tube. The radiopaque markers 148, 149 may aid in positioning the device 140 at the junction of a bifurcation 60.

The cut tube can then be expanded into a desired shape (e.g., a shape of the devices described herein) through shape setting using a heat treatment process. The shape setting process may include several steps comprising of successively increasing sizes of the desired shapes using appropriate tooling to stretch and confine the cut tube into a new shape while heat treating it. At the end of the each heat treatment step, the cut tube assumes the shape in which it was confined during the heat treatment process. This process is then repeated to form a slightly larger size and a shape closer to the end product. The final shape (e.g., a football shape similar to the device 80) and size may obtained by several such steps. Other devices described herein (e.g., the devices 110, 130, 150, 170, 175, 180) may also be formed using cut a metallic tube that is reshaped after being cut, although it will be appreciated that the pattern of the initial cut may be different, for example materials, dimensions, porosities, deployment methods, possibly coverings, etc. In certain embodiments of forming the devices 170, 175, the features 157 may be integrally cut from the tube. In certain embodiments of forming the devices 170, 175, the features 157 may be attached (e.g., by adhering, soldering, welding, etc.) to the tube after cutting.

Certain devices described herein may be advantageously used to treat aneurysms having a neck ratio (a ratio of fundus width to neck width) greater than about 2 to 1 and/or a neck width greater than about 4 mm. In treatment of such aneurysms, embolization coils may be prone to herniating into parent vessels because the size and/or shape of the aneurysm is not conducive to maintaining the coils in their inserted locus. In certain such embodiments, embolization coils are inserted in the fundus of the aneurysm after positioning a generally spherical device so that the embolization coils do not have an opportunity to herniate. It will be appreciated that certain devices described herein may also be used to treat aneurysms having a neck ratio less than about 2 to 1 and/or a neck width less than about 4 mm. In certain such embodiments, embolization coils are inserted in the fundus of the aneurysm before positioning a generally spherical device.

Certain devices described herein may advantageously comprise a single device placed at a junction of a bifurcation rather than a plurality of tubular bifurcations. Certain such devices can span a neck of an aneurysm as well as arterial ostia. Positioning such devices may be less complicated, thereby reducing risks associated with, for example, than ensuring that a tubular device is properly anchored in an afferent vessel and in an efferent vessel.

Figure 1:
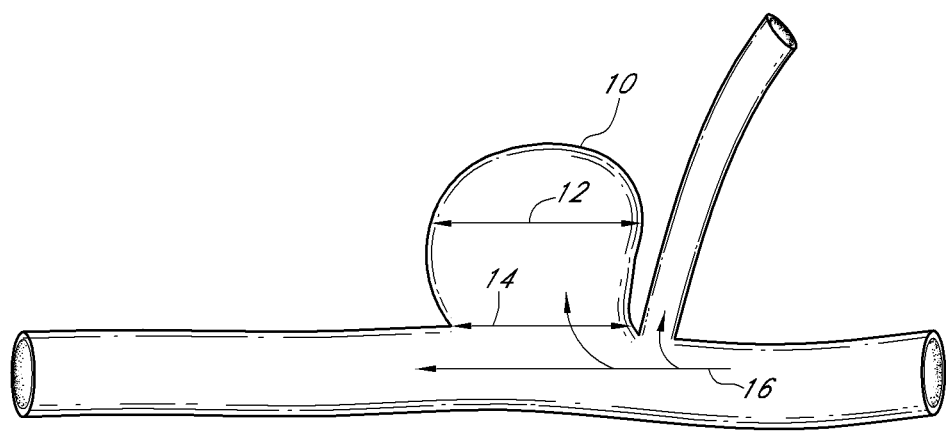
FIG. 1 illustrates an example embodiment of a side wall aneurysm.
Figure 2:
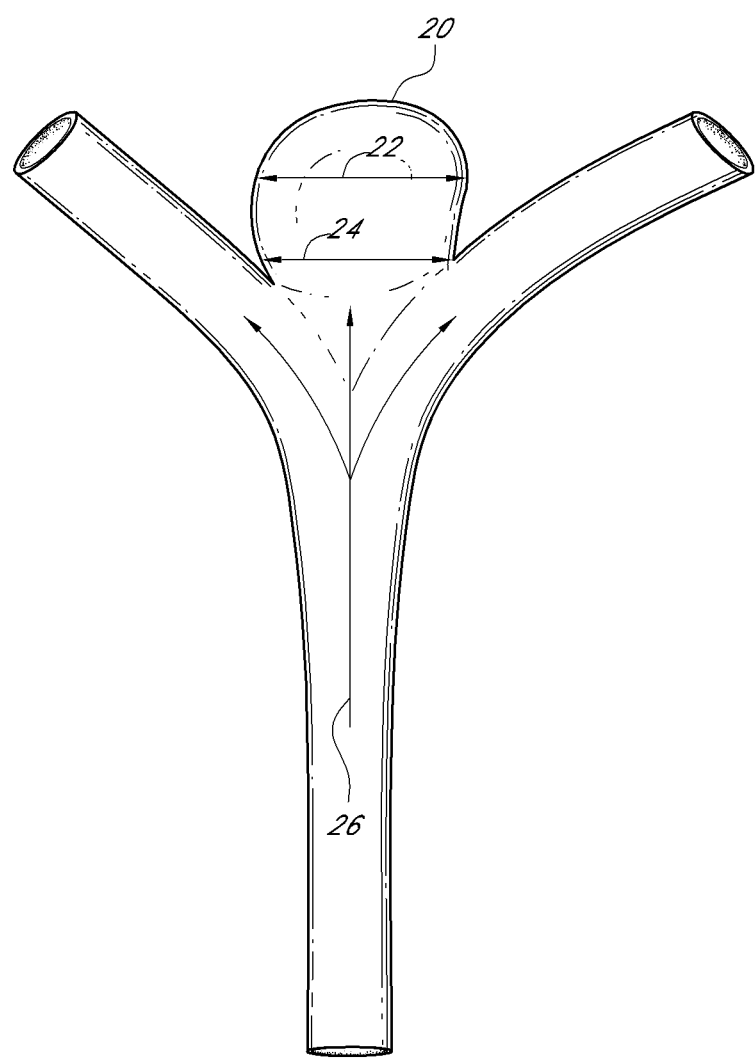
FIG. 2 illustrates an example embodiment of a bifurcation having an aneurysm.
Figure 3A:
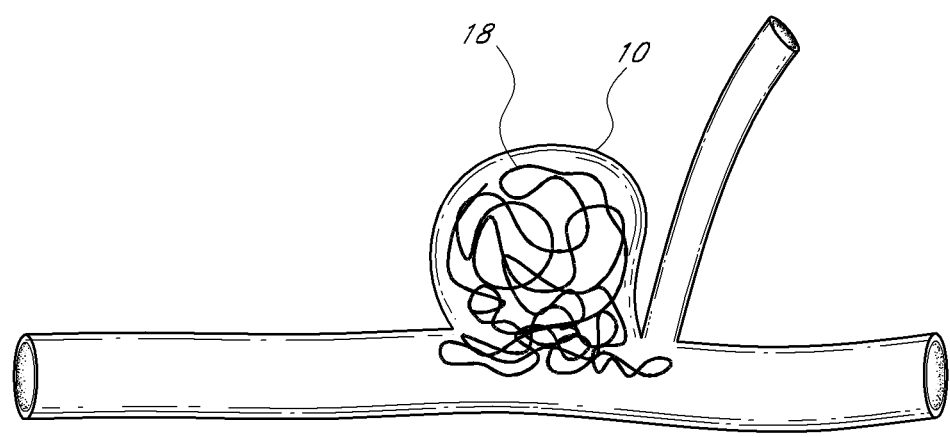
FIG. 3A illustrates an example embodiment of a side wall aneurysm with herniating embolization coils.
Figure 3B:
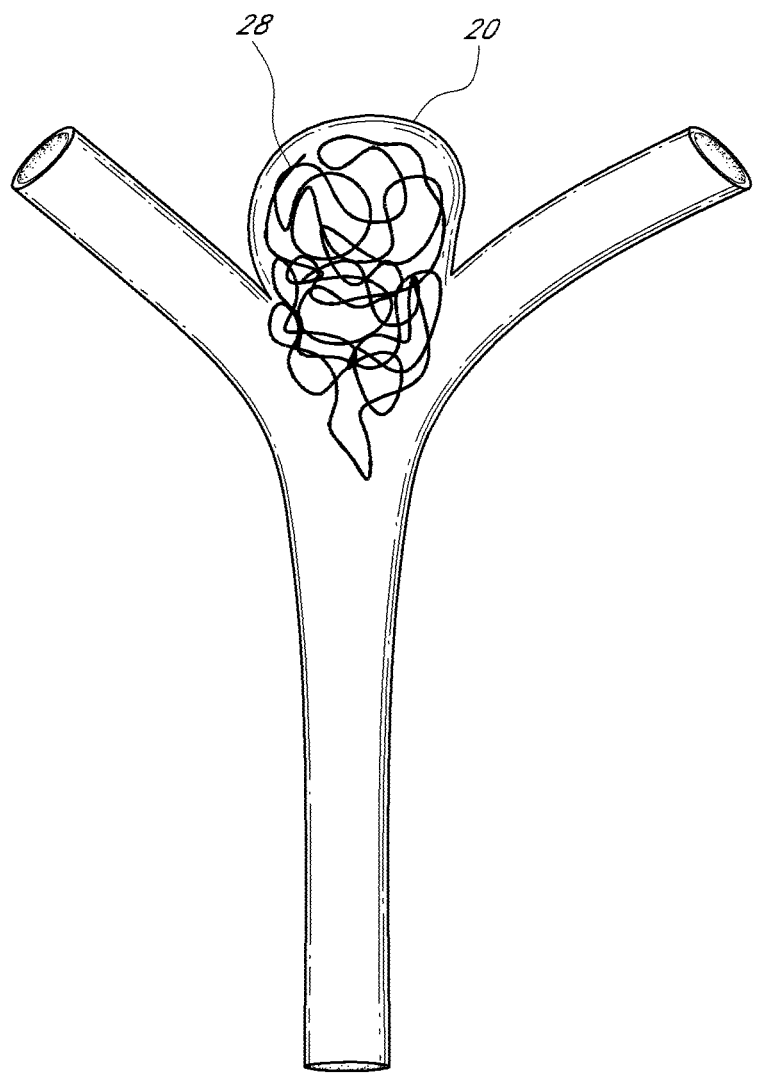
FIG. 3B illustrates an example embodiment of a bifurcation having an aneurysm with herniating embolization coils.
Figure 4A:
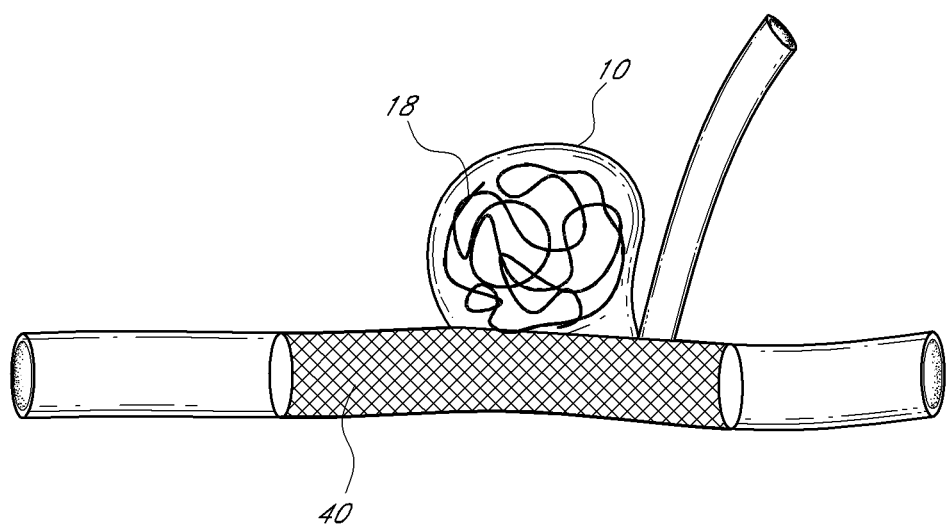
FIG. 4A illustrates an example embodiment of a side wall aneurysm treated with embolization coils and a tubular remodeling device.
Figure 4B:
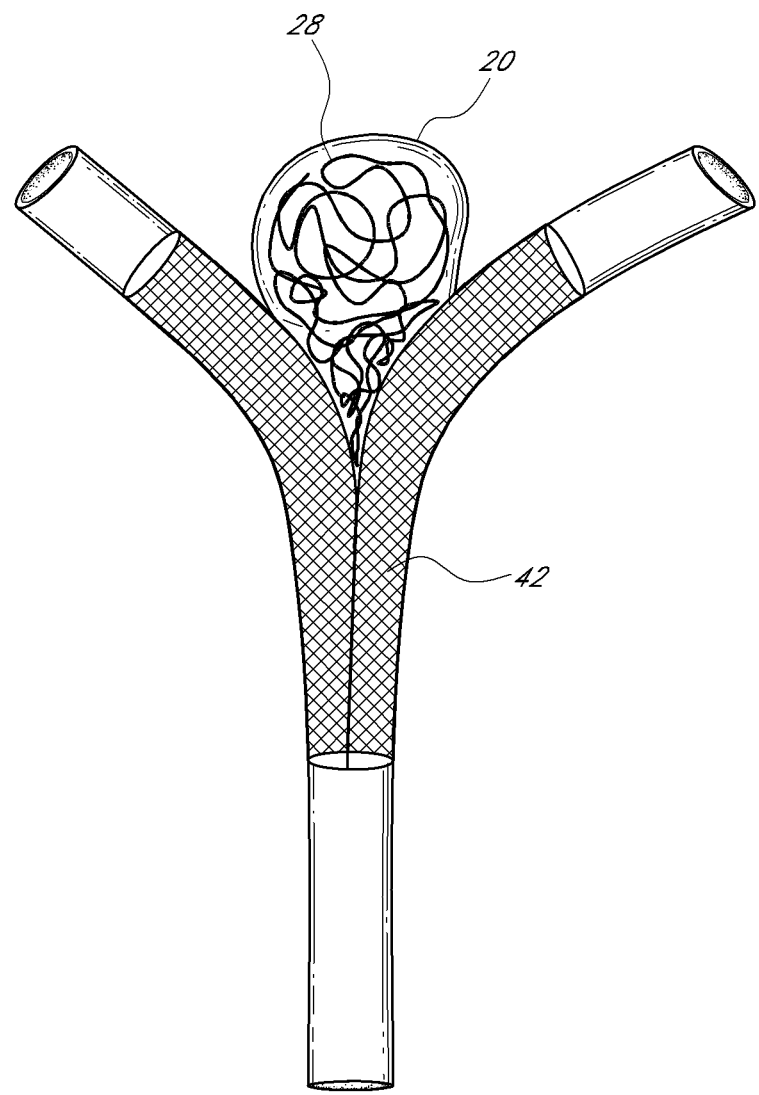
FIGS. 4B and 4C illustrates example embodiments of a bifurcation having an aneurysm treated with embolization coils and tubular remodeling devices.
Figure 4C:
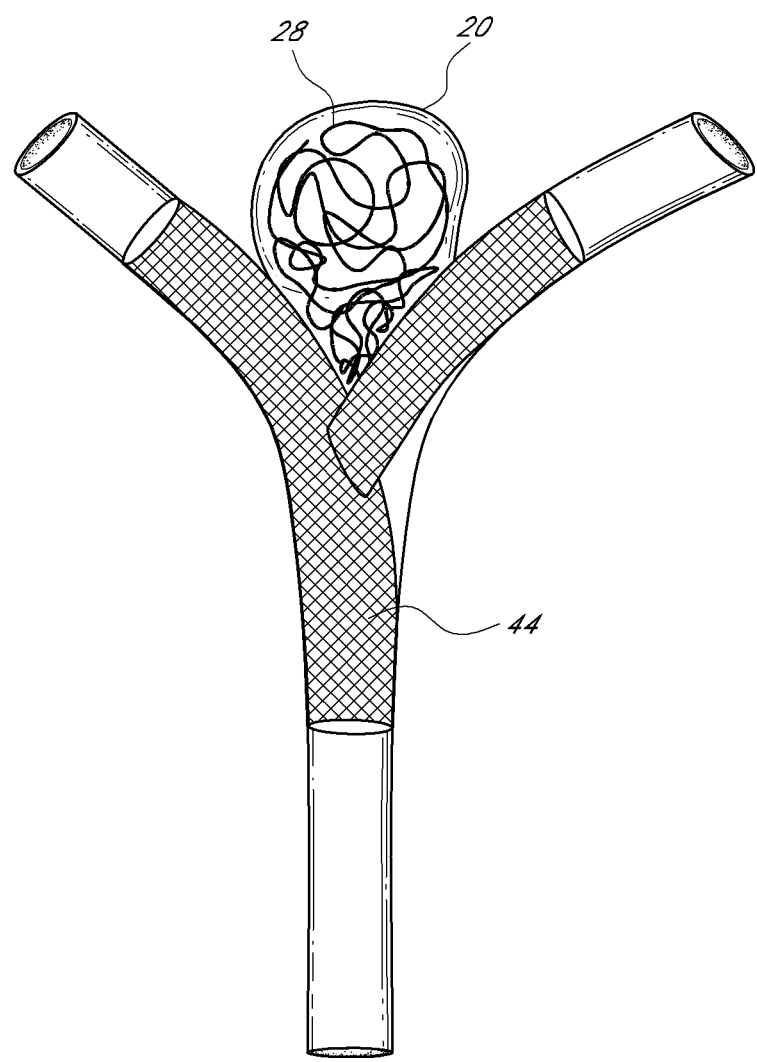

In some embodiments in which embolic material was previously inserted in an aneurysm but has herniated, certain devices described herein may be used as a "rescue device" to push the herniated material back into the aneurysm and to act as a scaffolding to inhibit or prevent further herniation or prolapse of the embolic material. In certain such embodiments, deployment of such devices may advantageously avoid traversal of the junction comprising the herniated material by wires or a catheter (e.g., there is no need to traverse wires or a catheter past the junction into an efferent vessel for positioning of the device as is generally needed to position tubular devices such as the devices 42, 44 illustrated in FIGS. 4B and 4C), which may cause the herniated material to become tangled and/or dislodged and which may cause rupture of the aneurysm.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

What is claimed is:

1. A method of treating an aneurysm at a junction of a bifurcation having an afferent vessel and efferent vessels, the aneurysm having a neck and a fundus, the method comprising:

advancing a catheter proximate to the junction of the bifurcation, the catheter at least partially containing a device in a compressed state, the device comprising a proximal end, a distal end, and a middle region between the proximal end and the distal end, the middle region consisting of a plurality of filaments extending from the proximal end to the distal end, the plurality of filaments being coupled at and only at both the proximal end and the distal end;

deploying the device from at least partially inside the catheter to outside the catheter with a distal portion of the device at the junction of the bifurcation abutting the neck and a proximal portion expanded against walls of the afferent vessel, the distal portion having a distal cross-sectional dimension greater than a proximal cross-sectional dimension of the proximal portion, wherein, during deployment, the device self-expands to conform in an expanded state to the junction of the bifurcation, and wherein, after deployment and while the proximal end of the device is connected to the catheter, the device acts as a scaffolding to inhibit herniation of objects out of the neck of the aneurysm and permits perfusion of fluid to the efferent vessels, wherein the distal portion of the device comprises a distal section, the plurality of filaments spiraling towards the distal end in the distal section; and withdrawing the catheter.

2. The method of claim 1, further comprising inserting embolic material into the aneurysm.

3. The method of claim 1, wherein deploying the device comprises locking the device into place across ostia of the afferent and efferent vessels and the neck of the aneurysm.

4. The method of claim 1, wherein deploying the device further comprises:
  retracting the device into the catheter; and re-deploying the device in at least one of a second orientation and a second position, wherein, during re-deployment, the device self-expands to conform to the junction of the bifurcation.

5. The method of claim 1, further comprising retracting the device at least partially back inside the catheter.

6. The method of claim 1, further comprising releasing the device from the catheter.

7. The method of claim 1, further comprising withdrawing the device.

8. The method of claim 1, further comprising leaving the device.

9. The method of claim 1, wherein the plurality of filaments define a middle portion between the proximal portion and the distal portion, the middle portion having a cross-sectional dimension less than each of the proximal cross-sectional dimension and the distal cross-sectional dimension, wherein the deploying comprises positioning the middle portion between the afferent vessel and the efferent vessels.

10. The method of claim 1, wherein, after the deploying, the filaments of the plurality of filaments have segments in the proximal portion that are parallel to each other.

11. The method of claim 1, wherein the deploying comprises positioning the distal portion, having the distal cross-sectional dimension, outside the aneurysm.

12. A method of treating an aneurysm at a junction of a bifurcation having an afferent vessel and efferent vessels, the aneurysm having a neck and a fundus, the method comprising:
  advancing a catheter proximate to the junction of the bifurcation, the catheter at least partially containing a device in a compressed state, wherein the device comprises a proximal end, a distal end, and a middle region between the proximal end and the distal end, the middle region consisting of (i) a plurality of filaments and (ii) a central filament, wherein the plurality of filaments and the central filament extend from the proximal end to the distal end, and are coupled at and only at both the proximal end and the distal end;
  deploying the device from at least partially inside the catheter to outside the catheter with a distal portion of the device at the junction of the bifurcation abutting the neck and a proximal portion expanded against walls of the afferent vessel, wherein, during deployment, the device self-expands to conform to the junction of the bifurcation, the distal portion having a distal cross-sectional dimension greater than a proximal cross-sectional dimension of the proximal portion;
  reshaping the deployed device by using the central filament to adjust a distance between a proximal end of the device and a distal end of the device and securing a portion of the central filament to the proximal end to lock the device in a reshaped state, wherein, after deployment, the device acts as a scaffolding to inhibit herniation of objects out of the neck of the aneurysm and permits perfusion of fluid to the efferent vessels, wherein the distal portion of the device comprises a distal section, the plurality of filaments spiraling towards the distal end in the distal section; and
  withdrawing the catheter.

13. The method of claim 12, further comprising retracting the device at least partially back inside the catheter.

14. The method of claim 12, further comprising releasing the device from the catheter.

15. The method of claim 12, further comprising withdrawing the device.

16. The method of claim 12, further comprising leaving the device.

17. The method of claim 12, wherein the plurality of filaments define a middle portion between the proximal portion and the distal portion, the middle portion having a cross-sectional dimension less than each of the proximal cross-sectional dimension and the distal cross-sectional dimension, wherein the deploying comprises positioning the middle portion between the afferent vessel and the efferent vessels.

18. The method of claim 12, wherein, after the deploying, the filaments of the plurality of filaments have segments in the proximal portion that are parallel to each other.

19. The method of claim 12, wherein the deploying comprises positioning the distal portion, having the distal cross-sectional dimension, outside the aneurysm.

* * * * *